US012636012B2

(12) United States Patent
Johnson Barker et al.

(10) Patent No.: US 12,636,012 B2
(45) Date of Patent: May 26, 2026

(54) COMPRESSION ANASTOMOSIS SYSTEM, AND USE THEREOF

(71) Applicant: PLIO SURGICAL LIMITED, Malahide (IE)

(72) Inventors: Stephen Johnson Barker, Malahide (IE); Donal Healion, Malahide (IE); Cristina Purtill, Malahide (IE)

(73) Assignee: PLIO SURGICAL LIMITED, Malahide (IE)

( * ) Notice: Subject to any disclaimer, the term of this patent is extended or adjusted under 35 U.S.C. 154(b) by 151 days.

(21) Appl. No.: 18/546,209

(22) PCT Filed: Dec. 22, 2021

(86) PCT No.: PCT/EP2021/087431
§ 371 (c)(1),
(2) Date: Aug. 11, 2023

(87) PCT Pub. No.: WO2022/171349
PCT Pub. Date: Aug. 18, 2022

(65) Prior Publication Data
US 2024/0115265 A1     Apr. 11, 2024

(30) Foreign Application Priority Data
Feb. 12, 2021    (EP) ..................................... 21156978

(51) Int. Cl.
*A61B 17/11*        (2006.01)
*A61B 17/122*       (2006.01)
*A61B 17/00*        (2006.01)
(52) U.S. Cl.
CPC ........ *A61B 17/1114* (2013.01); *A61B 17/122* (2013.01); *A61B 2017/00004* (2013.01);
(Continued)

(58) Field of Classification Search
CPC .............. A61B 17/1114; A61B 17/122; A61B 2017/00004; A61B 2017/00477;
(Continued)

(56) References Cited

U.S. PATENT DOCUMENTS 4,693,249 A * 9/1987 Schenck ................ A61B 17/11
606/153
9,320,524 B2   4/2016 Gagner et al.
(Continued)

FOREIGN PATENT DOCUMENTS

CN        103948410 A     7/2014
CN        203988193 U    12/2014
(Continued)

OTHER PUBLICATIONS

Kawai. Biodegradation of Polyethers (Polyethylene Glycol, Polypropylene Glycol, Polytetramethylene glycol, and Others) Part 9. Miscellaneous Biopolyomers and Biodegradation of Polymers. 2005. 47 pages.

(Continued)

*Primary Examiner* — Richard G Louis
(74) *Attorney, Agent, or Firm* — Casimir Jones, S.C.; Kelly A. Barton

(57)                ABSTRACT

A compression anastomosis system comprises matching first and second compression ring devices (1, 40, 50, 60, 70, 80, 90), each compression ring device configured for adjustment from an elongated delivery configuration suitable for passing through a minimally invasive surgical instrument to a deployed radially expanded configuration dimensioned to circumferentially abut an inner wall of a body lumen. The compression rings comprise coupling elements (20, 41, 56, 57) for coupling the rings together in a face-to-face compression anastomosis configuration, and each compression ring device has a radially outward facing surface (10)

(Continued)

comprising tissue anchors (12, 58) configured to anchor the ring to the wall of the body lumen when the ring is deployed in the body lumen. A method of forming a compression anastomosis in a body lumen such as a colon is also described.

23 Claims, 44 Drawing Sheets

(52) U.S. Cl.
CPC .............. *A61B 2017/00477* (2013.01); *A61B 2017/00557* (2013.01); *A61B 2017/00876* (2013.01); *A61B 2017/1117* (2013.01); *A61B 2017/1132* (2013.01)

(58) Field of Classification Search
CPC ........... A61B 2017/00557; A61B 2017/00876; A61B 2017/1117; A61B 2017/1132; A61B 17/0643; A61B 2017/0641
See application file for complete search history.

(56) References Cited

U.S. PATENT DOCUMENTS

| | | | |
|---|---|---|---|
| 10,154,844 B2 | 12/2018 | Sharma | |
| 10,206,682 B2 | 2/2019 | Bakos et al. | |
| 10,555,735 B2 | 2/2020 | Bakos et al. | |
| 10,682,143 B2 | 6/2020 | Hernandez et al. | |
| 11,219,459 B2 | 1/2022 | Ruebeck | |
| 11,607,222 B2 | 3/2023 | Brahmstedt et al. | |
| 2002/0082625 A1 | 6/2002 | Huxel et al. | |
| 2003/0144675 A1* | 7/2003 | Nicolo | ............... A61B 17/1152 |
| | | | 606/153 |
| 2005/0027308 A1* | 2/2005 | Davis | ................. A61B 17/0644 |
| | | | 606/153 |
| 2008/0015617 A1 | 1/2008 | Harari et al. | |
| 2008/0147101 A1 | 6/2008 | Ortiz et al. | |
| 2009/0012543 A1 | 1/2009 | Kansoul | |
| 2009/0093837 A1 | 4/2009 | Dillon | |
| 2009/0125042 A1 | 5/2009 | Mouw | |
| 2009/0302089 A1 | 12/2009 | Harari et al. | |
| 2010/0130993 A1 | 5/2010 | Paz et al. | |
| 2011/0160752 A1 | 6/2011 | Aguirre | |
| 2011/0264121 A1 | 10/2011 | Liu | |
| 2016/0324523 A1* | 11/2016 | Lukin | ................. A61B 17/1114 |
| 2018/0271531 A1 | 9/2018 | Beisel et al. | |
| 2020/0268388 A1 | 8/2020 | Knapp et al. | |

FOREIGN PATENT DOCUMENTS

| | | | |
|---|---|---|---|
| CN | 104921772 A | 9/2015 | |
| CN | 105496484 A | 4/2016 | |
| CN | 107874801 A | 4/2018 | |
| CN | 109044439 A | 12/2018 | |
| CN | 111419315 A | 7/2020 | |
| CN | 112773440 A | 5/2021 | |
| CN | 113974742 A | 1/2022 | |
| CN | 110916740 B | 4/2022 | |
| EP | 2884907 A1 | 6/2015 | |
| EP | 3549534 A1 | 10/2019 | |
| WO | WO2010051909 A1 | 5/2010 | |
| WO | WO2012007042 A1 | 1/2012 | |
| WO | WO2012161627 A1 | 11/2012 | |
| WO | WO2013176993 A1 | 11/2013 | |
| WO | WO2014055193 A1 | 4/2014 | |
| WO | WO2018057613 A2 | 3/2018 | |
| WO | WO2020210727 A1 | 10/2020 | |
| WO | WO2022061117 A1 | 3/2022 | |
| WO | WO2022186747 A1 | 9/2022 | |
| WO | WO2022265724 A1 | 12/2022 | |

OTHER PUBLICATIONS

Nolan-Neylan. Drug Releae polymer triggered by ultrasound. Chemistry World. Mar. 2012. 2 pages.
Poly(N-isopropylacrylamide) Wikepedia. https://en.wikipedia.org/wiki/Poly(N-isopropylacrylamide) retrieved Apr. 2, 2024. 7 pages.
Prakasam et al., Biodegradable Materials and Metallic Implants—A Review. J Funct Biomater. Sep. 26, 2017;8(4):44. 15 pages.
Schmidt et al., Electromagnetic Activation of Shape Memory Polymer Networks Containing Magnetic Nanoparticles. Macromolecular Rapid Communications, 2006. 27(14), 1168-1172.
Walker et al., Radio-frequency actuated polymer-based phononic meta-materials for control of ultrasonic waves. NPG Asia materials, 2017, 9, e350. 8 pages.
International Search Report and Written Opinion mailed Apr. 13, 2022, Intl. Appl. No. PCT/EP2021/087431, 10 pages.

* cited by examiner

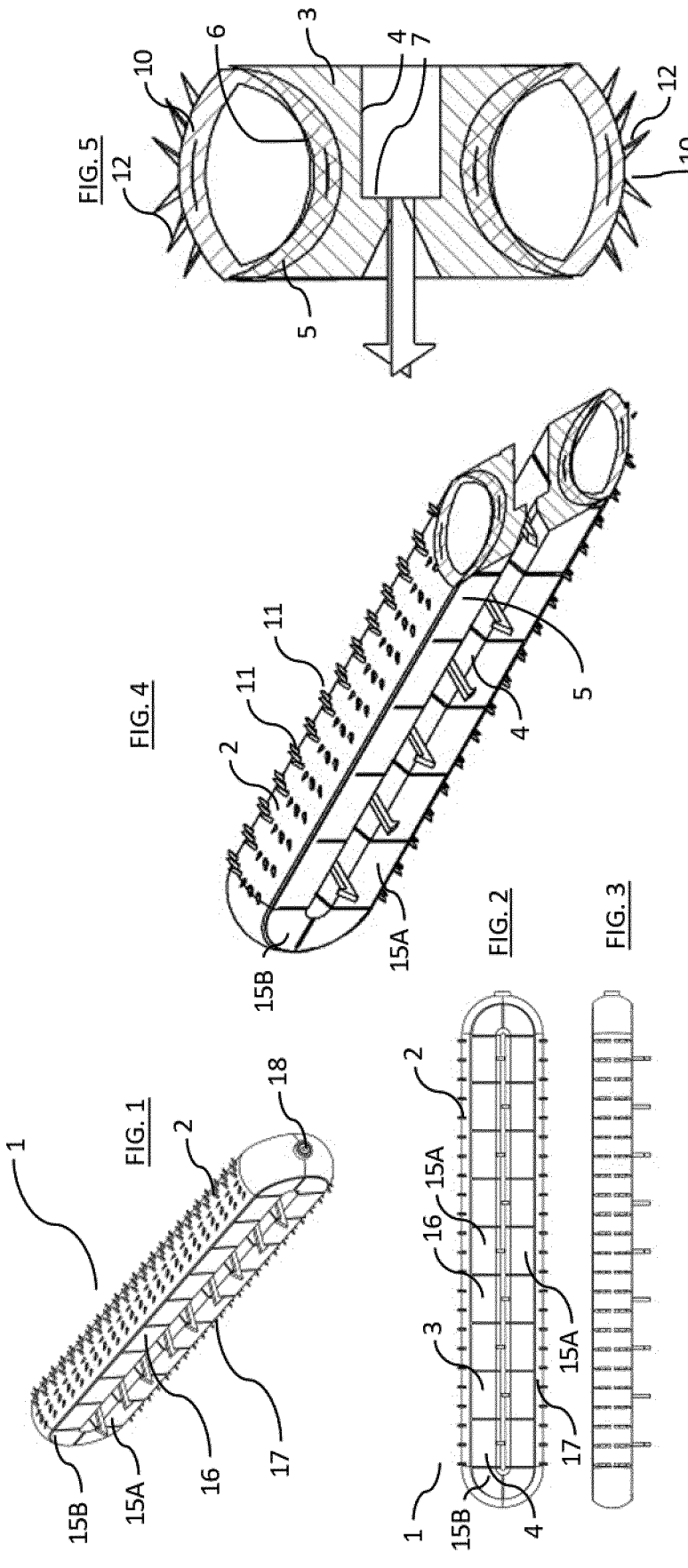

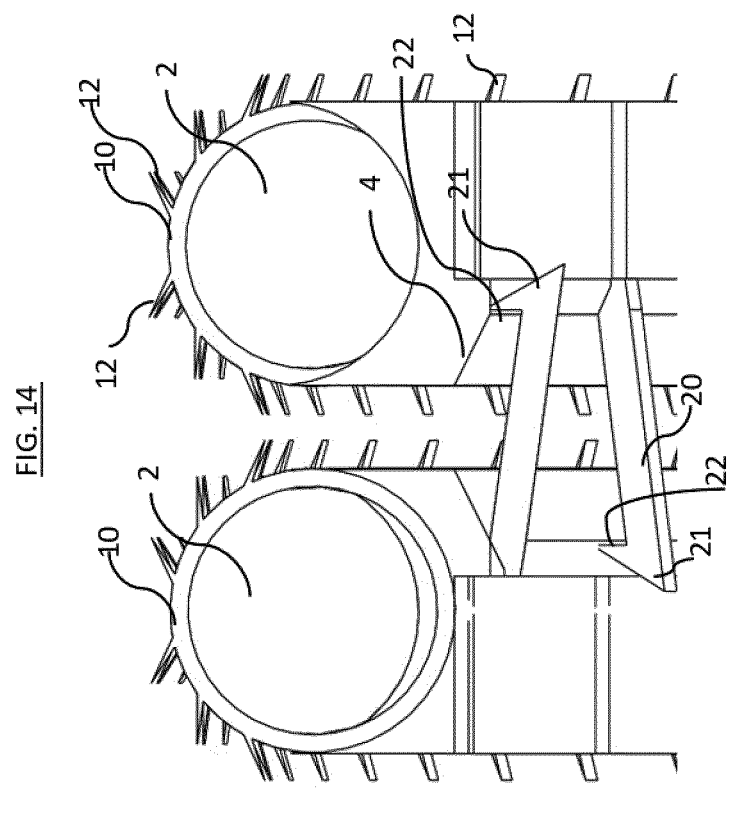
FIG. 14
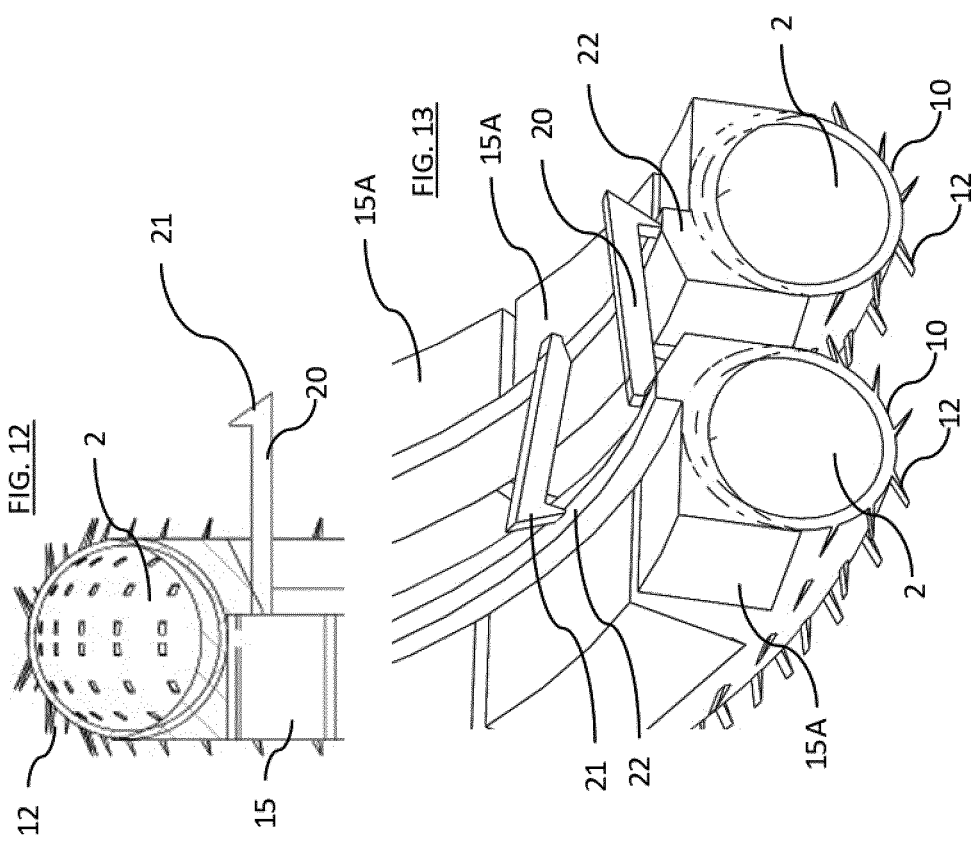
FIG. 12
FIG. 13

FIG. 36
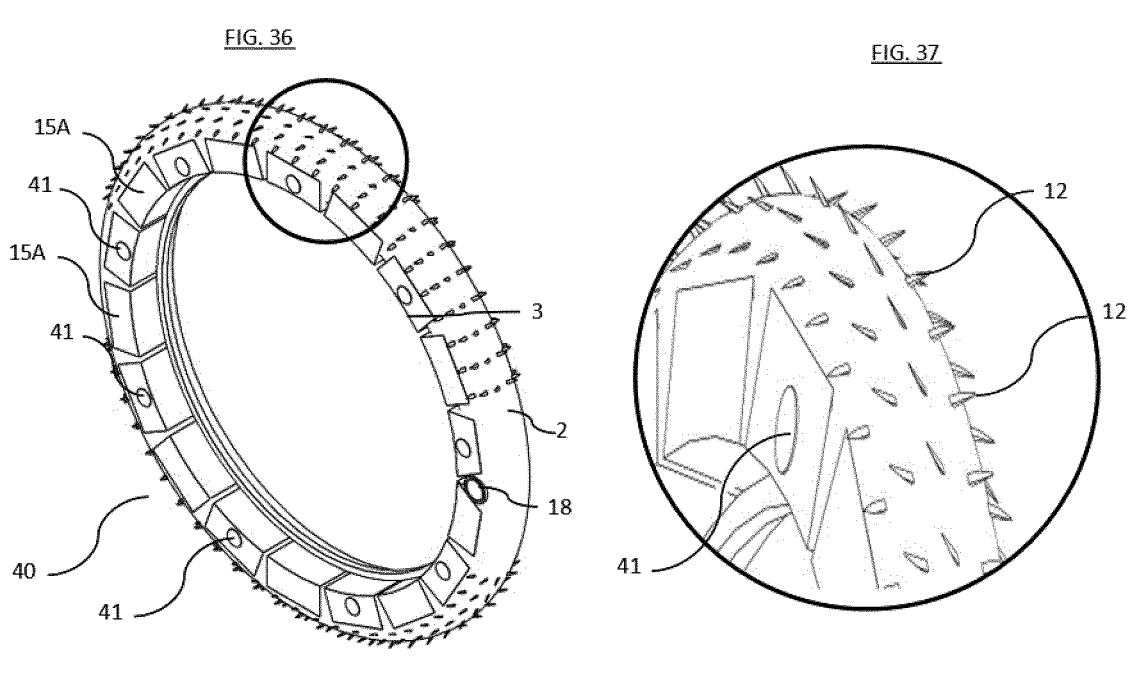
FIG. 37
FIG. 38
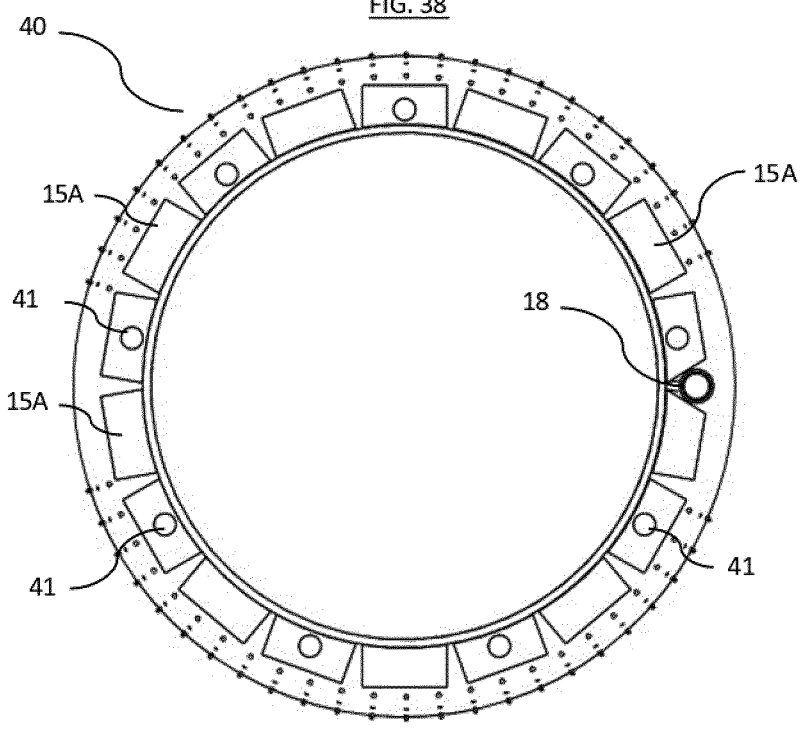
FIG. 39
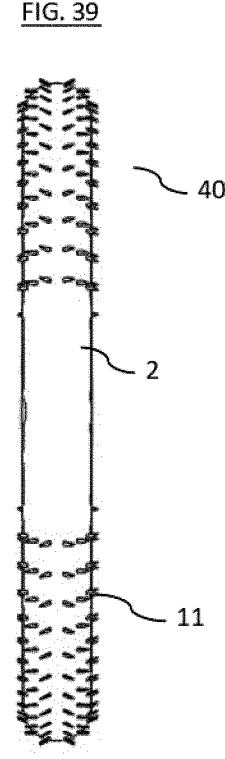

FIG. 40
FIG. 41
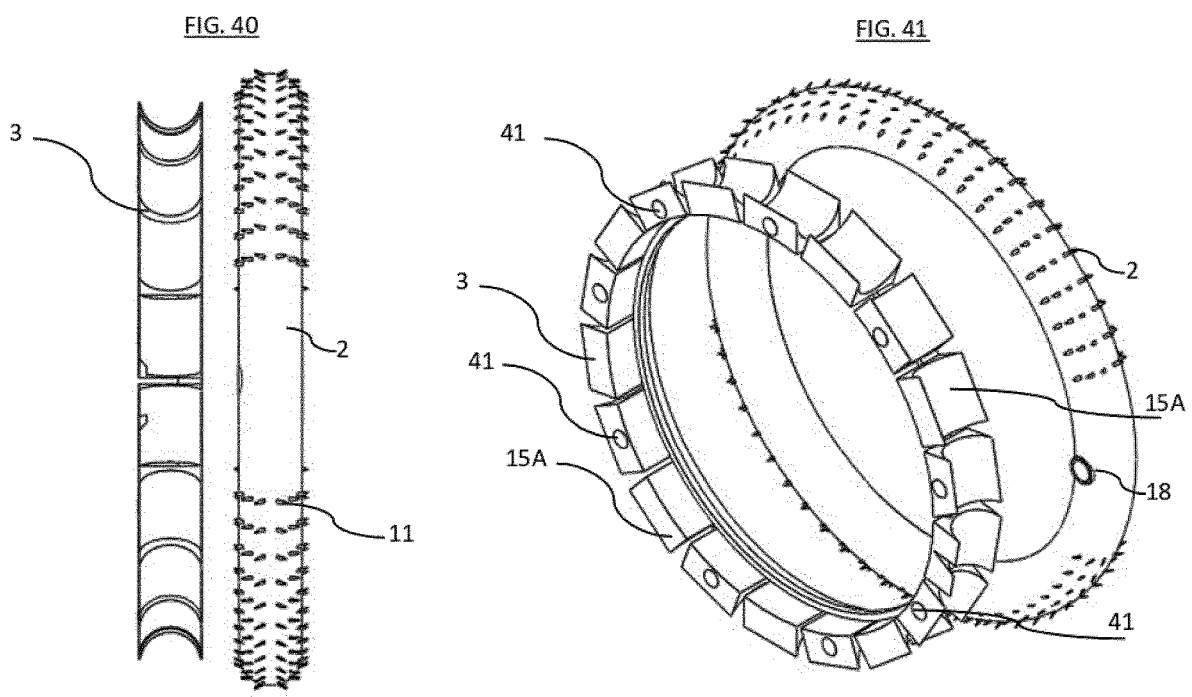
FIG. 42
FIG. 43
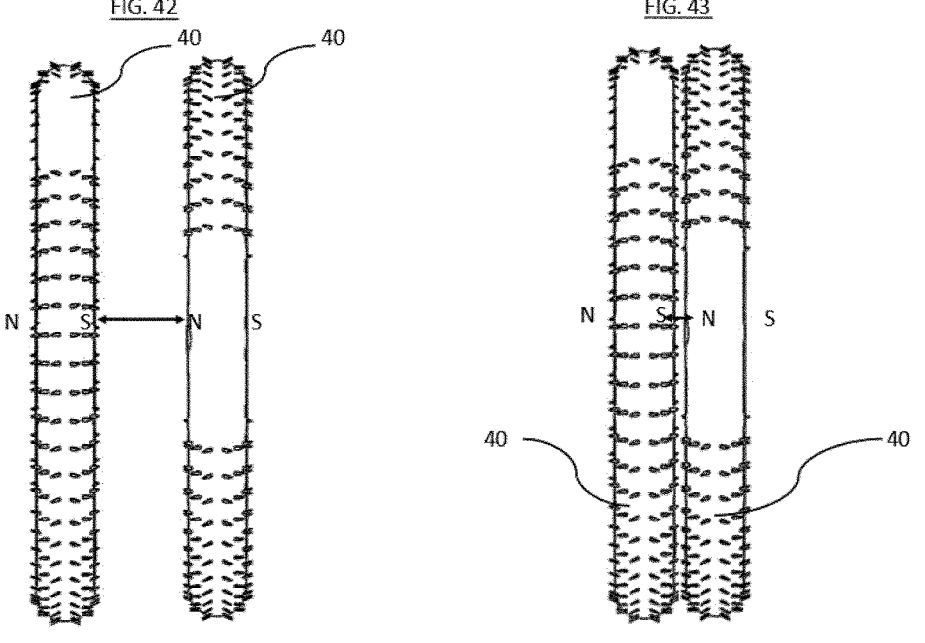

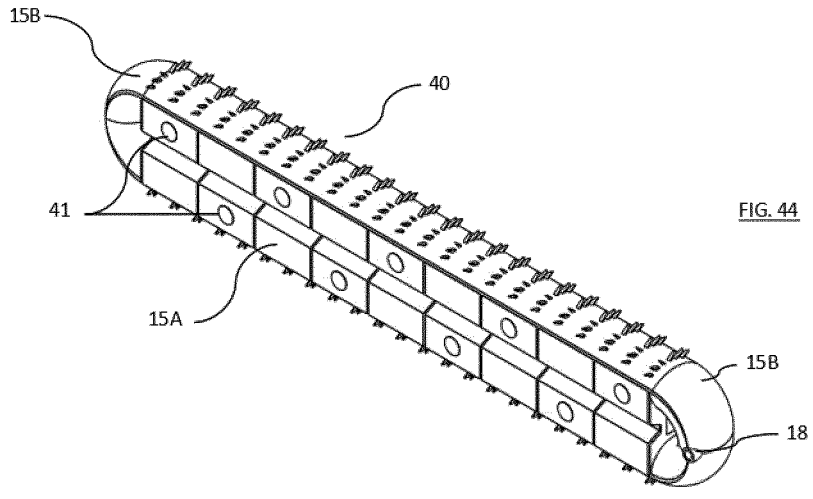
FIG. 44
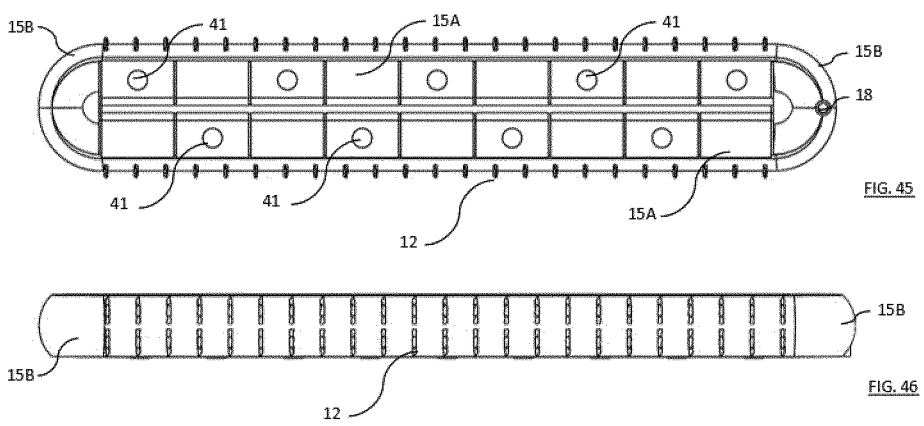
FIG. 45
FIG. 46
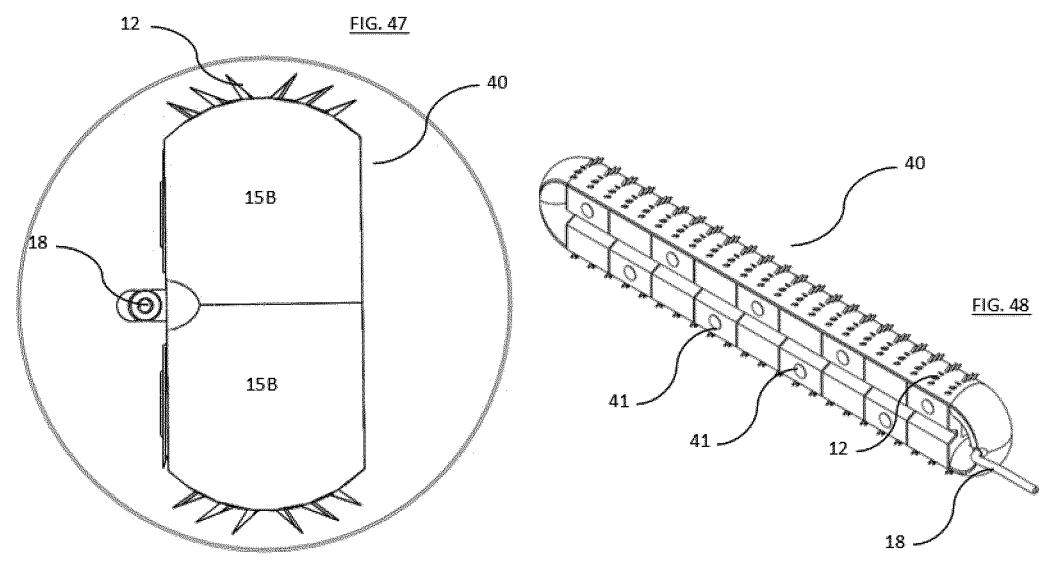
FIG. 47
FIG. 48

FIG. 52
50
53
53
53
51A
51B
52
51A
52
51B
53
52
53
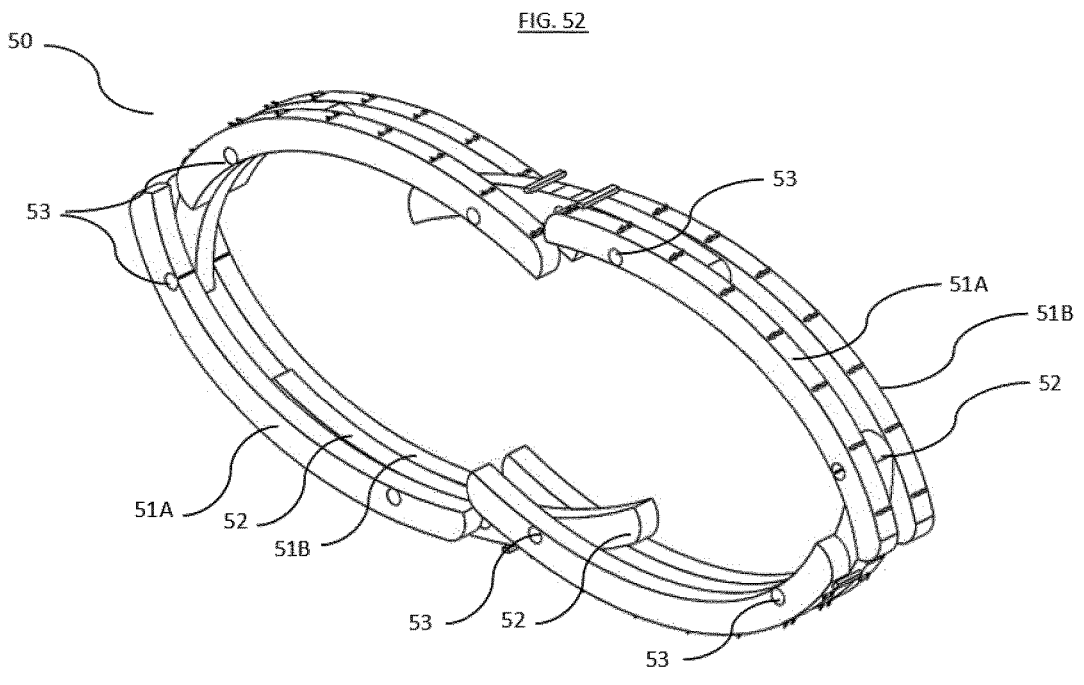
FIG. 53
51A
51B
50
53
53
FIG. 54
58
51B
51A
58
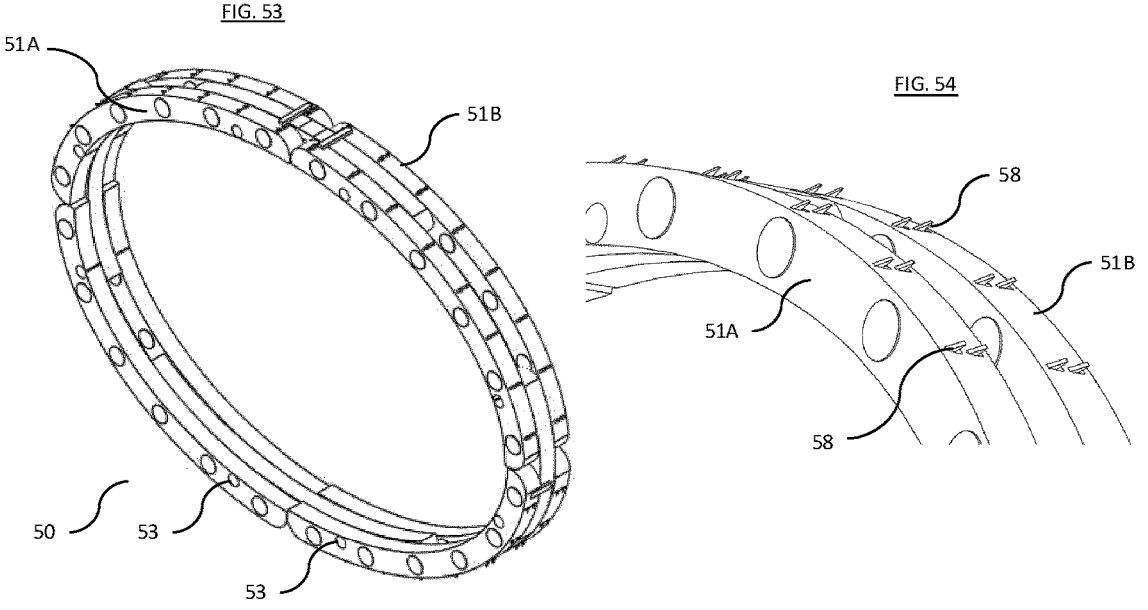

FIG. 61
FIG. 62
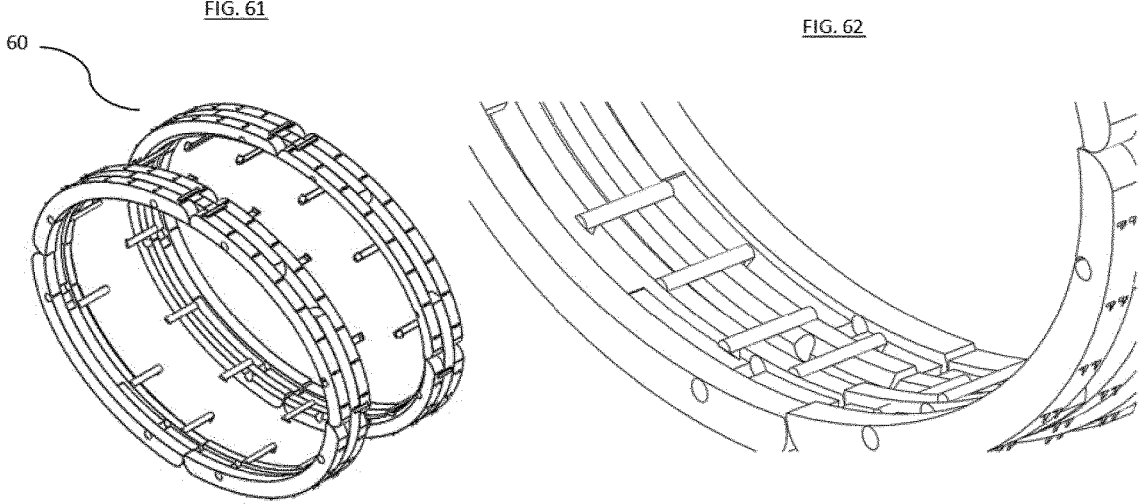
FIG. 63
FIG. 64
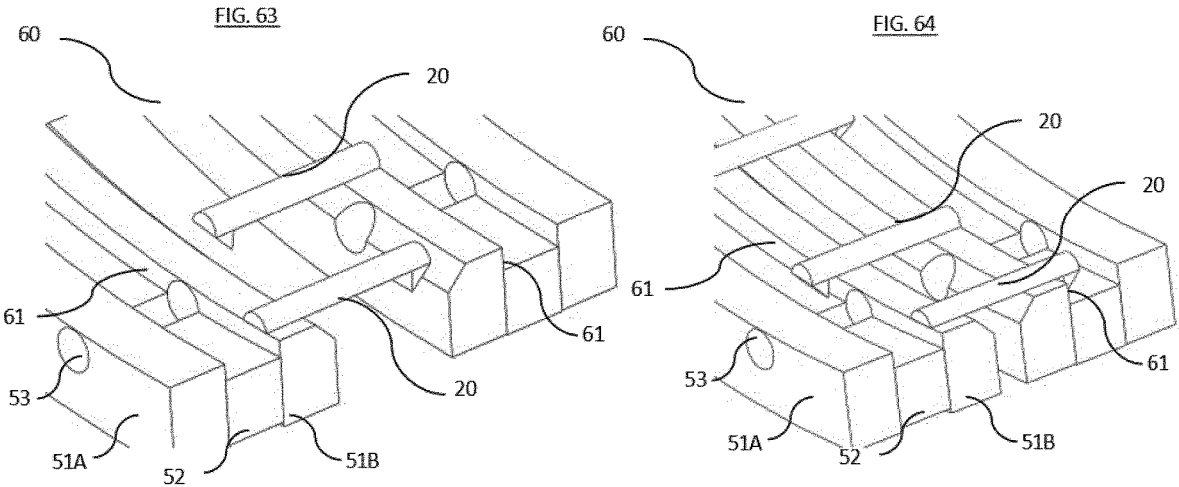

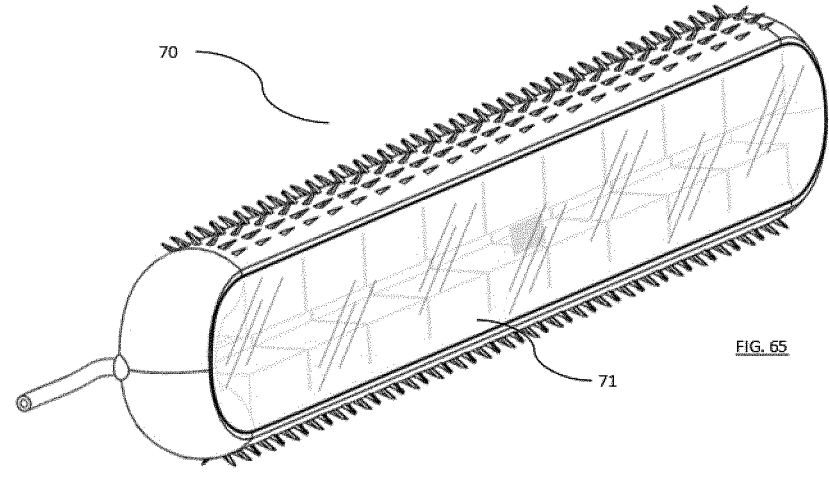
FIG. 65
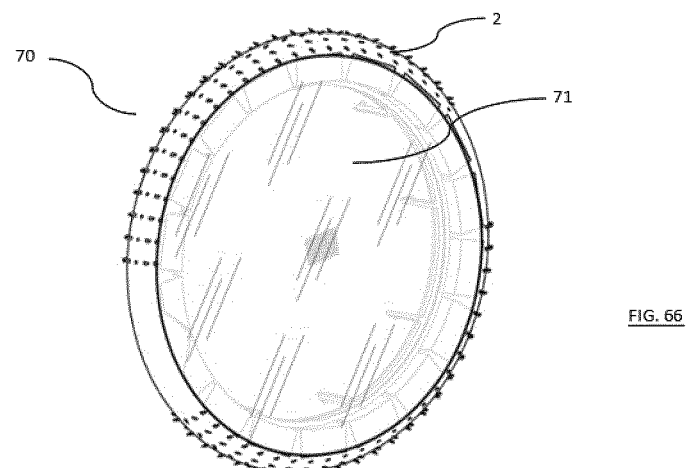
FIG. 66
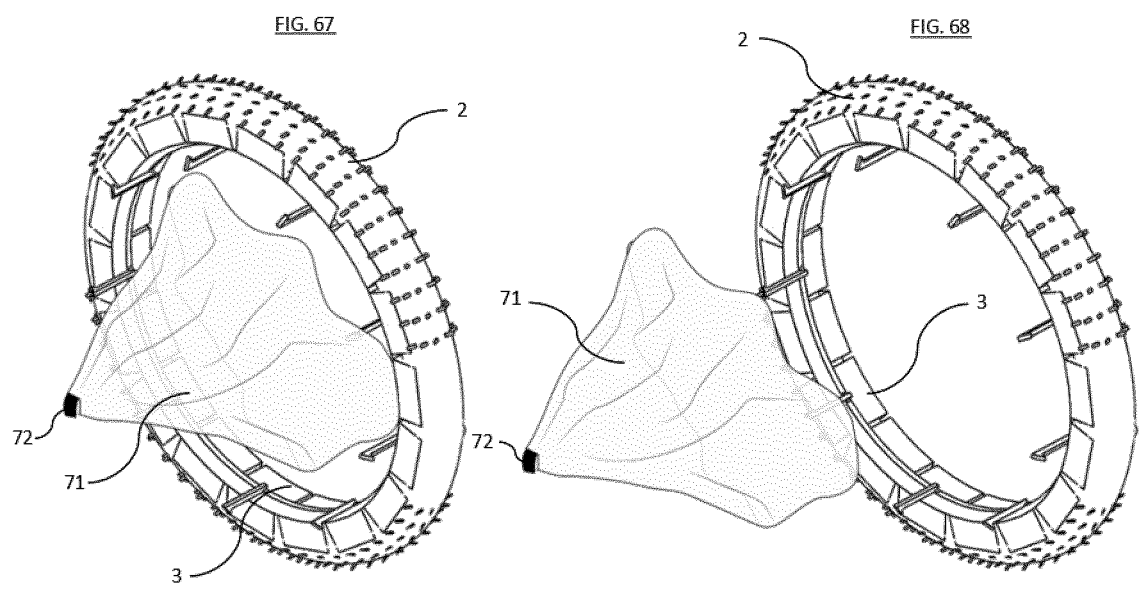
FIG. 67
FIG. 68

FIG. 83
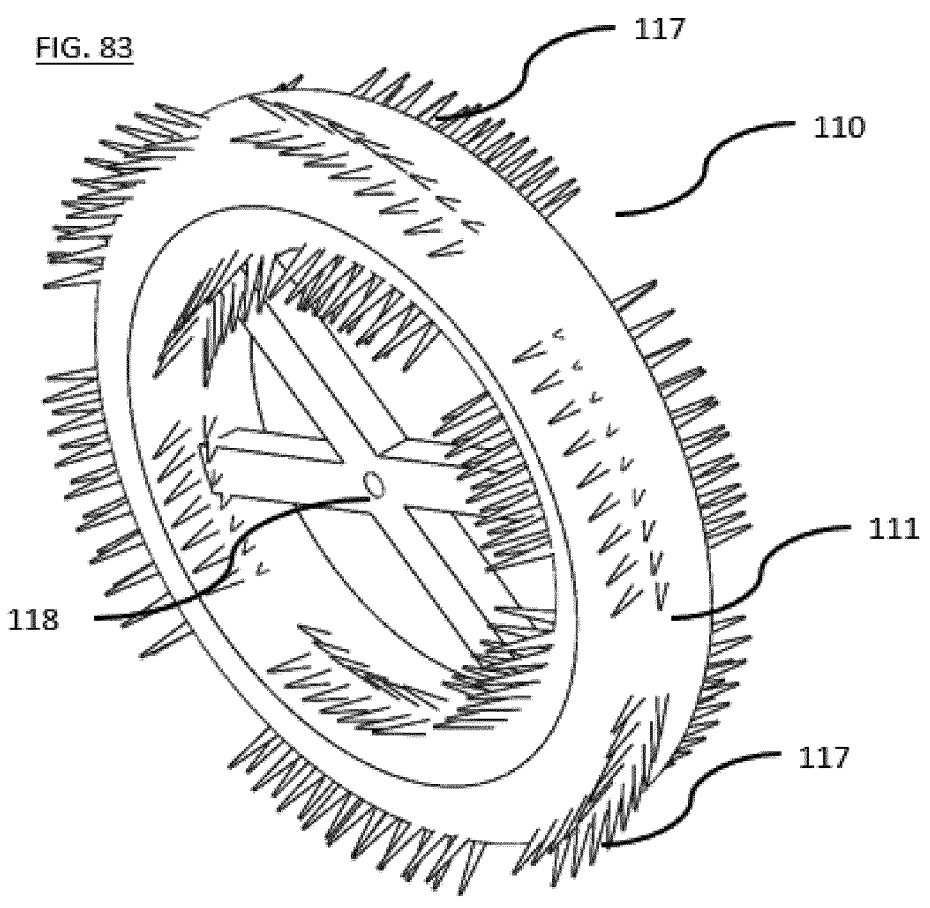
117
110
111
117
118
FIG. 84A
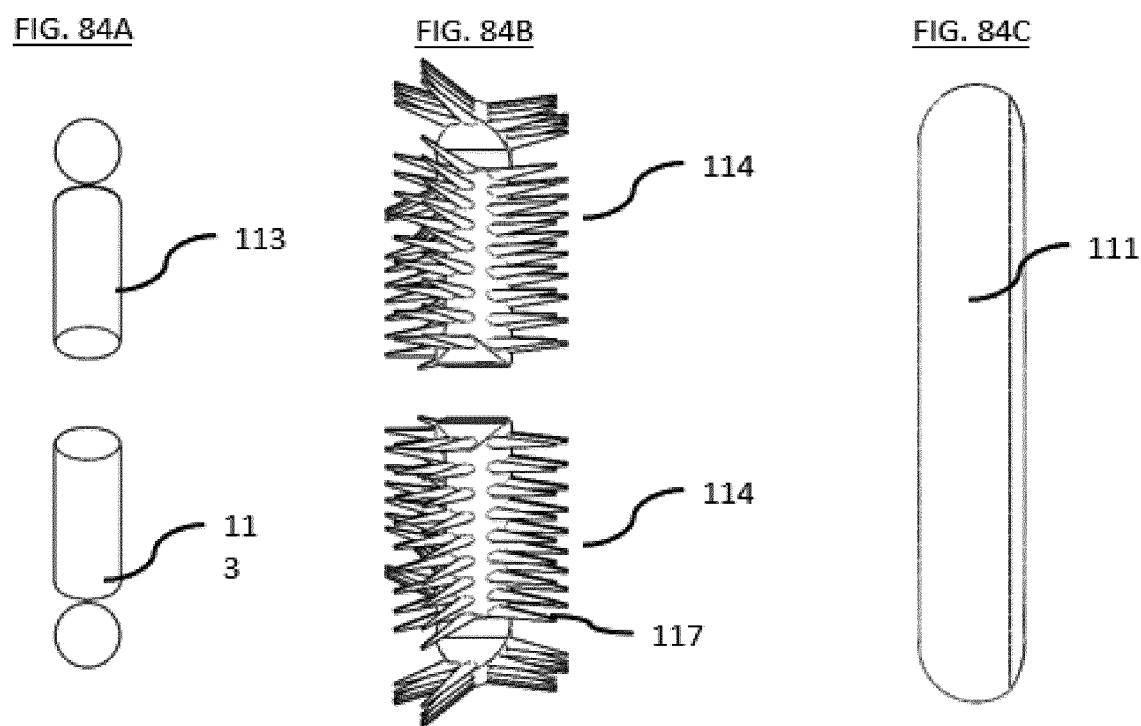
113
11
3
FIG. 84B
114
114
117
FIG. 84C
111

FIG. 87A
FIG. 87B
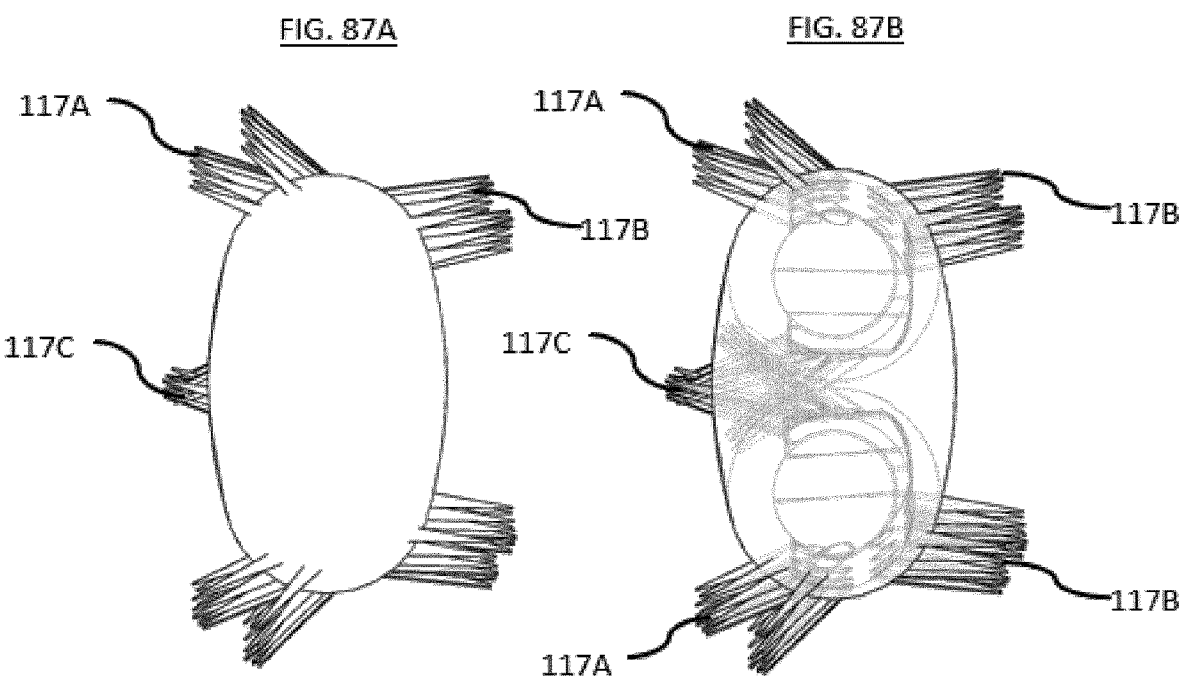
FIG. 88
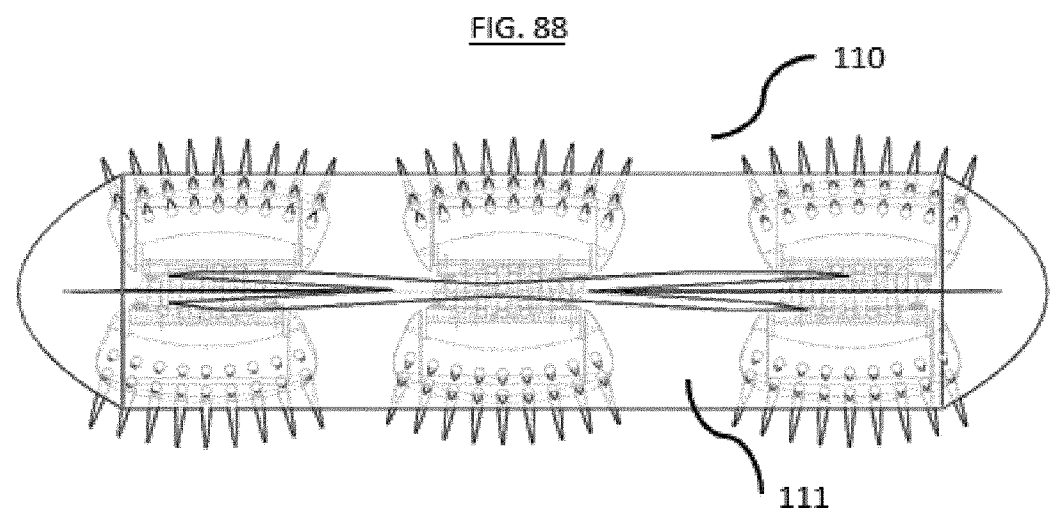

110B    110A 110B    110A

110B

121

122

122

122

121

122

122

121

122

122

122

FIG. 98
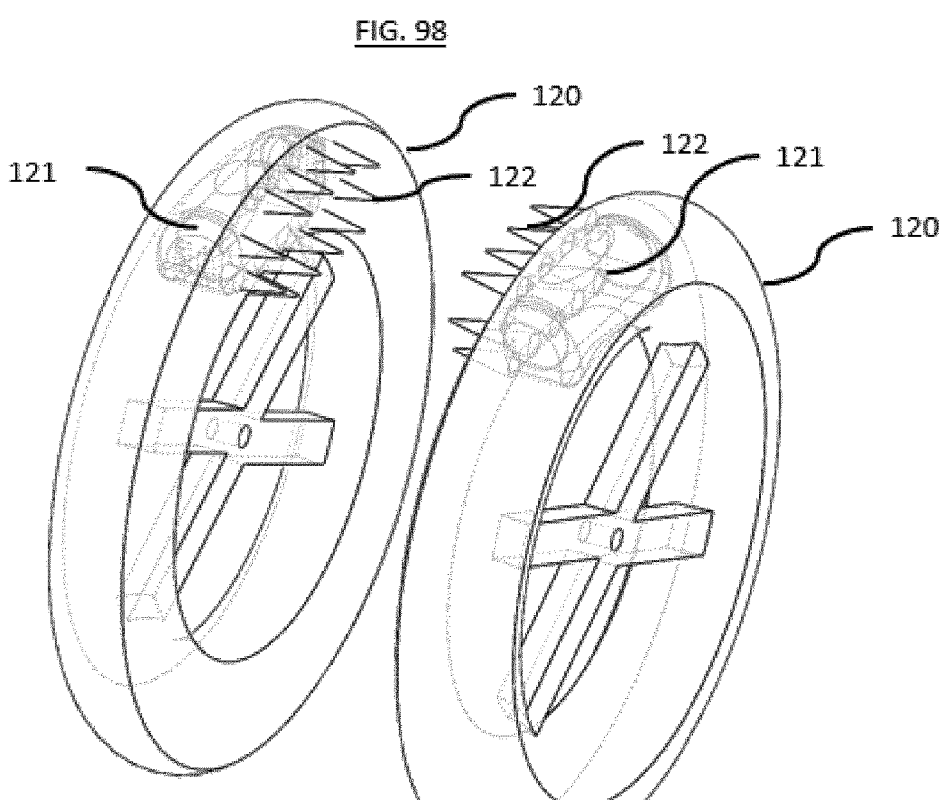
FIG. 99A                    FIG. 99B
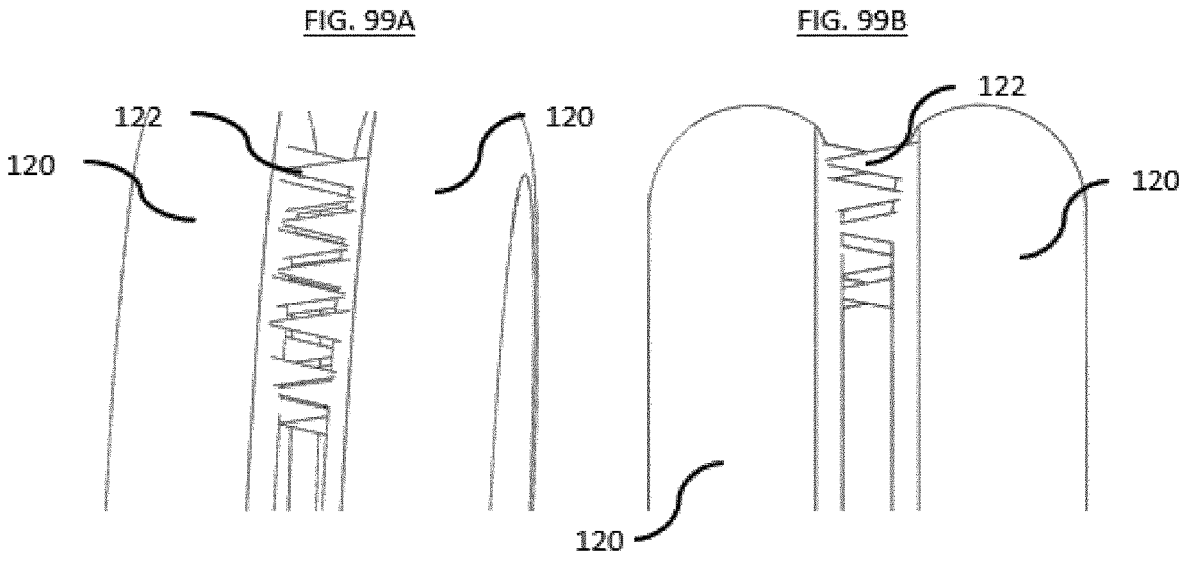

FIG. 102
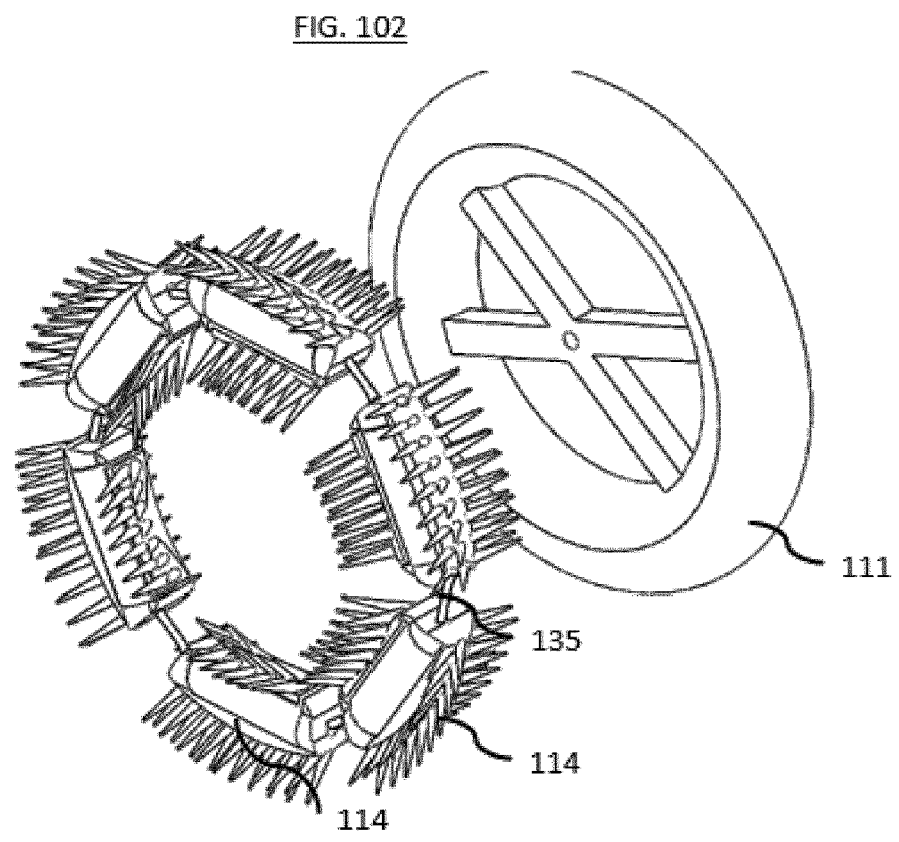
FIG. 103B
FIG. 103A
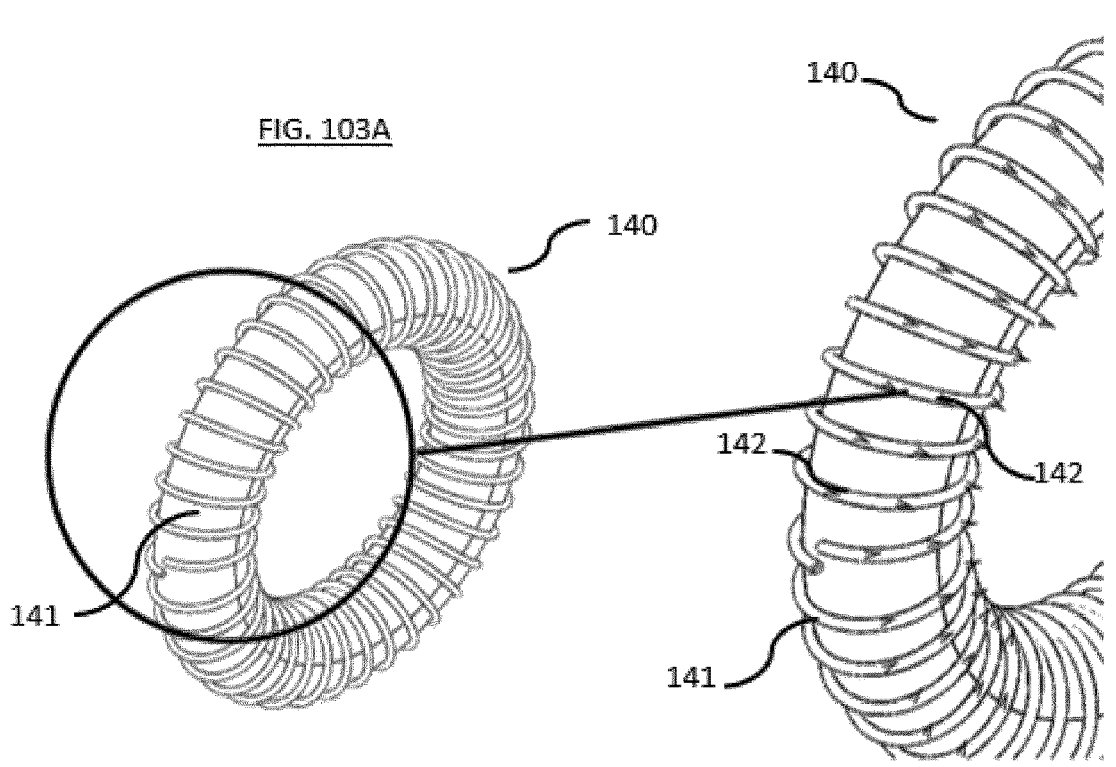

(A)

(B)

(C)

(D)

COMPRESSION ANASTOMOSIS SYSTEM, AND USE THEREOF

FIELD OF THE INVENTION

The present invention relates to a compression anastomosis system, particularly a compression anastomosis system for performing an anastomosis of the colon by minimally invasive surgery. The invention also provides a method of performing a compression anastomosis on a subject, in particular a method of performing an anastomosis of the colon by minimally invasive surgery.

BACKGROUND TO THE INVENTION

Colorectal cancer is the third most commonly occurring cancer in men and the second most commonly occurring cancer in women across the world. There were over 1.9 million new cases in 2020 globally. The global burden of colorectal cancer is expected to increase by 60%, to over 2.2 million new cases and 1.1 million annual deaths, by the year 2030. This growth is expected as a product of environmental changes, such as more sedentary lifestyle, greater obesity, processed food, alcohol, and meat consumption, and greater overall longevity.

A surgical anastomosis is done when a surgeon removes a diseased part of an intestine, colon or blood vessel and then reconnects the healthy ends. One of the most serious complications of anastomosis is anastomotic leakage which occurs in up to 20% of patients undergoing anterior resection. Anastomotic leakage causes faecal material to enter the bowel cavity leading to serious complications such as peritonitis or septic shock. An anastomotic leakage is not easily detectable and leads to extended hospital stays, readmission, reoperations or even death. In the UK, the 2019 National Bowel Cancer Audit showed that 8% of patients who underwent colorectal surgery had an unplanned return to theatre (URTT) with 50% of these occurring within the first 7 days post-operatively. Mortality in patients with URTT is 8% compared to 2% in those who do not return to theatre.

Creating a healthy and safe anastomosis requires adequate perfusion, freedom from tension at the anastomotic site, and absence of distal obstruction and mesenteric twisting. Currently the creation of a surgical anastomosis is mainly done using a sewing or stapling technique. A surgical anastomosis can be configured in numerous ways. These include end to end, side to side, side to end, and end to side. The stapling devices can be circular (used to perform end-to-end anastomoses) and linear stapling devices (used for side-to-side anastomoses). A literature review comparing hand-sewn with stapled anastomoses in colon and rectal surgery have not found statistical differences in the surgical outcomes between these two methods. Many surgeons base their decision of performing stapled or handsewn anastomosis on their personal preference and experience. Some colorectal surgeons consider that stapled anastomosis have advantages of lower complication rates and shorter operative times versus the hand sewn anastomosis. However, a high number of adverse events have been reported in relation to surgical staplers. The FDA found that it received more than 41,000 individual Medical Device Reports between 1 Jan. 2011 and 31 Mar. 2018 including 366 deaths, more than 9,000 serious injuries, and more than 32,000 malfunctions (https://www.fda.gov/medical-devices/letters-health-care-providers/safe-use-surgical-staplers-and-staples-letter-health-care-providers) Due to these adverse events, some surgeons prefer to perform hand sewn anastomoses.

Another technique for creating an anastomosis consists of compression anastomosis in which the bowel ends are kept together using a device applying a consistent compression force. This leads to tissue necrosis and a healing process which eventually joins the two bowel ends. Various compression anastomosis devices have been developed however they have not achieved a wide adoption in clinical practice. The main limitations of the compression anastomosis devices have been the fact that they are difficult to use (for e.g., needing a purse suturing to secure in place) and were designed for an open surgery while the surgery practice is moving towards minimally invasive techniques. Despite the limitations, compression anastomotic healing was associated with less foreign body reactions, scarring, and inflammation as compared with stapled anastomoses in a large animal model.

Laparoscopic surgery is a minimally invasive surgery that is performed using several small 0.5-1 cm incision ports. At each port, a tubular instrument called a trocar is used. The laparoscopic instruments are then passed through the trocars. Compared to traditional open surgery, patients often experience less pain, a shorter recovery, and less scarring with laparoscopic surgery. In the UK, 61% of patients had laparoscopic procedures in 2019, an increase from 48% in 2014. Endoscopes are also used widely in colorectal surgery for various applications from illumination, imaging of the interior of the body or to perform minimally invasive surgical procedures which can include air insufflation, irrigation, aspiration or gripping and cutting of tissue. To introduce the equipment required for the respective intervention, the endoscope has several channels.

US 20080015617 describes a compression anastomosis ring (CAR) assembly which comprises: a first portion which comprises: an anvil ring; and a second portion which comprises: a bottom ring positioned substantially parallel to and spaced apart from said anvil ring, said anvil ring and said bottom ring being adapted to be brought together in the presence of a closure force being applied thereacross. This device is not suitable for use in minimally invasive surgery.

US 20020082625 describes a surgical fastener for performing an anastomosis, comprising a pair of rings and projections on one ring configured to lock the rings together in a compression anastomosis arrangement where the device is configured for the projections to perforate the body lumen tissue. The device is not suitable for use in a minimally invasive procedure.

US 20180271531 describes self-opening magnetic compression anastomosis device comprising a pair of magnetic rings each of which is adjustable from a delivery configuration to a deployed ring configuration and the use of the device to perform side-to-side anastomosis.

Compression anastomosis devices are described in US2016/324523, U.S. Pat. No. 9,320,524, CN104921772 and CN107874801. None of the prior art documents describe compression anastomosis devices that are suitable for performing an end-to-end anastomosis of the colon by minimally invasive surgery.

It is an object of the invention to overcome at least one of the above-referenced problems.

SUMMARY OF THE INVENTION

The Applicant has addressed the problems of the prior art by providing a minimally invasive, biocompatible device for the creation of a compression anastomosis that can significantly reduce the anastomosis leakage. The device remains in place until the body's natural healing and tissue repair processes are complete. Once the device has been fully or partially resorbed, the device is spontaneously eliminated through the colon with the faecal bolus. The device is configured for use in any body lumen and is especially suitable for use in the gastrointestinal tract including the oesophagus, small intestine and large intestine (colon).

In a first aspect, the invention provides a compression anastomosis system comprising matching first and second compression ring devices, each compression ring device configured for adjustment from a contracted (e.g., elongated delivery) configuration suitable for passing through a lumen of a minimally invasive surgical instrument such as a trocar, catheter or endoscope to a deployed radially expanded configuration dimensioned to circumferentially abut an inner wall of a body lumen. At least one of the rings generally comprises coupling elements for coupling the rings together in a face-to-face compression anastomosis configuration. An additional coupling element may be employed that is configured to couple with the coupling elements of the rings. Each compression ring device typically comprises tissue anchors disposed on a radially outward facing surface of the ring and configured to anchor the ring to the wall of the body lumen when the ring is deployed in the body lumen. The anchors may be disposed on a top and/or side of the ring.

In a second related aspect, the invention provides a compression ring device configured for adjustment from a contracted (e.g., an elongated delivery) configuration suitable for passing through a lumen of a surgical instrument such as a trocar, catheter or endoscope to a deployed radially expanded configuration dimensioned to circumferentially abut an inner wall of a body lumen, in which the ring device comprises a coupling element for coupling the ring to a matching adjacent ring in a face-to-face compression anastomosis configuration, and in which the ring device typically comprises tissue anchors disposed on a radially outward facing surface of the ring and configured to anchor the ring to the wall of the body lumen when the ring is deployed in the body lumen. The anchors may be disposed on a top and/or side of the ring.

One or both of the rings, or a part or parts thereof, may be biodegradable to allow the or each ring be absorbed, break-up into smaller pieces or adapt an open-ring shape. In another embodiment, the or each ring is configured to lose rigidity over time in-vivo or in response to an external stimulus to make the ring more pliable and easier to travel through the body lumen.

In any embodiment, the or each ring comprises a locking mechanism for locking the ring in the deployed configuration.

In any embodiment, the locking mechanism is self-locking.

In any embodiment, the or each compression ring when in an elongated delivery configuration is dimensioned to pass through a lumen of a surgical instrument having a diameter of up to 15 mm.

In any embodiment, the device is fully or almost fully biodegradable.

In any embodiment, one or more parts of the device are biodegradable such that in use parts of the device biodegrade to break the device into small parts dimensioned for passage through the body lumen (e.g., colon and anus).

In any embodiment, first parts of the compression ring device are configured to biodegrade faster than second parts of the compression ring device such that in use the first parts of the device biodegrade to break the compression ring device into second parts dimensioned for passage through the intestine and anus. The first parts (or specific areas of the first parts) may be configured for radio frequency assisted thermal decomposition.

In any embodiment, the device is configured for adjustment of the orientation of the tissue anchors upon deployment of the compression ring device from a first orientation to a second tissue gripping orientation.

In any embodiment, the anchors are disposed on a top and/or side of the ring.

In any embodiment, the anchors are disposed on opposed sides of the ring.

In any embodiment, the anchor elements extend away from the ring surface radially or at an angle to a radial vector.

In any embodiment, the ring is configured such that upon deployment the angle of anchor elements relative to the longitudinal axis of the body lumen reduces or increases.

In any embodiment, the anchors on a proximal side of the outer surface of the ring are angled outwardly (i.e., towards an open end of the body lumen) and the anchors on a distal side of the outer surface of the ring are angled inwardly (away from the open end of the body lumen).

In any embodiment, the tissue anchors comprise a plurality of arrays (typically linear arrays) of anchors circumferentially spaced apart around the radially outward facing surface of the compression ring.

In any embodiment, one or more of the arrays of anchors comprises a plurality (e.g., 2, 3, 4 or more anchors) disposed laterally across the radially outward facing surface.

In any embodiment, the tissue anchors are barbs.

In any embodiment, the or each compression ring device comprises an inflatable ring configured to deploy the compression ring upon inflation.

In any embodiment, the inflatable ring is configured such that a radially outward surface of the inflatable ring changes profile upon deployment from a first profile to a more convex profile causing tissue anchors on the radially outward surface to invert the wall of the body lumen around a distal face of the ring. The distal face of the ring is the face that during use faces the matching compression ring. This feature helps ensure that the when the rings are coupled together that the inverted tissue on the respective rings are held in place in place in an abutting position.

In any embodiment, the or each compression ring device comprises an elongated inflation conduit that is ideally detachable from the inflatable ring.

In any embodiment, the or each compression ring device comprises a strengthening element coupled to the inflatable ring.

In any embodiment, the strengthening element is annular.

In any embodiment, the strengthening element is coupled to the inflatable ring along a radially inner circumference of the inflatable ring.

In any embodiment, the inflatable ring is moulded to the strengthening element.

In any embodiment, the strengthening element is coupled to the inflatable along a side (lateral) circumference of the inflatable balloon.

In any embodiment, the annular strengthening element comprises a radially inner base part and radially outwardly depending sidewalls that define an annular trough dimensioned to receive the inflatable balloon. See FIG. 40 for example.

In any embodiment, the trough has a concave cross-section. See FIG. 40 for example.

In any embodiment, the annular strengthening element comprises a plurality of substantially rigid segments pivotally linked together.

In any embodiment, the plurality of substantially rigid segments include a first set of rigid segments linked together to form first and sections of the ring that are adjustable from a straight configuration to a curved configuration, and a second set of rigid segments that are curved and configured to connect the ends of the first and second sections to form the ring.

In any embodiment, the strengthening element comprises an elongated strain limiting element (such as a wire, filament or thread) wrapped around at least a part of the inflatable ring configured to allow deployment of the ring while preventing or limiting expansion of the ring (i.e., preventing or limiting change in the cross-sectional area of the inflatable ring). The element may form a coil around the ring. The element may be embedded in the wall of the ring (for example, the ring may be moulded with the element in situ).

In any embodiment, the strengthening element comprises an annular strengthening element coupled to one, or two opposed, lateral faces of the inflatable ring.

In any embodiment, the inflatable ring has a circular, semi-circular or oval cross section.

In any embodiment, the inflatable ring in cross section has a flat inner base part and convex upper part.

In any embodiment, the wall of the inflatable ring forming the flat inner base part is thicker than the wall of the inflatable ring forming the convex upper part.

In any embodiment, the inflatable ring comprises a plurality of first parts separated by one or more weakened second parts. The weakened second part(s) may be structurally weakened or may comprise a material that is configured to biodegrade faster than the material of the first parts. The weakened second parts are positioned on the ring such that when they degrade it results in the separation of the ring into a plurality of first parts that are sufficiently small to pass along the intestine and out through the anus.

In any embodiment, the compression ring device is biased into elongated delivery configuration. This may be achieved by the design of the linkages between the segments making up the ring. When the ring comprises an inflatable ring, inflation of the ring biases the ring into the radially expanded deployed configuration.

In any embodiment, the first and/or second compression rings each comprise a plurality of rigid links hingedly coupled together to form an annulus.

In any embodiment, the rigid links comprise alternating first and second links hingedly coupled together end to end, in which the first link comprises two spaced-apart arms and the second link comprises a single middle arm, in which each end of the single middle arm is disposed in between the two spaced apart arms of an adjacent first link and hingedly connected to the two spaced apart arms by a hinge element such as a pin.

In any embodiment, the system comprises a deployment mechanism actuatable to adjust the compression ring from an elongated delivery configuration to a radially expanded deployed configuration.

In any embodiment, the compression ring in a deployed configuration has an oval shape.

In any embodiment, the compression ring in a deployed configuration has a circular shape.

In any embodiment, all or some of the tissue anchors are biodegradable. In this embodiment, the biodegradation of the anchors can allow the ring to be released and passed along the body lumen without the need for the ring to degrade.

In any embodiment, the compression ring comprises a brake mechanism configured to prevent further radial expansion of the compression ring once it has been deployed to its desired deployed configuration.

In any embodiment, the brake mechanism comprises a brake element disposed on the single arm and configured to abut one of the two spaced-apart arms when it has pivoted to a position that is aligned with the single arm.

In any embodiment, one of the spaced apart arms comprises a detent dimensioned to receive the brake element.

In any embodiment, the compression ring comprises a locking mechanism to lock the links in the desired deployed configuration. In any embodiment, the locking mechanism is a self-locking mechanism. In any embodiment, the locking mechanism comprises one or more formations on a sidewall of the middle arm and a corresponding formation on a sidewall of one the spaced apart arms, where the formations are configured to engage when the ring is fully deployed. In any embodiment, the formations are dimensioned for a friction-fit engagement.

In any embodiment, each ring comprises a coupling element for coupling the rings together in a compression anastomosis configuration.

In any embodiment, the or each coupling element is magnetic.

In any embodiment, each ring comprises a magnetic coupling element (one ring may have a magnetic coupling element of one polarity and the other ring may have a magnetic coupling element of an opposite polarity).

In any embodiment the coupling elements on the first and second rings are dimensioned to nest together. For example, one magnetic element may be convex and the other may be concave.

In any embodiment, the coupling element comprises a latch mechanism. One ring may include an axially extending arm and the second ring may include a formation (for example an annular lip) configured to receive the arm in a locking arrangement.

In an embodiment in which the or each ring comprises an annular strengthening element, the coupling element(s) may be disposed on the strengthening element.

In any embodiment, the or each ring comprises a detachable cover disposed on a proximal or distal face of the ring configured to prevent material in the body lumen pass through the ring when the ring is deployed. The cover may be a film material or a non-woven material or a mesh of material.

In any embodiment, the cover comprises a gripping element to allow the cover to be gripped and detached from the ring after deployment of the ring.

In any embodiment, the compression ring has a width of 1-10 mm, preferably 2-5 mm or 3-4 mm.

In any embodiment, the compression ring has a diameter of 20-80 mm, depending on the body lumen it is to be used with, or if used with a colon, the specific section of colon.

In any embodiment, the rings or parts thereof comprise a biodegradable material. Detailed of such materials are known to a person skilled in the art and include nature-based polymers such as chitosan, hyaluronic acid, collagen, fibrin and silk, or derivatives thereof, and synthetic polymers such as polyglycolic acid (PGA), polylactic acid (PLA), poly-beta-hydroxybutyrate (PHB), poly lactic acid co glycolic acid (PLGA), poly-ε-caprolactone (PCL), or a biodegradable polyether (polyethylene glycol, polypropylene glycol, polytetramethylene glycol, etc). Biodegradable polymers are described in Prakasam et al. (Biodegradable Materials and Metallic Implants—A Review, J Funct Biomater. 2017

December; 8(4): 44). Biodegradable polyethers are described in Kawaii et al (https://doi.org/10.1002/3527600035.bpol9012).

In any embodiment, the system of the invention includes one or more body lumen clamps. Typically, the clamps are passive clamps. In any embodiment, the clamp may comprise magnets configured to maintain a proximate anastomosis compression ring in the desired position in the body lumen during deployment.

In another aspect, the invention provides the use of the compression anastomosis system of the invention to perform a compression anastomosis of a body lumen of a subject.

In any embodiment, the compression anastomosis is an end-to-end compression anastomosis of the body lumen.

In any embodiment, the compression anastomosis is a compression anastomosis of the colon. Other suitable body lumens include vasculature and the urethra.

In any embodiment, the subject has a colorectal cancer and the compression anastomosis is performed after a section of the colon containing cancerous tissue or suspected cancerous tissue has been excised.

In any embodiment, the or each anastomosis ring comprises:

an annular hollow tube that is biased into a ring shape and resiliently deformable; and a plurality of ring segments disposed within the ring, wherein the anastomosis ring is configured to be resiliently deformed into an elongated delivery configuration suitable for passing through a tubular surgical instrument such as a trocar, catheter or endoscope and to self-deploy into a radially expanded configuration suitable to fully or at least partially circumferentially abut an inner wall of a body lumen upon release from the surgical instrument.

In any embodiment, one or more of the ring segments comprise a magnetic or magnetisable material to provide the coupling element for coupling two rings together.

In any embodiment, one side of the or each ring segment comprises a magnetic or magnetisable material of a first polarity and an opposite side of the ring segments comprises a magnetic or magnetisable material of a second polarity.

In any embodiment, the annular hollow tube comprises a resiliently deformable polymeric material.

In any embodiment, the annular hollow tube, or a part or parts thereof, is biodegradable.

In any embodiment, the annular hollow tube or a part or parts thereof comprises a material configured to lose rigidity over a period of time in-vivo. This allows the annular hollow tube, and the anastomosis ring, to lose its rigidity after a period in-vivo allowing it to be compressed in the body lumen to facilitate movement along the body lumen. In the case of the mammalian gastrointestinal tract, this allows the ring to be passed through the colon and anus.

In any embodiment, one or more of the ring segments comprise an inner core and an outer sheath.

In any embodiment, the inner core comprises the magnetic or magnetisable material.

In any embodiment, the outer sheath comprises the tissue anchors. In any embodiment, the tissue anchors and annular hollow tube are configured such that upon assembly of the anastomosis ring the tissue anchors project through the annual hollow tube to provide tissue anchors on the external surface of the ring.

In any embodiment, the tissue anchors comprise first anchors disposed on a distal side of an outer diameter (e.g., the rear side) of the ring. These anchors aid with inserting the ring into the lumen—they prevent the ring from falling backwards into the lumen.

In any embodiment, the tissue anchors comprise second anchors disposed on a proximal side of an outer diameter (e.g., the front side) of the ring. These anchors aid with preventing the ring from falling forwards in the lumen. The also add anchorage when connected to the other ring to grip the tissue and hold the rings in place. In any embodiment, the second anchors of one ring are configured to interdigitate with second anchors of a matching ring when the two rings couple together to form a compression anastomosis.

In any embodiment, the tissue anchors comprise third anchors disposed on a proximal side of an inner diameter of the ring. These anchors grip the inverted tissue, when connected with the other ring they are designed to grip the inverted tissue and stop it from escaping the grip of the ring when the device is under pressure.

In any embodiment, the outer sheath is configured to shield a magnetic force on one side of the inner core. This allows the side of the ring that faces a matching ring to have a greater magnetic force than an opposite side of the ring. This may be achieved, for example, by selectively shielding one side of the inner core. For example, the outer sheath may extend only partially around the inner core and, for example, cover one side of the inner core and not (or only partially cover) an opposite side of the inner core.

In any embodiment, the outer sheath is biodegradable.

In any embodiment, the or each inner core of the ring segments are cylindrical elements.

In any embodiment, the tissue anchors are biodegradable.

In any embodiment, the annular hollow tube comprises a central strut element configured to assist in the deployment of the tube into an O-shape, and fold when the annular hollow tube is compressed into a delivery configuration. In any embodiment, the central element is cross-shaped. In any embodiment, the central strut element is configured to fold when the ring is contracted delivery configuration.

In any embodiment, the anastomosis ring comprises a coil element helically wound around all or part of the ring. In any embodiment, the tissue anchors are disposed on the helical coil.

In any embodiment, the anastomosis ring comprises a sleeve wound around all or part of the ring. In any embodiment, the tissue anchors are disposed on the sleeve.

In any embodiment, the or each anastomosis ring is configured to be adjustable from an open ring formation and a closed ring formation. Thus, the ring may comprise a flexible elongated element (open ring) with opposed ends configured to couple together to form the closed ring. This allows the ring to be delivered through a laparoscopic medical device in an elongated configuration and the end coupled together to form a ring configuration in vivo.

In any embodiment, the flexible elongated element comprises a plurality of segments connected together. Adjacent segments may be hingedly connected together to allow adjustment of the ring between an open ring elongated configuration (delivery configuration) and a closed ring shape configuration (deployed configuration). In any embodiment, the ring comprises magnets and the flexible elongated element extends through the magnets.

In any embodiment, the flexible elongated element is biased into a ring shape. Thus, when it is released from a delivery device such as a laparoscopic instrument it forms a ring shape.

In any embodiment, the ring has a hollow lumen configured to accommodate an activation filament.

In any embodiment, the ring when deployed comprises an annular groove extending fully or partially around an inner circumference of the ring when deployed. This groove may function as a coupling element to couple matching rings together.

In any embodiment, the compression anastomosis system comprises a coupling insert configured to couple to the coupling elements of matching rings to couple the rings together.

In any embodiment, the coupling insert comprises a frame comprising first coupling formations configured to couple with connecting elements of a first ring and second coupling formations configured to couple with connecting elements of a second ring.

In any embodiment, the rings each comprise an annular groove extending fully or partially around an inner circumference of the ring when deployed, wherein the first coupling formations are configured to engage in the annular groove of one ring and the second coupling formations are configured to engage in the annual groove on the second ring, to hold the rings in a facing compression anastomosis configuration.

In any embodiment, the frame is radially expandable from a radially contracted delivery configuration to a radially expanded deployed configuration.

In any embodiment, the frame comprises a plurality of support parts disposed around a central axis, in which the coupling formations are disposed on the support parts, and a plurality of resiliently deformable struts connecting adjacent support parts, allowing movement of the support parts radially inwardly and radially outwardly relative to the central axis. The frame is resiliently biased into a delivery configuration in which the support parts are disposed around the central axis. The frame typically comprises four support parts equally spaced around a circumference of the frame when deployed. The or each support part comprises a support member comprising spaced apart coupling formations (one to couple to the coupling element of a first ring and one to couple to a support formation of a second ring). In any embodiment, the resiliently deformable struts each comprise curved struts. In any embodiment, each support part is connected to an adjacent support part by means of two resiliently deformable struts.

In any embodiment, all or part of the coupling insert is biodegradable.

In any embodiment, the or each ring comprises a material configured to change its structural properties in response to a stimulus so as to make the or each ring less rigid and suitable for passing along the body lumen.

In any embodiment, the stimulus is the environment of the body lumen, in which the material is configured to become less rigid over a period of time in the environment of the body lumen. For example, the material may be configured to change structural properties over a period of time as a result of the pH, temperature, or moisture content of the body lumen. The period of time may be, for example, 2 to weeks.

In any embodiment, the stimulus is an external stimulus such as an acoustic, electrical or electromagnetic stimulus.

In another aspect, the invention provides a method of performing a compression anastomosis of a body lumen in a subject, comprising the steps of:

providing first and second compression anastomosis rings that are each configured for adjustment from an elongated delivery configuration suitable for passing through a tubular surgical instrument such as a trocar, catheter or endoscope to a deployed radially expanded configuration dimensioned to circumferentially abut an inner wall of a body lumen;

inserting the first compression ring into the body lumen at a first position;
   inserting the second compression ring into the body lumen at a second position axially spaced apart from the first position;
   deploying the compression rings into a radially expanded deployed configuration so that each deployed ring circumferentially abuts an inner wall of the body lumen;
   excising a section of the body lumen between the first and second positions of the body lumen;
   coupling the first and second compression anastomosis rings together using coupling elements on each ring to form a compression anastomosis.

In any embodiment, the method employs a compression anastomosis system of the invention.

In any embodiment, the procedure is performed in-vivo by means of minimally invasive surgery.

In any embodiment, part of the body lumen is taken out of the body and the steps of the method are performed extra-corporeally.

In any embodiment, the body lumen is a gastrointestinal tract of a subject.

In any embodiment, the body lumen is a colon of a subject.

In any embodiment, the or each compression ring is inserted into the body lumen through an aperture in a sidewall of the body lumen.

In an embodiment in which the body lumen is the intestine (e.g., colon), the or each compression ring may be inserted through the rectum.

In any embodiment, the section of body lumen is excised after the compression rings have been inserted into the body lumen and deployed.

In any embodiment, the section of body lumen to be excised is clamped at each end with clamps prior to excision of the section of the body lumen.

In any embodiment, a section of body lumen is excised prior to insertion of the compression rings into the body lumen.

In any embodiment, the method comprises the steps of
   clamping the body lumen with a clamp at a first position;
   clamping the body lumen with a clamp at a second position spaced apart from the first position;
   cutting the body lumen at two spaced apart positions between the two clamps to excise a section of the body lumen;

In this embodiment, the excision of a section of the body lumen leaves an open end in the proximal part and distal part of the body lumen. A first compression ring is inserted into the open end of the distal part of the body lumen and a second compression ring is inserted into the open end of the proximal part of the body lumen.

In any embodiment, the method includes the steps of clamping the distal and proximal end of the excised section of body lumen with clamps preferably prior to excision of the section of body lumen.

In any embodiment, the method comprises the steps of
   advancing the first compression anastomosis ring in an elongated delivery configuration through a tubular surgical instrument to the body lumen in a minimally invasive manner;
   positioning the first compression anastomosis ring inside and laterally across the body lumen adjacent the first open end of the body lumen;

deploying the first compression anastomosis ring inside the body lumen so that the deployed ring circumferentially abuts an inner wall of the body lumen;

advancing the second compression anastomosis ring in an elongated delivery configuration through a tubular surgical instrument to the body lumen in a minimally invasive manner;

positioning the second compression anastomosis ring inside and laterally across the second open end of the body lumen;

deploying the second compression anastomosis ring inside the body lumen so that the deployed ring circumferentially abuts an inner wall of the body lumen; and coupling the first and second compression anastomosis rings together using the coupling elements to form a compression anastomosis.

In any embodiment, the method includes a step of positioning the compression anastomosis ring inside and laterally across the body lumen within 1-5 cm or 1-3 cm of the open end.

In any embodiment, the compression anastomosis ring is configured such that a radially outward surface of the ring changes profile upon deployment from a first profile to a more convex profile causing tissue anchors on the radially outward surface to invert the wall of the body lumen around a distal face of the ring (i.e., distal to the open end of the body lumen).

In any embodiment, the method includes a step of adjusting the orientation of tissue anchors provided on a body lumen facing surface of the ring during deployment of the ring.

In any embodiment, the method includes a step of adjusting the shape of the body lumen facing surface of the ring during deployment of the ring.

In any embodiment, the method includes a step of positioning the compression anastomosis ring inside and diagonally across the body lumen.

In any embodiment, the or each compression ring comprises an inflatable ring in which the deployment step comprises inflating the ring.

In any embodiment, the inflatable fluid is inflated using a fluid conduit fluidically connected to the ring, where the method includes a step of detaching the fluid conduit from the ring after deployment of the ring.

In any embodiment, the inflation fluid is a liquid, for example deionised water or saline.

In any embodiment, one or both of the rings is configured for adjustment from an open ring configuration to a closed ring configuration.

In any embodiment, one or both of the rings is delivered in an open ring configuration and adjusted to a closed ring configuration in vivo.

In any embodiment, the or each open ring is delivered through a minimally invasive medical device in an open elongated configuration, typically along an activation filament In any embodiment, the method comprises coupling ends of the or each ring together in vivo to form the closed ring(s).

In any embodiment, the or each ring is configured to self-adjust into a ring shape when released from a restraint such as a minimally invasive medical device In any embodiment, the ends of the or each ring is configured for self-coupling together. This may be achieved by for example the ends of the open ring having magnetic elements configured to guide the ends into a coupling relationship.

In any embodiment, the step of coupling the compression anastomosis rings together comprises providing a coupling insert, and coupling a first ring to the coupling insert and coupling the second ring to the coupling insert such that the two rings are coupled together to form a compression anastomosis.

In any embodiment, the method comprises advancing the coupling insert in a radially contracted delivery configuration through a minimally invasive medical device to the body lumen in a minimally invasive manner, deploying the coupling insert from the minimally invasive medical device into the body lumen whereby it expands radially into a coupling configuration, and connecting each ring to the coupling insert.

In any embodiment, the first ring is deployed inside a first cut end of the body lumen, the second ring is disposed inside a second cut end of the body lumen, the coupling insert is attached to the first ring inside the first cut end of the body lumen, and the second ring is then attached to the coupling inserts to bring the cut ends of the body lumen together to form the compression anastomosis.

Other aspects and preferred embodiments of the invention are defined and described in the other claims set out below.

BRIEF DESCRIPTION OF THE FIGURES

FIG. 1 is a perspective view of a compression ring device according to one embodiment of the invention and shown in an elongated delivery configuration;

FIG. 2 is a side elevational view of the compression ring device of FIG. 1;

FIG. 3 is a top elevational view of the compression ring device of FIG. 1;

FIG. 4 is a perspective partly sectional view of the compression ring device of FIG. 1;

FIG. 5 is a sectional end view of the compression ring device of FIG. 1;

FIG. 12 is a sectional view through the compression ring device showing a latch arm forming part of the coupling mechanism;

FIG. 13 is a partly sectional perspective view showing how the latch of one ring engages with a shoulder on the adjacent ring FIG. 14 is a sectional view illustrating the latch arms and coupling mechanism;

FIGS. 32 to 35 are side views showing the compression rings deployed in the end of the two sections of colon (FIG. 32), the rings being coupled together resulting in the tissue at the ends of the two sections being compressed together (FIG. 33), forming an anastomosis (FIG. 34), and the subsequent biodegrading of weakened sections of the rings allowing sections of the ring to be passed along the colon and discharged through the anus (FIG. 35).

FIG. 36 illustrates a compression ring device according to another embodiment of the invention and shown in a deployed radially expanded configuration;

FIG. 37 illustrates a detail of the compression ring device of FIG. 36;

FIGS. 38 and 39 are front and side elevational views of the compression ring device of FIG. 36;

FIG. 40 is a side elevational view of the compression ring device of FIG. 36 separated into the strengthening element and the inflatable balloon;

FIG. 41 a perspective view of the compression ring device of FIG. 36 separated into the strengthening element and the inflatable balloon;

FIG. 42 is a side elevational view of two compression ring devices in register and prior to engagement, and FIG. 43 is a side elevational view of the two rings after engagement;

FIG. 44 is a perspective view of the compression device of FIG. 36 in a delivery elongated configuration;

FIG. 45 is a side elevational view of the compression device of FIG. 44;

FIG. 46 is a top plan view of the compression device of FIG. 44;

FIG. 47 is an end elevational view of the compression device of FIG. 44 and including a balloon inflation fluid conduit;

FIG. 48 is a perspective view of the compression device of FIG. 44 and including a balloon inflation fluid conduit;

FIG. 52 is a perspective view of the compression ring device of FIG. 49 in a partially deployed radially expanded configuration;

FIG. 53 is a perspective view of the compression ring device of FIG. 49 in a fully deployed radially expanded configuration;

FIG. 54 is a detailed view of a body lumen facing surface of the compression ring device of FIG. 53 showing the tissue anchoring barbs.

FIG. 61 is a perspective view of two compression ring devices of FIG. 59 in register and prior to engagement, and FIG. 62 is a perspective view of the two rings after engagement;

FIG. 63 and FIG. 64 are detailed perspective views of two compression ring devices prior to and after coupling together;

FIG. 65 is a perspective view of another embodiment of a compression ring device of the invention having a face covering film and in an elongated delivery configuration;

FIG. 66 is a perspective view of the compression ring device of FIG. 65 in a deployed radially expanded configuration;

FIG. 67 and FIG. 68 are perspective views showing the detachment of the face covering film from the compression ring device of FIG. 65;

Figures 72, 73, 74, 75, 76:
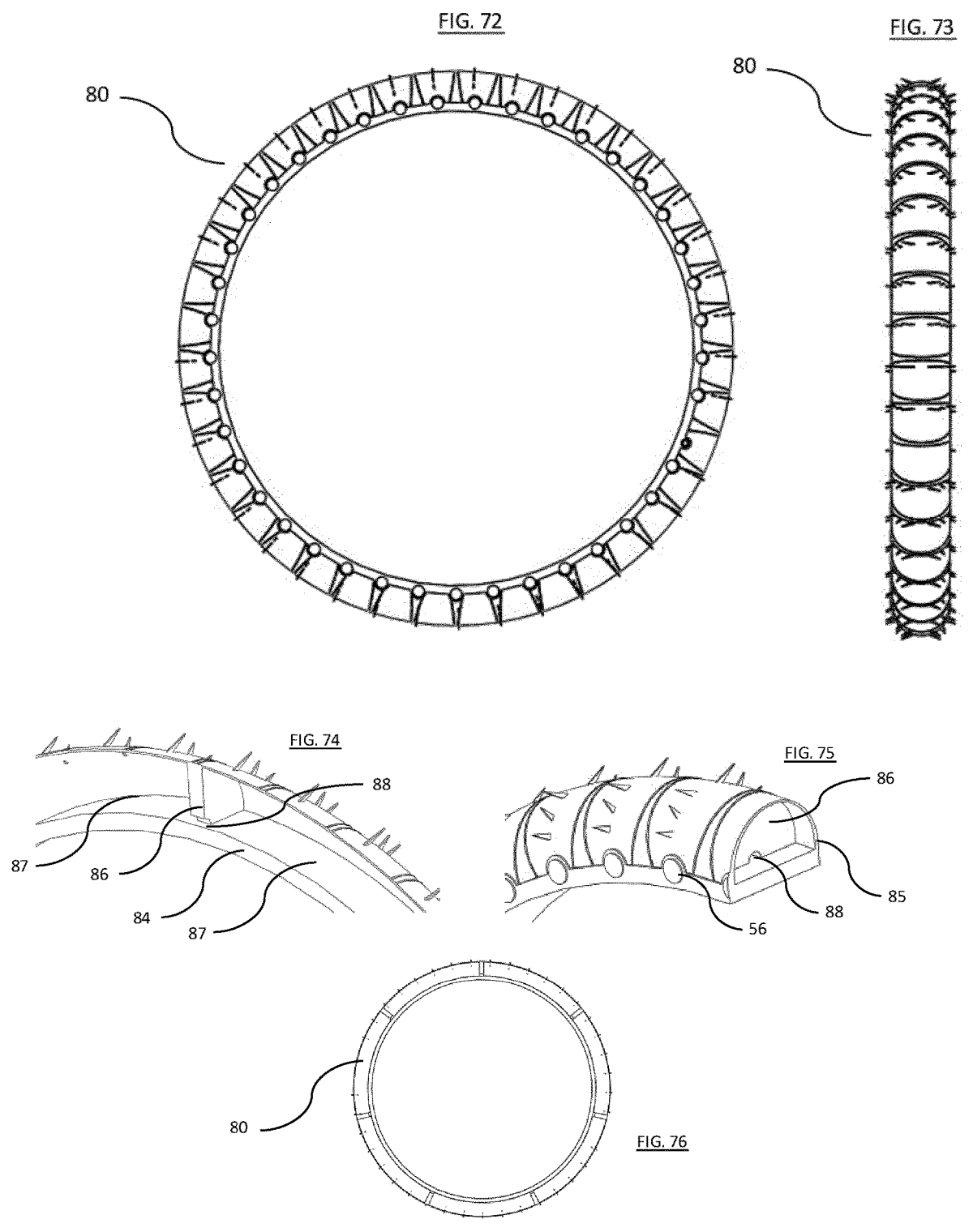

FIG. 72 and FIG. 73 are front and side elevational view of the compression ring device of FIG. 69;

FIG. 74 is a detailed longitudinal sectional view of the compression ring device of FIG. 69;

FIG. 75 is a transverse sectional view of the compression ring device of FIG. 69;

FIG. 76 is a side elevational view of the compression ring device of FIG. 69;

FIG. 83 illustrates a compression anastomosis ring according to an alternative embodiment of the invention.

FIG. 84A illustrates inner core magnetic elements forming part of the compression anastomosis ring of FIG. 83.

FIG. 84B illustrates outer sheaths forming part of the compression anastomosis ring of FIG. 83.

FIG. 84C illustrates the annular hollow tube forming part of the compression anastomosis ring of FIG. 83.

FIGS. 87A and 87B are end profile views of the compression anastomosis ring of FIG. 83.

FIG. 88 is a side elevational view of the compression anastomosis ring of FIG. 83 in a flat delivery configuration.

FIG. 98 is a perspective view of two compression anastomosis rings comprising the ring segments of FIG. 97.

FIGS. 99A and 99B are views of two compression anastomosis rings comprising the ring segments of FIG. 97 in a compression anastomosis forming configuration.

FIG. 102 is an exploded view of a compression anastomosis ring according to an alternative embodiment of the invention.

FIGS. 103A and 103B are exploded-views of a compression anastomosis ring according to an alternative embodiment of the invention.

DETAILED DESCRIPTION OF THE INVENTION

Figures 6, 7, 8, 9:
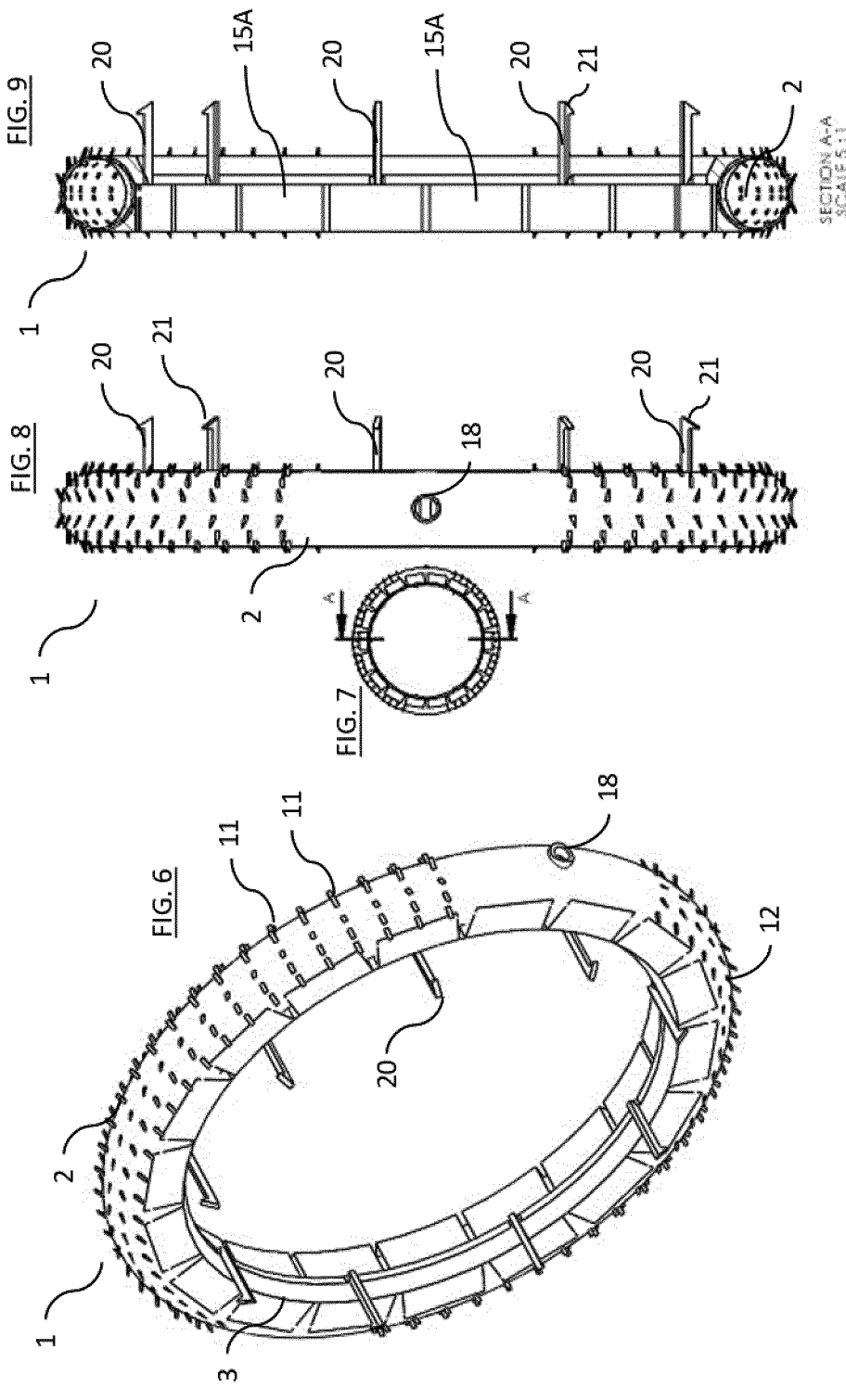
FIG. 6 is a perspective view of the compression ring device of FIG. 1 shown in a deployed radially expanded configuration.
FIG. 7 is a front elevational view of the compression ring device of FIG. 6.
FIG. 8 is a side elevational view of the compression ring device of FIG. 6.
FIG. 9 is a sectional view taken along the lines A-A of FIG. 7.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g., a feature, element, characteristic, property, method/process step or limitation) or group of integers (e.g., features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g., the administration of a PFA treatment to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g., the administration of a PFA treatment to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, kiang and zebra.

As used herein, the term "compression ring" is understood to mean a compression ring that can be used in creating a compression anastomosis. The ring generally has an external (body lumen facing) surface bearing tissue anchors such as spikes, hooks or barbs or surface texturing. The ring is generally adjustable from a contracted configuration (for example an elongated delivery configuration suitable for implantation in the body using a minimally invasive surgical tool) to a radially expanded configuration, which is typically dimensioned to have a diameter that is about the same or slightly greater or slightly less than the diameter of the body lumen in which it is deployed. The ring generally has a locking mechanism, preferably a self-locking mechanism, to lock the ring in the deployed configuration. The ring may be fully or partially biodegradable. The ring may include weakened sections (one or more) that are configured to degrade resulting in the break-up of the ring in the body lumen into smaller parts or to open the ring. The weakened section may be mechanically weak (e.g., a thin connecting element) or may be formed of a material configured to biodegrade faster than other parts of the ring. The compression ring may comprise an inflatable ring. The ring may be biased into the elongated delivery configuration. The ring may be formed of segments which may be connected together (e.g., hingedly connected together) or mounted on a connecting element such as a wire element. The segments may be unconnected.

The segments may be mounted in an annular tubular element which may be biodegradable. The segments may be magnetic. Each segment may be mounted in a sheath. The anchors may be provided on the sheath. The segments may be configured for piercing through the annular tubular element to present the tissue anchors on the surface of the ring. The ring may be adjustable from an open-ring configuration to a closed rig configuration. This allows the ring to be delivered in an open-ring configuration through a minimally invasive surgical instrument and then deployed into a closed ring configuration in-vivo. The ring may be configured to be biased into the closed ring configuration. The ring may comprise coupling elements configured to couple together to close the ring. The coupling element may be biodegradable. The ring may be configured to self-assemble into the closed ring configuration. The ring may comprise coupling elements configured to couple to coupling elements of an adjacent ring. The coupling elements may be configured to couple to a coupling insert.

"Material configured to change its structural properties in response to a stimulus so as to make the or each ring less rigid and suitable for passing along the body lumen" refers to a material that responds to a stimulus to lose its rigidity. The stimulus may be the environment of the body lumen. For example, when the body lumen is the gut, the material may be configured to become less rigid over a period of time as a result of an environmental cue such as pH, temperature or moisture. The material can be configured to become less rigid over a defined period of time, for example 2-10 weeks. The material may also be configured to change structural properties in response to an external stimulus, for example an acoustic (e.g., ultrasound), electrical (e.g., RF energy) or electromagnetic (laser, UV light) stimulus. The ring or part of the ring may be formed from the material. In any embodiment, the material is a polymer, for example a shape-set polymer or a temperature responsive polymer. An examples of a material configured to change its structural properties is a shape set polymer, for example crosslinked P(MMA-BA) copolymer (P=Poly, MMA=Methyl methacrylate, BA=Butyl Acrylate) which changes its shape in response to ultrasound (https://www.chemistryworld.cominews/druq-release-polymer-triqqered-by-ultrasound/4863.article). Another example is a temperature responsive polymer that can be actuated by RF energy to induce a change of state (e.g., Poly(N-isopropylacrylamide) (PNIPAm) (https://en.wikipedia.org/wiki/Poly(N-isopropylacrvlamide and Walker et al. (NPG Asia Materials, 9, e350(2017)). Another example is a polymer responsive to an electromagnetic field described in Schmidt et al (Macromolecular Rapid Communications, 2006).

"Coupling insert" means a coupling device configured to couple with coupling elements of a first ring and with coupling elements of a second ring such that the first and second rings when coupled to the coupling insert are brought together to form a compression anastomosis. The coupling insert is typically configured for delivery through a minimally invasive surgical instrument or medical device). The coupling insert, or a part or parts thereof, is generally biodegradable.

As used herein, the term "inflatable ring" refers to an annular balloon that can be inflated by forcing a fluid such as a liquid or a gas (or a mixture thereof) into the balloon resulting in the compression ring changing shape from the retracted (e.g., elongated delivery) configuration to a radially expanded deployed configuration. The inflatable ring may have an external (body lumen facing) surface that is configured to change profile upon deployment, for example to change from a first profile to a more convex profile.

As used herein, the term "biodegradable" as applied to a material or the ring means that the material can be fully or partially broken down in-vivo. Biodegradable materials that are suitable for making implants and for use in the body are described in the literature, and include nature based polymers such as chitosan, hyaluronic acid, collagen, fibrin and silk, or derivatives thereof, and synthetic polymers such as polyglycolic acid (PGA), polylactic acid (PLA), poly-beta-hydroxybutyrate (PHB), poly lactic acid co glycolic acid (PLGA), poly-ε-caprolactone (PCL), or a biodegradable polyether (polyethylene glycol, polypropylene glycol, polytetramethylene glycol, etc). Biodegradable polymers are described in Prakasam et al. (Biodegradable Materials and Metallic Implants—A Review, J Funct Biomater. 2017 December; 8(4): 44). Biodegradable polyethers are described in Kawaii et al (https://doi.org/10.1002/3527600035.bpol9012). A part or parts of the ring may be biodegradable. The term also encompasses materials configured to change properties (e.g., lose structural rigidity) as a result of environmental stimuli (e.g., the conditions in a body lumen) or as a result of an external stimulus such as an acoustic, electrical or electromagnetic (e.g., UV light or a laser) stimulus.

As used herein, the term "body lumen" is understood to mean an elongated cavity such as the gastrointestinal tract (for example the oesophagus, ileum, colon) or an artery, vein, lymph vessel, urethra, ureter, sinus, auditory canal, nasal cavity, bronchus.

As used herein, the term "minimally invasive surgical instrument" or "laparoscopic instrument" is understood to mean a surgical instrument that can be inserted into the body through a small incision and includes a lumen through which surgical tools or medical devices can be inserted. The lumen is generally up to 15 mm in diameter. Examples include catheters, trocars, endoscopes, and laparoscopic devices.

As used herein, the term "fluid" is understood to mean a gas, a liquid, or a mixture thereof. In a preferred embodiment, the fluid is a liquid, for example saline or deionised water.

As used herein, the term "detachable cover" is understood to mean a thin layer of material that covers a face of the compression ring. The material may be a film or a non-woven cloth material.

As used herein, the term "end-to-end anastomosis" is understood to mean an anastomosis formed between cut ends of a body lumen, for example cut ends of the colon. The system and methods of the invention may also be applied in side-to-end anastomoses or side-to-side anastomoses.

As used herein, the term "weakened section" is understood to mean a part of the ring that is mechanically weakened (e.g., a thin wall) or that is formed of a material that is configured to biodegrade fasted than the rest of the ring.

As used herein, the term "elongated strain limiting element" refers to a wire, thread or filament that is flexible and has the required tensile strength to constrain the shape of the inflatable ring to a desired configuration.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIGS. 1 to 9, there is illustrated a compression ring device according to the invention and indicated generally by the reference numeral 1. In FIGS. 1 to 5, the compression ring device 1 is shown in an elongated delivery configuration, suitable for delivery through a trocar having a diameter of 10 mm, and in FIGS. 6 to 9 the compression ring device is shown in a deployed radially expanded configuration. The compression ring device 1 comprises an inflatable ring 2 attached to an annular strengthening housing 3 for the inflatable ring. The housing 3 comprises a base 4 and sidewalls 5 depending from the base which together define an annular trough dimensioned to receive the inflatable ring 3. Referring to FIG. 5, a radially outward facing wall 6 of the base 4 has a concave profile and a radially inwardly facing wall 7 has a stepped profile.

An external face 10 of the inflatable ring 2 has a plurality of spaced-apart arrays 11 of tissue anchoring barbs 12 arranged circumferentially along the external face 10. Each array 11 comprises six barbs spaced across the external face 10 of the inflatable ring. As illustrated in FIG. 5, the external face of the inflatable ring is convex is shape, and three of the barbs 12 on a proximal side of the external face of the ring are angled outwardly (i.e., towards one end of the body lumen) and the three barbs on a distal side of the external face 10 of the ring are angled inwardly (towards an opposite end of the body lumen). In this embodiment, the barbs are integrally formed with the inflatable balloon and may be formed from the same polymer as the inflatable ring. The inflatable ring 2 also has a fluid port 18 configured for detachable engagement with an inflation conduit.

In more detail and referring to FIG. 2, the housing 3 comprises a plurality of substantially rigid segments hingedly linked together end to end, including a first set of rigid segments 15A linked together to form a first section 16 and second section 17 of the ring that are adjustable from a straight configuration to a curved configuration, and a second set of rigid segments 15B that are curved and configured to connect the ends of the first and second sections to form the annular housing 3. Thus, the housing is adjustable from an elongated configuration shown in FIG. 2 to a circular radially deployed configuration shown in FIG. 6.

Figure 11:
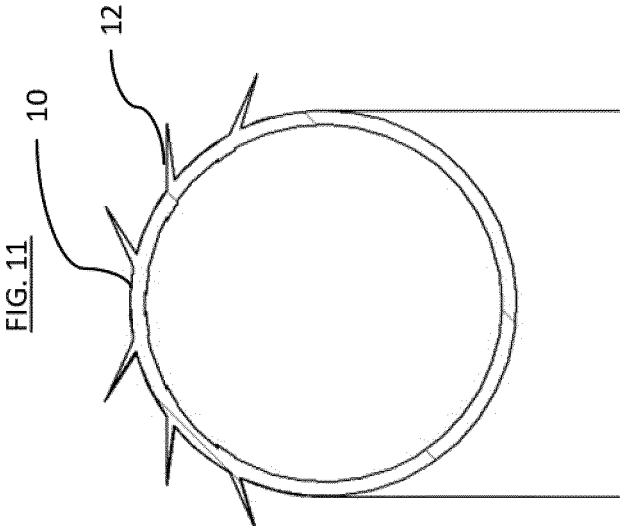
FIG. 11 is a sectional view through the compression ring device when the ring is in the deployed radially expanded configuration.
Figure 10:
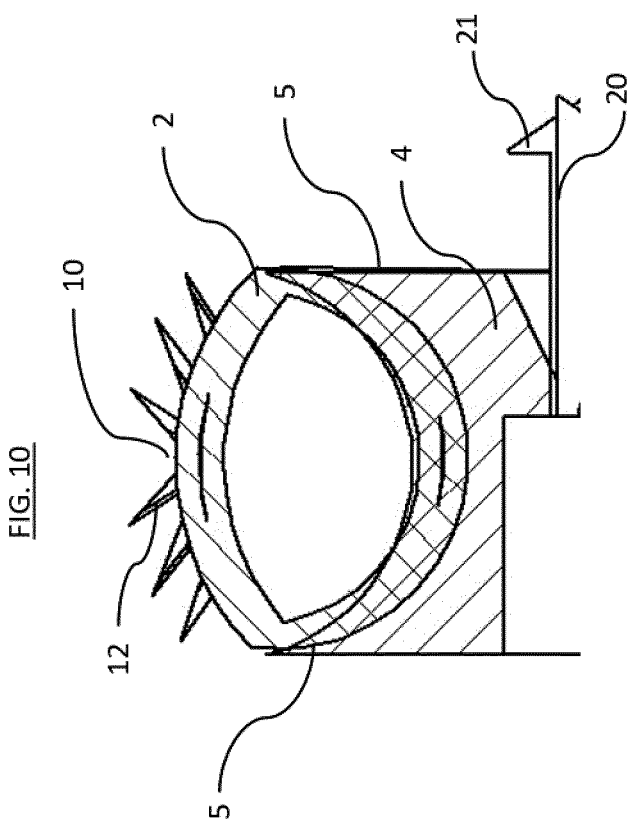
FIG. 10 is a sectional view through the compression ring device when the ring is in the delivery configuration.
Figures 15, 16:
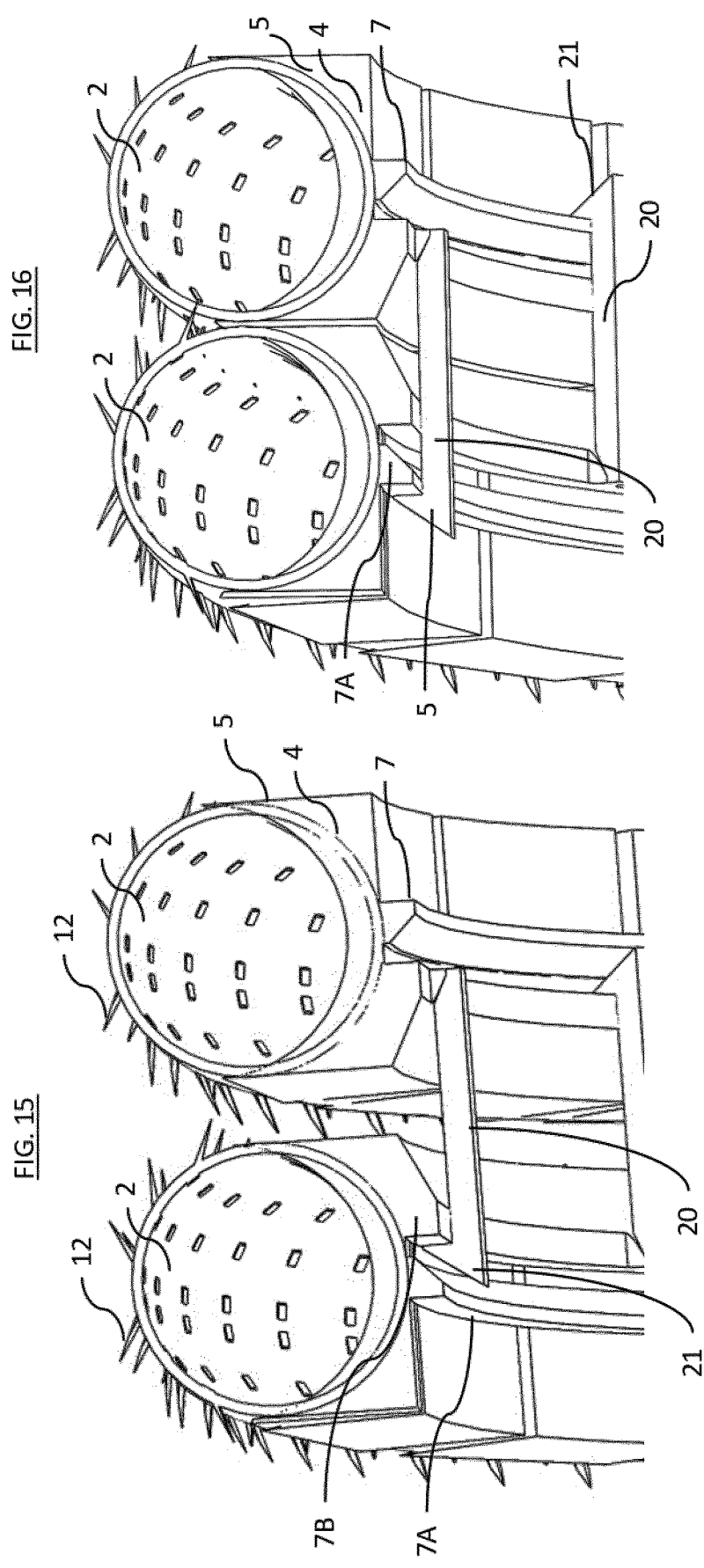
FIG. 15 and FIG. 16 are sectional views showing how the coupling mechanism may allow the rings to be coupled together in a slightly spaced-apart configuration (FIG. 15) and in an abutting configuration (FIG. 16)

Referring to FIGS. 10 and 11, the inflatable ring 2 is shown in cross-section before inflation (FIG. 10) and after inflation (FIG. 11). It can be seen that the inflatable ring is designed to change the shape of the external surface 10 and orientation of the barbs when inflated; the external surface 10 becomes more convex which causes the orientation of the barbs to change, causing the barbs to grip tissue of the body lumen and invert tissue around the top and side of the inflatable ring.

Referring to FIGS. 12 to 16, coupling elements for coupling two rings together in register are illustrated and comprise a series of latching arms 20 attached to a side of the housing 3 and extending axially away from the housing. Each latching arm 20 has an angled head 21. The radially inner facing wall 7 of the base of the housing has a stepped profile with a step 22. In use, when two compression rings are positioned in register and brought together the angled heads 21 of the arms 20 catch the step to lock the rings together. Each compression ring may include a plurality of latching arms and a step as illustrated in FIGS. 12 to 14. In the embodiment shown in FIGS. 15 and 16, the wall 7 of each ring has two steps 7A and 7B allowing the rings to be locked together in a slightly spaced-apart configuration or an abutting configuration.

Figure 17A:
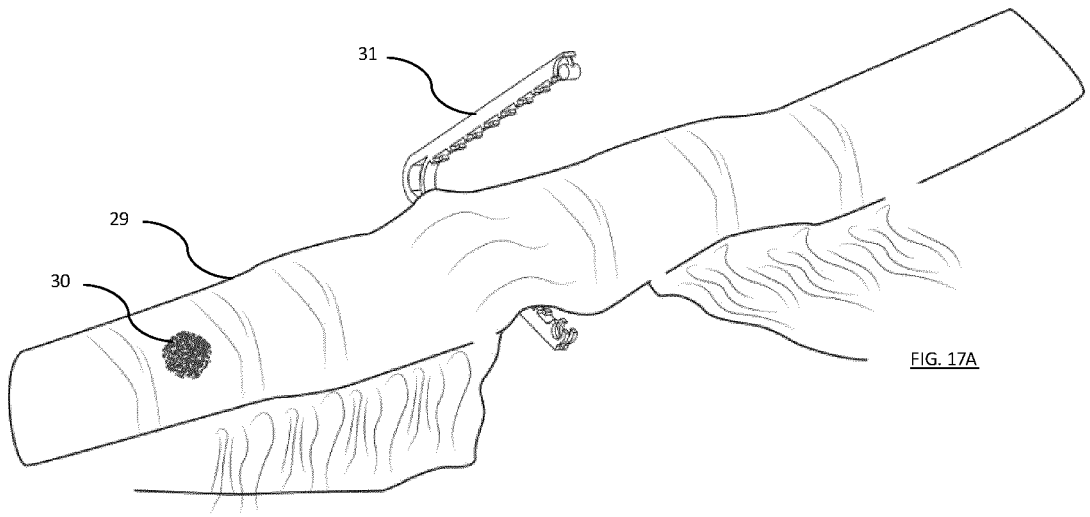
FIG. 17A illustrates a section of colon with tumour and a passive clamp being attached to the colon distally of the tumour.
Figure 18:
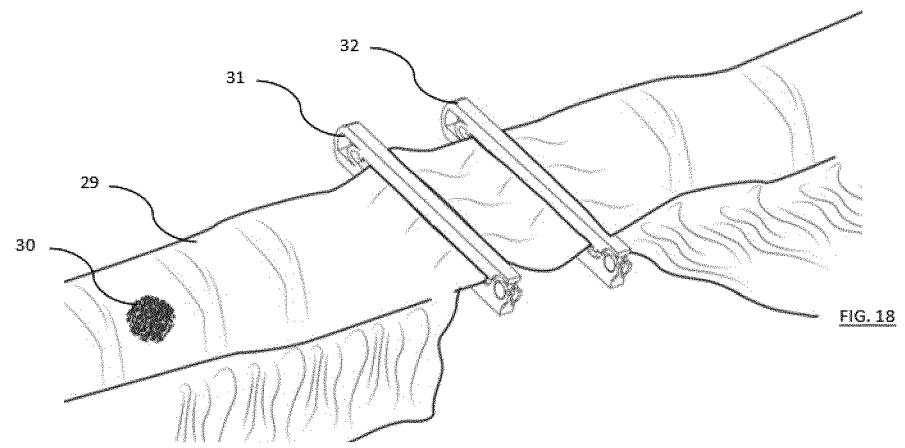
FIG. 18 illustrates a second passive clamp being attached to the colon distally of the tumour and spaced apart from the first clamp
Figure 17B:
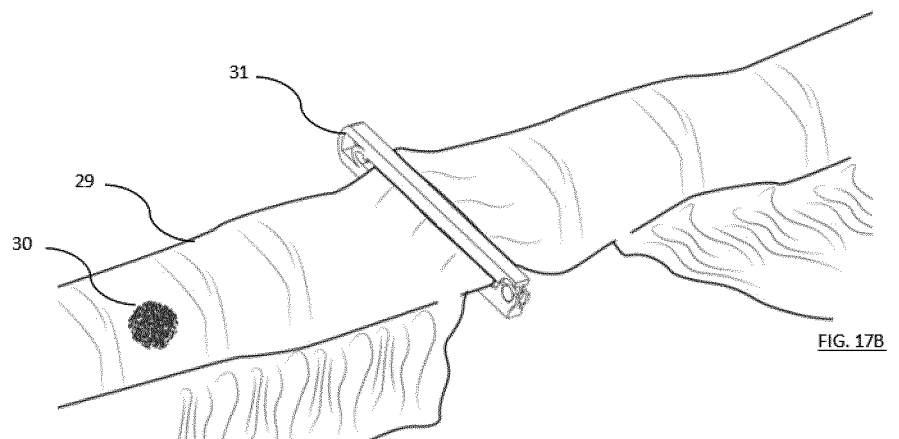
FIG. 17B shows the passive clamp attached to and clamping the colon.
Figure 19:
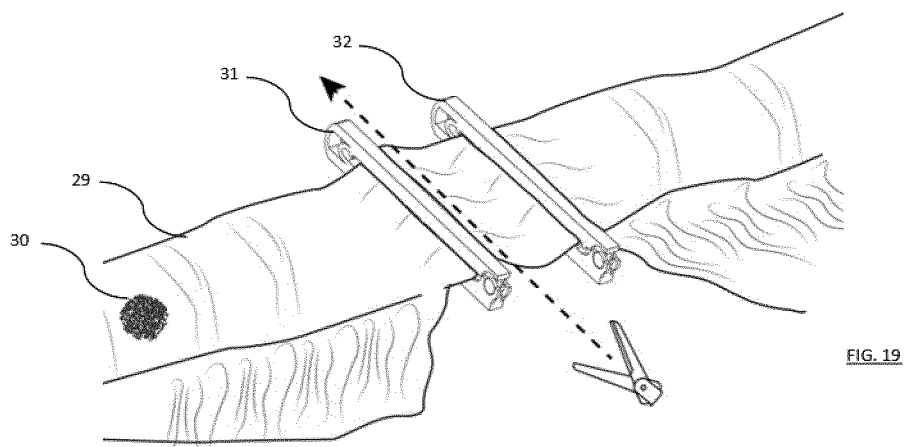
FIG. 19 shows the colon being cut between the clamps and FIG. 20 shows the distal section of the colon with the clamp attached.
Figure 20:
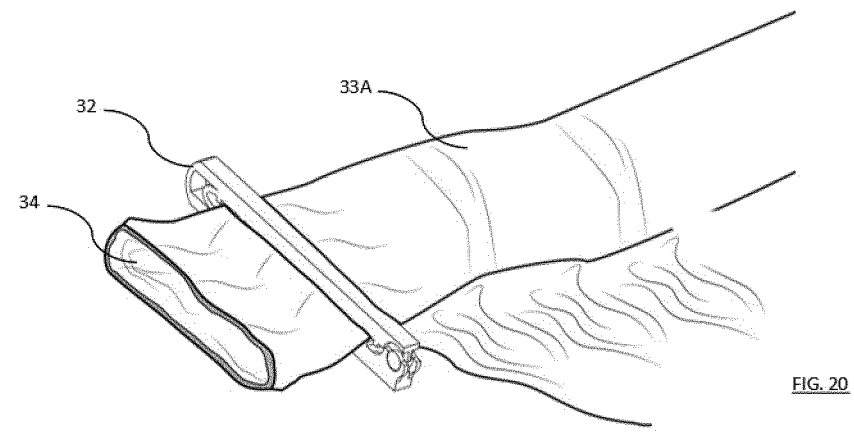
Figure 21:
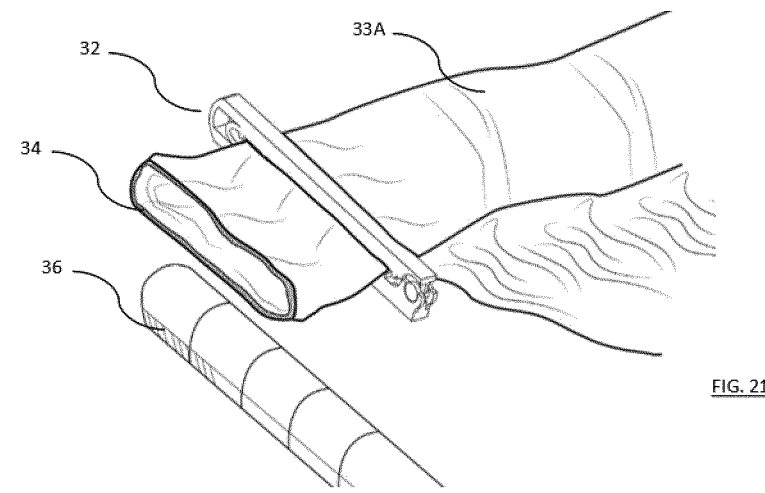
FIG. 21 shows a delivery device approaching the open end of the distal colon.
Figures 22, 23, 24:
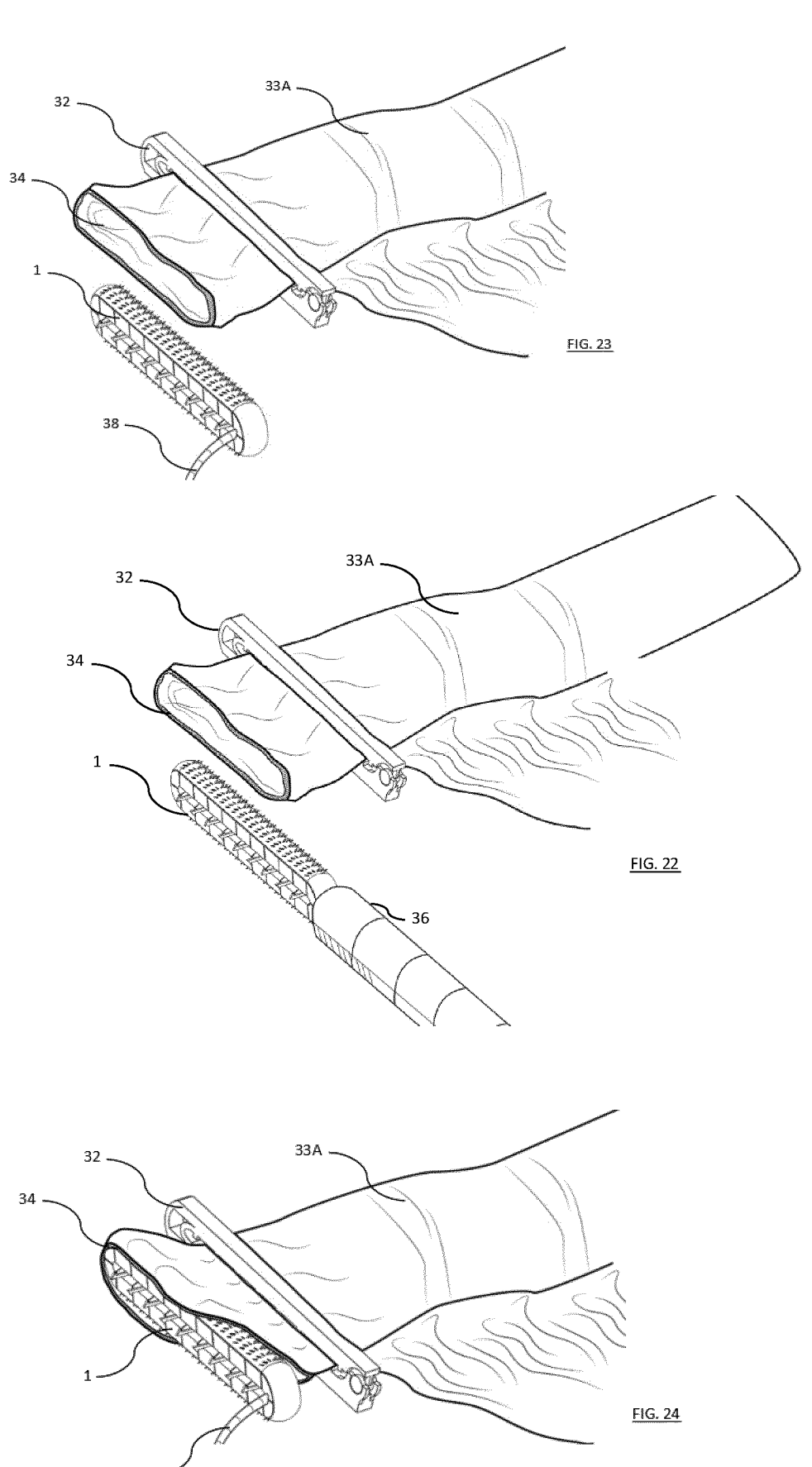
FIG. 22 shows a first compression ring in an elongated delivery configuration being advanced out of an open end of the delivery device.
FIG. 23 shows the first compression ring after being delivered adjacent the open end of the distal colon.
FIG. 24 shows the first compression ring being advanced into the open end of the distal colon and FIG. 25 shows the ring positioned inside and diametrically across the colon.
Figure 25:
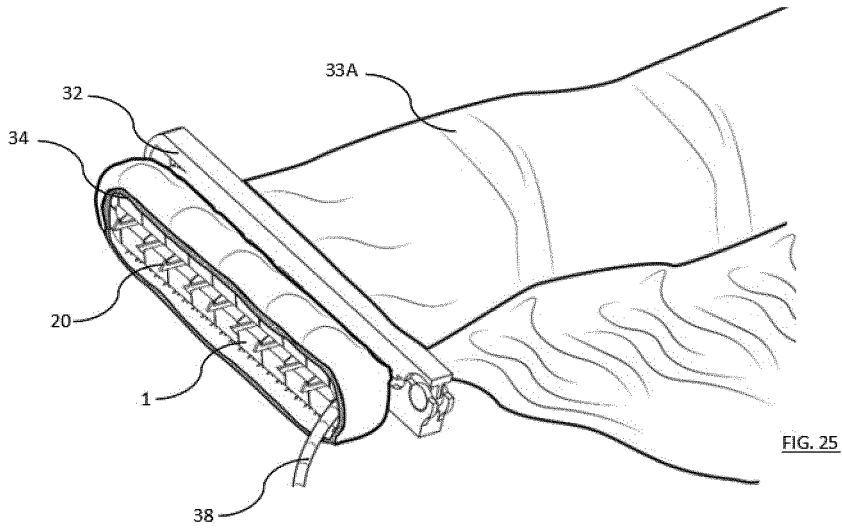
Figure 26:
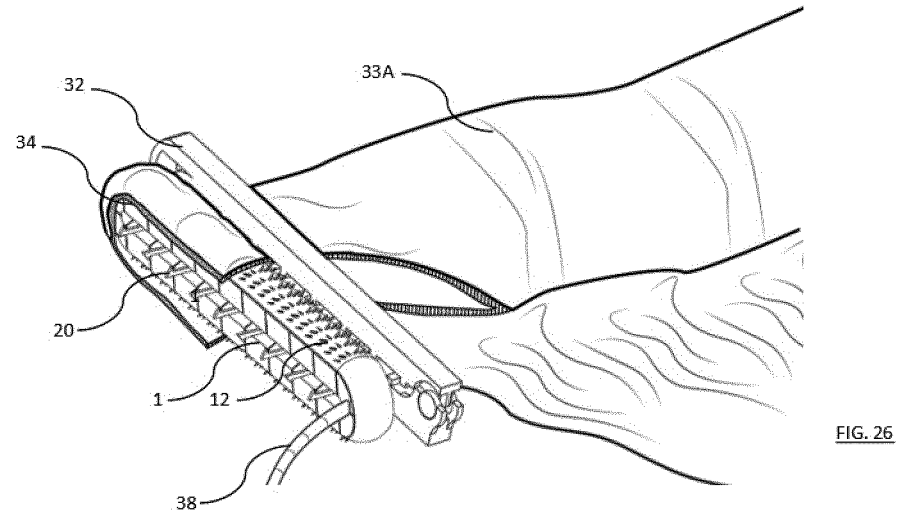
FIG. 26 shows the colon partially cut away illustrating the anchoring barbs on the surface of the ring.

The use of the device in a procedure to perform an end-to-end compression anastomosis of the colon will now be described, referring to FIGS. 17 to 35. FIGS. 17A and 17B show a section of the colon 29 with a tumour 30, and a passive clamp 31 being attached to and clamping the colon distally of the tumour. FIG. 18 illustrates a second passive clamp 32 being attached to the colon distally of the tumour and spaced apart from the first clamp by about 6 cm. FIG. 19 shows the colon being cut between the clamps to sever the colon and FIG. 20 shows a healthy section of colon 33A distal of the cut with an open end 34. FIGS. 21 to 25 show a delivery device 36 approaching the open end 34 of the colon, a first compression ring 1 in an elongated delivery configuration being advanced out of an open end of the delivery device, and delivered adjacent the open end of the distal colon, before being advanced into the open end 34 of the colon and positioned inside and diametrically across the colon about 1-4 cm from the cut open end. FIG. 26 shows the colon partially cut away illustrating the anchoring barbs on the surface of the ring engaged with colon tissue at the open end 34 of the colon.

Before the procedure is performed, a suitable compression ring is chosen by the surgeon based on imaging or observation of the colon. The ring should have a diameter when deployed that is approximately the same diameter of the colon, or slightly larger or smaller, so that when the ring is deployed most of the external surface of the ring abuts the inner wall of the colon.

Figure 27:
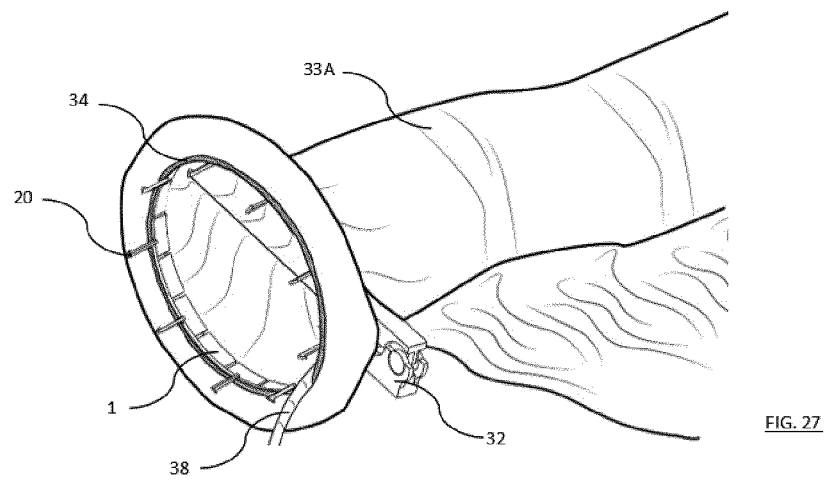
FIG. 27 shows the ring after being deployed into a radially expanded configuration showing how the cut end of the distal colon inverts around the ring.
Figure 28:
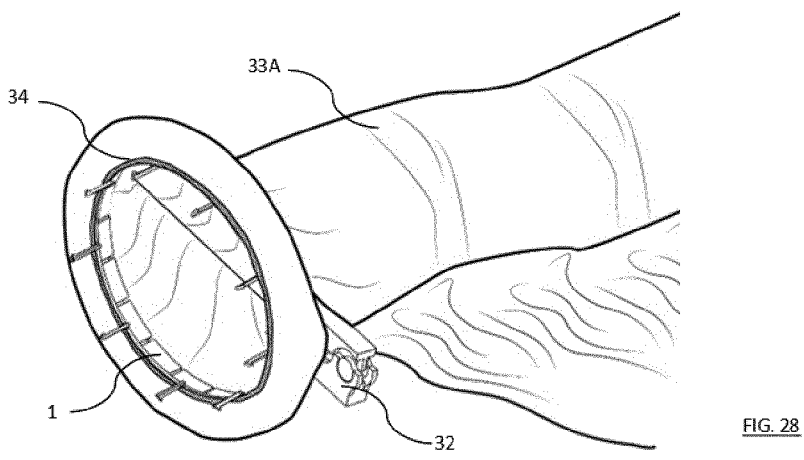
FIG. 28 shows the deployed ring with the balloon inflation conduit detached and retracted.

FIG. 27 shows the ring 1 after being deployed into a radially expanded configuration showing how the open end 34 of the colon 33A drapes around the distal face of the ring. A balloon inflation conduit 38 is then detached from the inflatable ring and retracted through the delivery device (FIG. 28).

The steps described above with reference to FIGS. 17 to 28 are then performed on a section of the colon proximal of the tumour, to provide a section of healthy colon proximal of the tumour with an open end, and an excised section of colon containing the tumour which is clamped at both ends preventing escape of faecal matter into the abdomen. The excised section of colon may then be removed, and a matching compression ring positioned inside the open end of the colon and deployed as described above.

Figure 29:
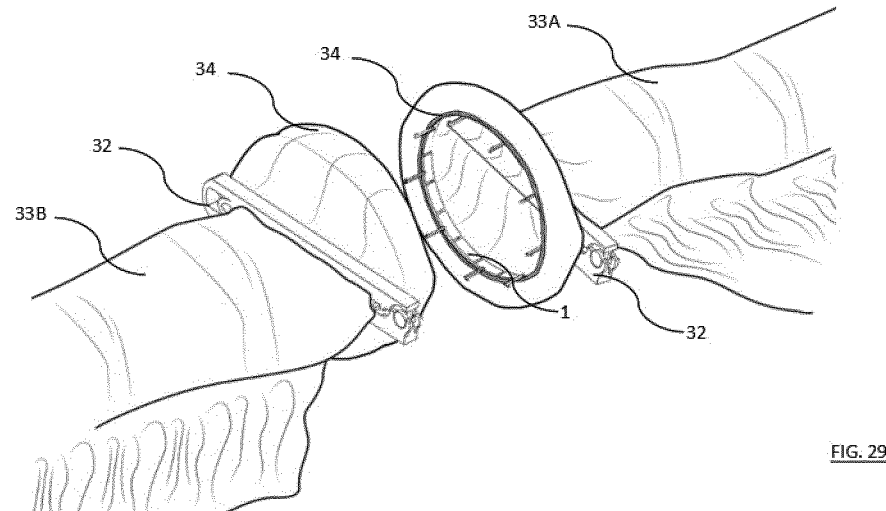
FIG. 29 shows the distal colon with the deployed compression ring and a proximal section of colon with a matching compression ring in a deployed configuration. The proximal section is prepared in the same way as the distal colon.
Figure 30:
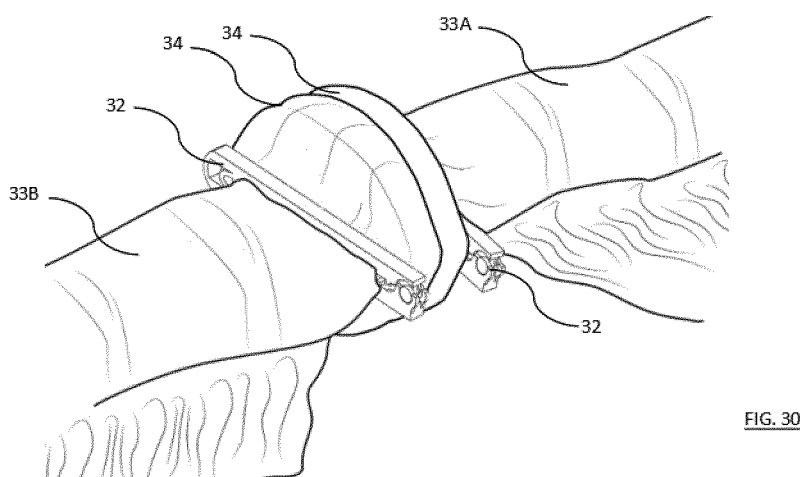
FIG. 30 shows the cut ends of the colon being brought together and the compression rings being coupled together by the engagement of the latching arms of one ring with the other ring, which results in the sections of colon that are inverted around the distal ends of the rings being compressed together to form a compression anastomosis as shown in FIG. 31.
Figure 31:
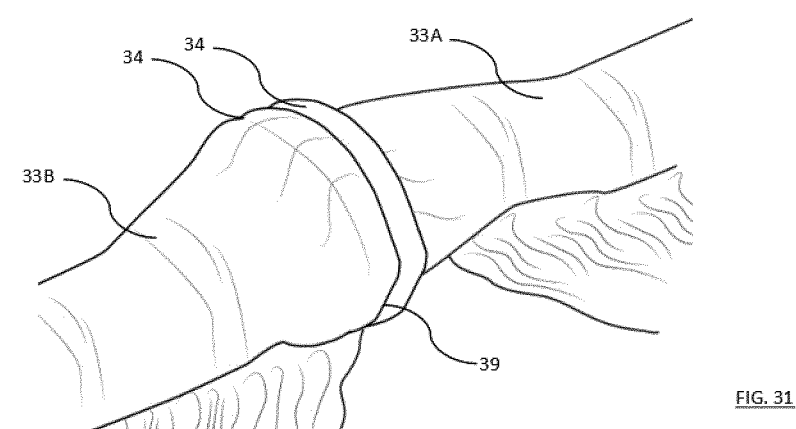
Figure 32:
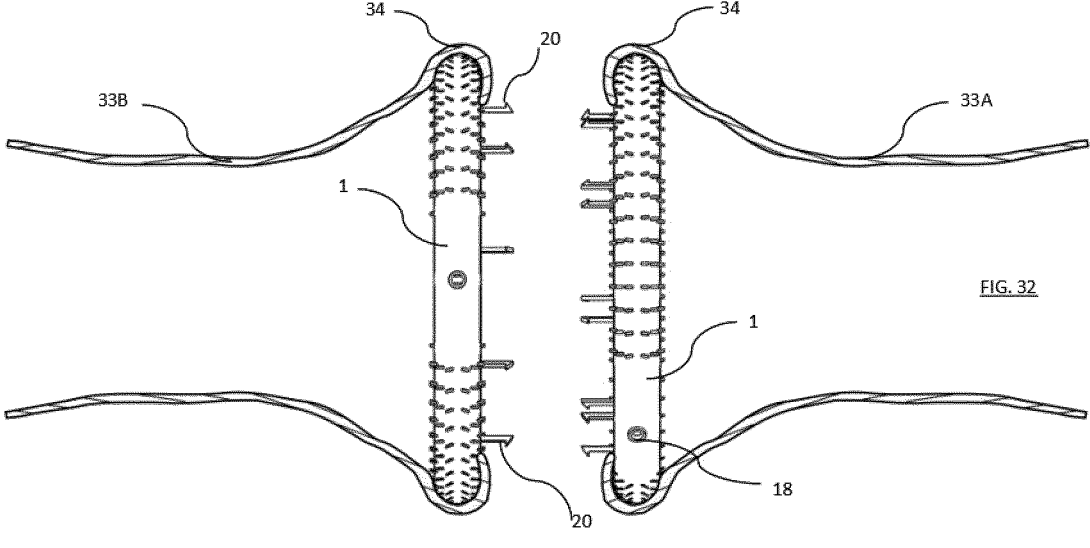
Figure 33:
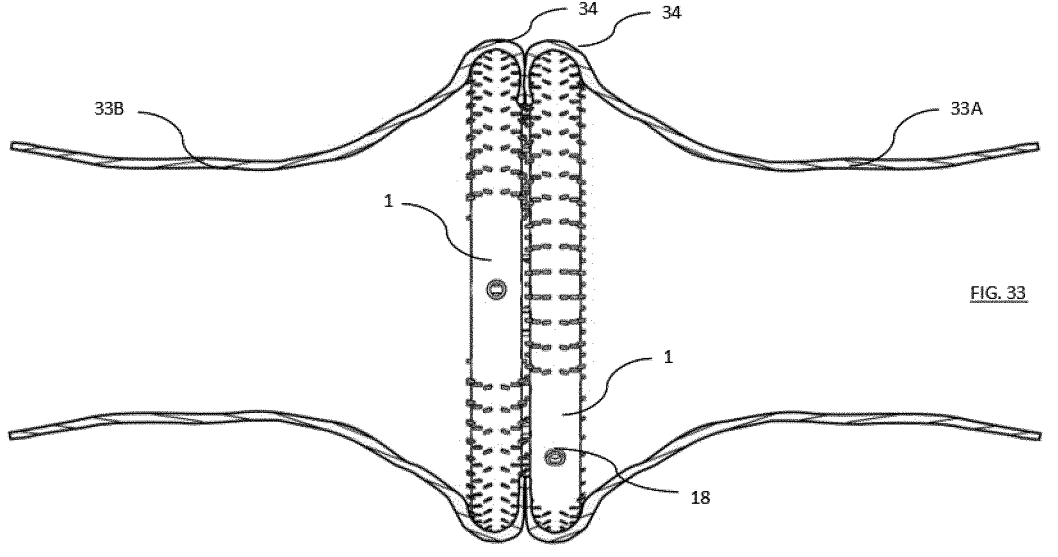
Figure 49:
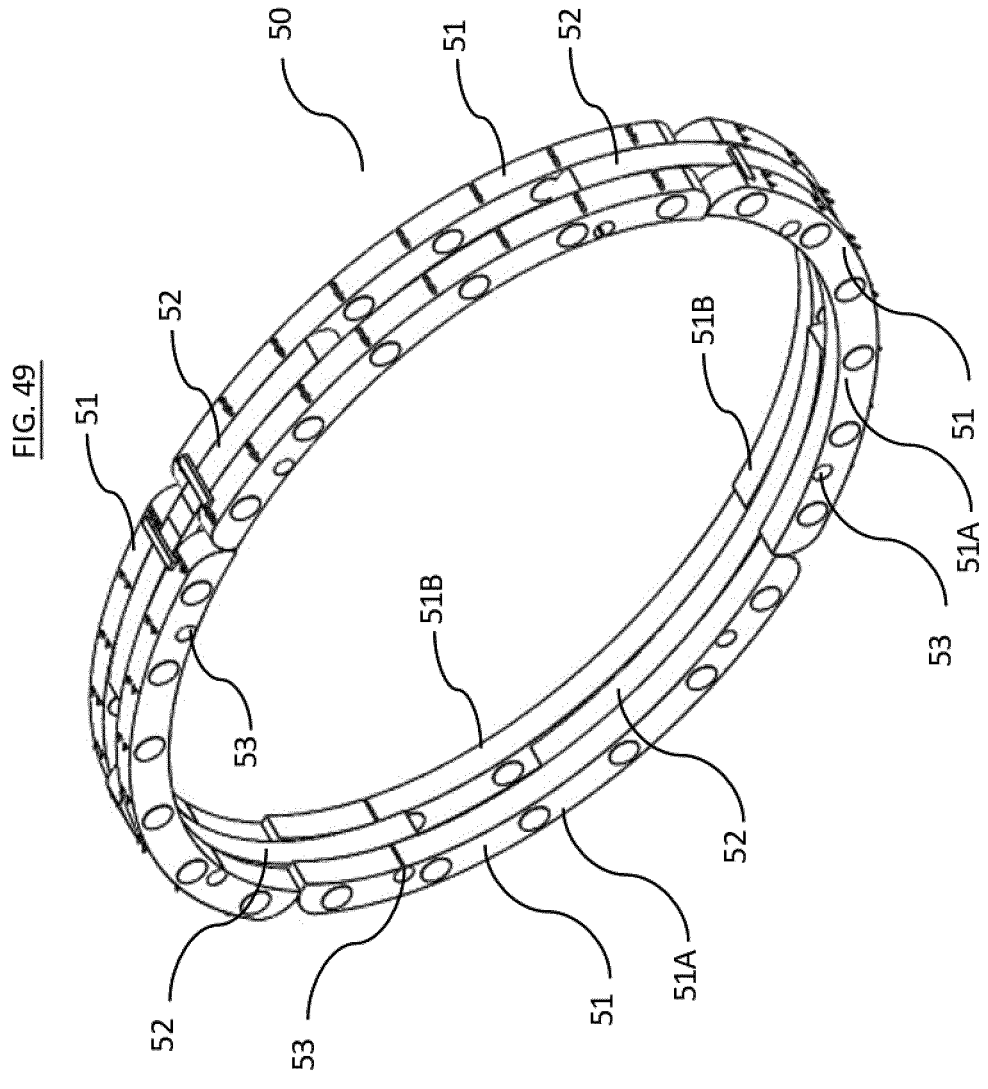
FIG. 49 is a perspective view of a compression ring device according to an alternative embodiment of the invention in a delivery radially retracted configuration.
Figures 50, 51A, 51B:
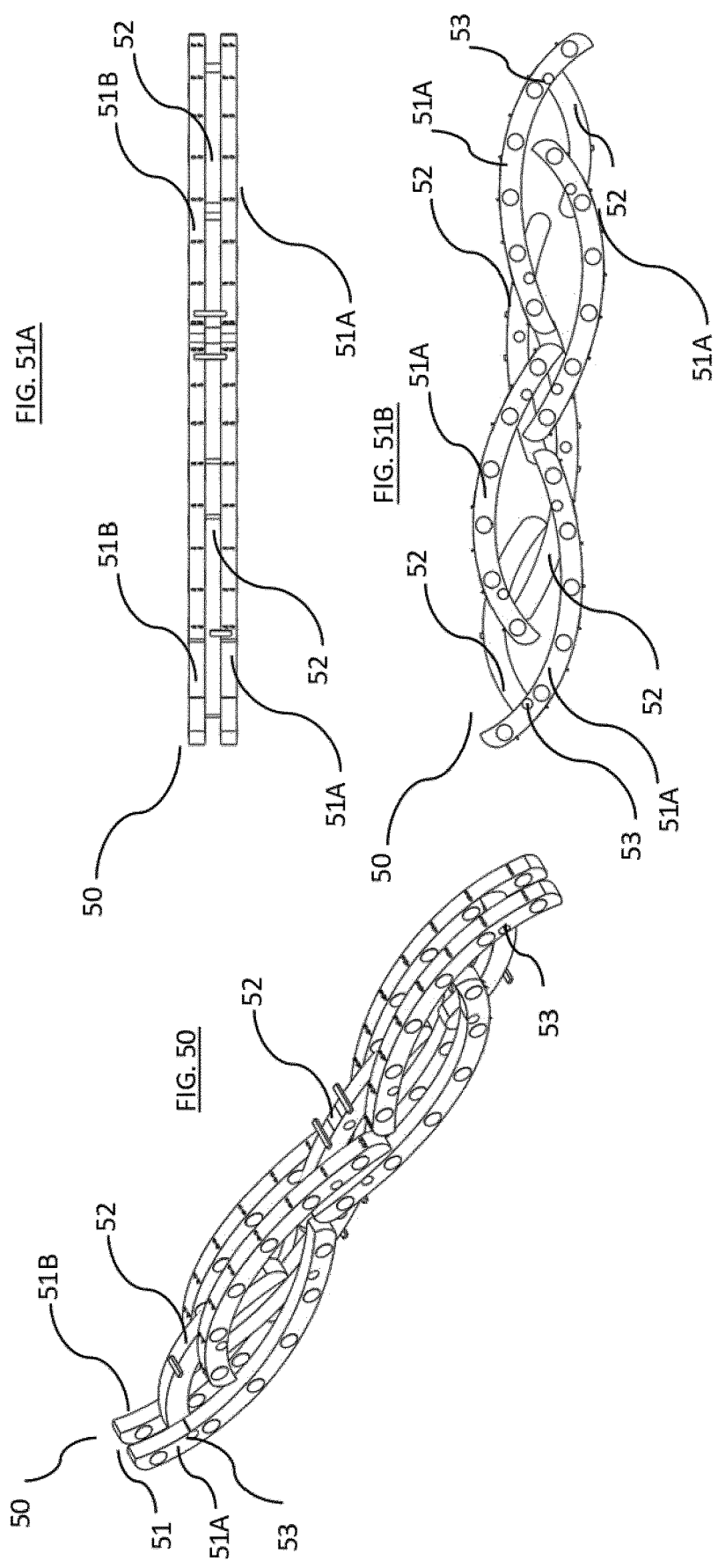
FIG. 50 is a perspective view of the compression ring device of FIG. 49.
FIGS. 51A and 51B are top and side elevational views of the compression ring device of FIG. 49.

FIG. 29 shows the first section of healthy colon 33A with the deployed compression ring and the second section of healthy colon 33B with the matching compression ring (not shown) in a deployed configuration. FIG. 30 illustrates the cut ends of the colon being brought together and the compression rings being coupled together by the engagement of the latching arms of one ring with the other ring (as described above), which results in the sections of colon that are inverted around the rings being compressed together to form a compression anastomosis as shown in FIG. 31.

Figures 34, 35:
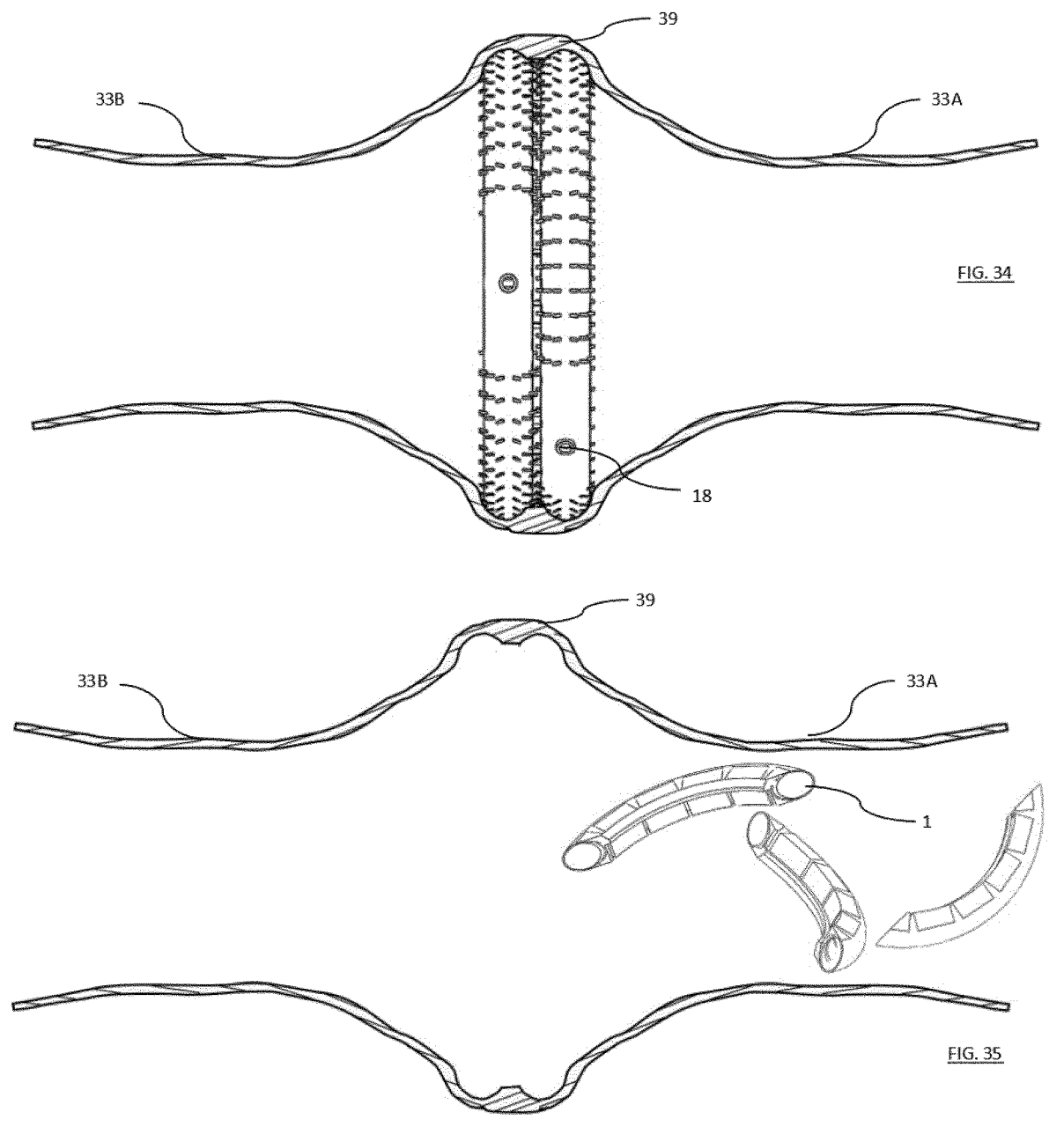

FIGS. 32 to 35 are side views showing the compression rings 1 deployed in the end of the two sections of colon (FIG. 32), the rings being coupled together resulting in the tissue 34 at the ends of the two sections 33A, 33B being compressed together (FIG. 33), forming an anastomosis 39 (FIG. 34), and the subsequent biodegrading of weakened sections of the rings allowing sections of the ring to be passed along the colon and discharged through the anus (FIG. 35).

Referring to FIGS. 36 to 47, an alternative embodiment of the compression ring, indicated generally by the reference numeral 40, is described in which parts described with reference to the previous embodiment are assigned the same reference numerals. In this embodiment, the compression ring is of the same general structure as the compression ring device 1 described previously with reference to FIGS. 1 to 9, but the coupling elements comprises a series of magnets of a first polarity 41 on one ring and corresponding magnets of opposite polarity 42 on the second ring. As illustrated, the magnets are positioned on a sidewall of the housing 3 on every second segment 15A. The use of this embodiment is the same as the previous embodiment with the exception that the rings are linked together in a compression anastomosis configuration by the magnets.

Figures 55, 56, 57, 58:
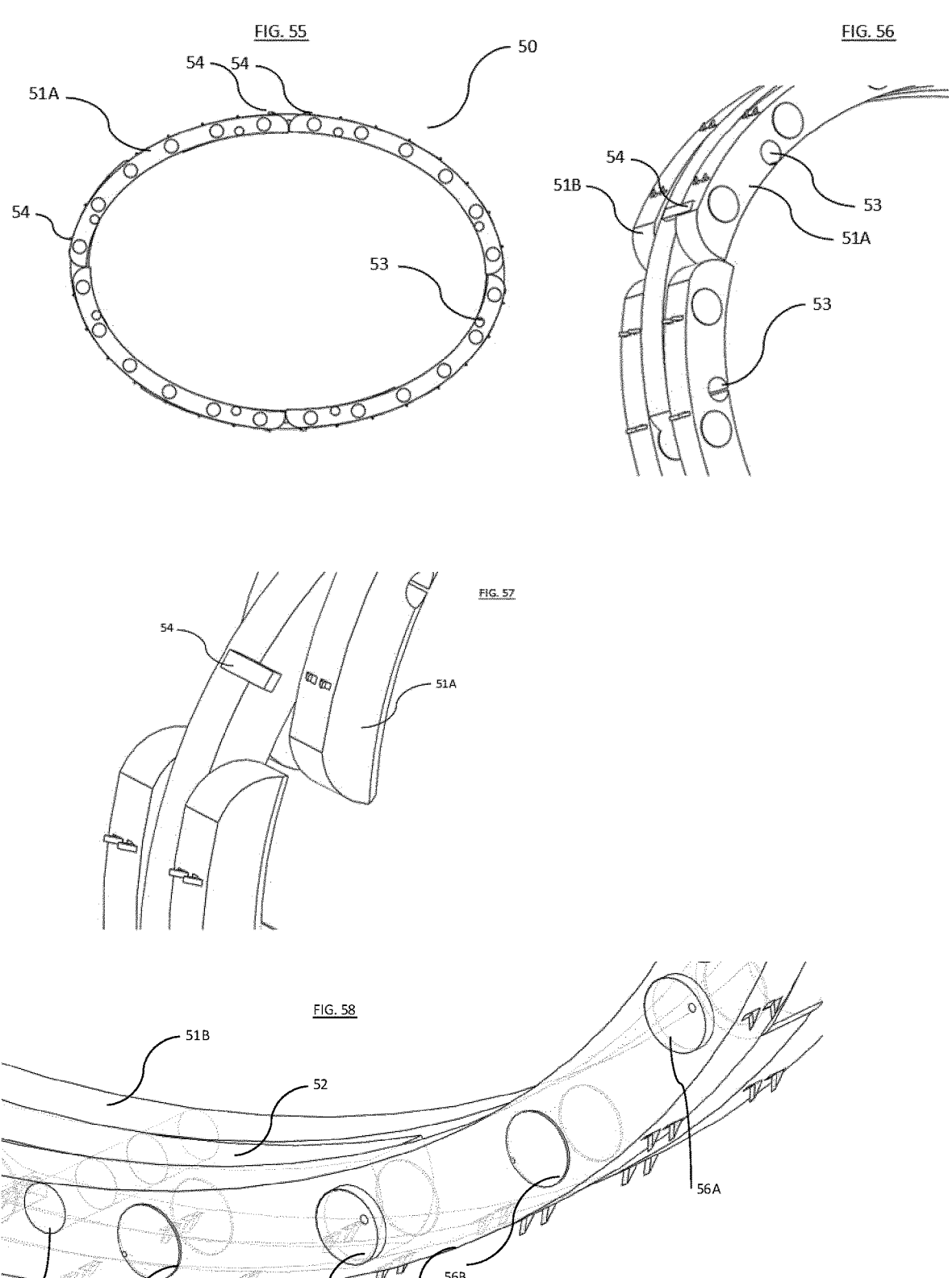
FIG. 55 is a side elevational view of the compression ring device of FIG. 53.
FIG. 56 is a detailed view of the compression ring device of FIG. 53 showing the braking mechanism.
FIG. 57 is a further detailed view of the compression ring device of FIG. 53 showing the braking mechanism.
FIG. 58 is a detailed view of a side of the compression ring device of FIG. 53 showing one embodiment of coupling formations in this case alternating concave and convex magnetic formations.
Figure 60:
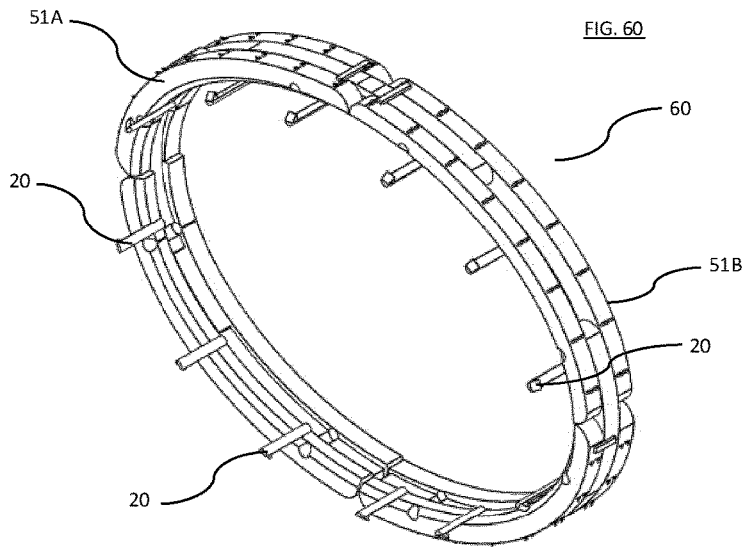
FIG. 60 is a perspective view of a compression ring that is similar to the embodiment of FIGS. 58 and 59 but having alternative coupling elements, in this case latching arms.

Referring to FIGS. 49 to 59, an alternative embodiment of the compression ring, indicated generally by the reference numeral 50, is described in which parts described with reference to the previous embodiment are assigned the same reference numerals. In this embodiment, the compression ring 50 comprises a plurality of rigid alternating first and second links hingedly coupled together end to end, to form an annulus that is can be adjusted into a low-profile configuration and then deployed into a radially expanded configuration. In the embodiment shown the compression ring device has four first links 51 connected together in an end-to-end arrangement by four second links 52. Each first link 51 comprises two spaced-apart arms 51A and 51B and each second link 52 comprises a single middle arm, in which the ends 52A, 52B of the single middle arm 52 is disposed in between and abutting the two spaced apart arms 51A, 51B of an adjacent first link and pivotally connected to the two spaced apart arms by a pin 53. Each of the arms is curved and the arms of the first link are longer than the second middle arm. The curvature and length of the arms is configured such that when the device is articulated into the deployed configuration, the ring has an oval shape defined by the four first links arranged in an end-to-end relationship. A top surface of the spaced apart arms 51A, 51B has sets of tissue engaging barbs 58. The ring 50 also has a braking mechanism to limit pivoting of the first and second links relative to each other during deployment once the oval shape has been formed. The braking mechanism comprises a stop formation 54 disposed on the top centre of the middle arm 52 which projects laterally into the path of one of the first link arms 51A, 51B to prevent further pivoting of the first link arms once these have aligned longitudinally with the second middle arm. The first link arm has a detent 55 positioned and dimensioned to receive the stop formation 54. The detent may be dimensioned for snap-fit engagement with the stop 54, to act as a locking mechanism to hold the ring rigid once the desired oval deployed shape has been reached. Other forms of locking mechanisms may be provided as well, for example formations of a sidewall of the middle arm and corresponding formations on the sidewall of one of the arms 51A, 51B that are configured for engagement when the ring is fully deployed to lock the ring in the fully deployed position. The braking mechanism is illustrated in FIGS. 55 and 56.

Figure 59:
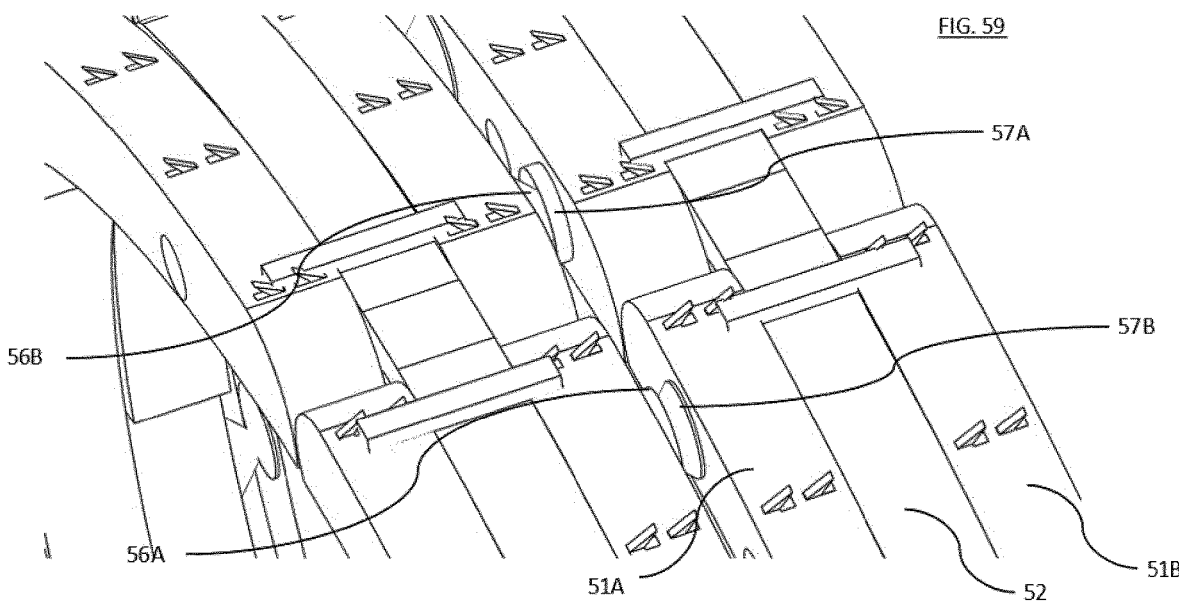
FIG. 59 is a detailed view of two compression ring devices of FIG. 58 coupled together with the concave and convex magnetic formations.
Figure 69:
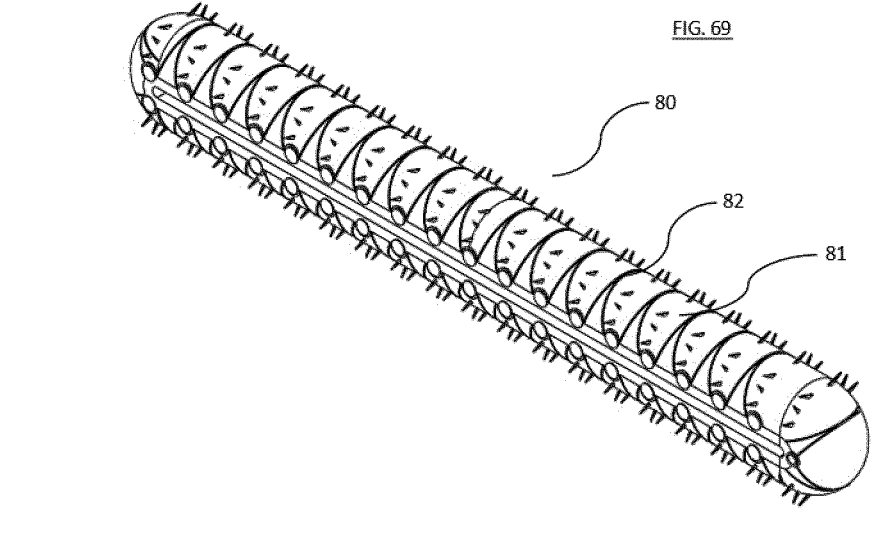
FIG. 69 is a perspective view of a further embodiment of a compression ring device according to the invention.
Figure 70:
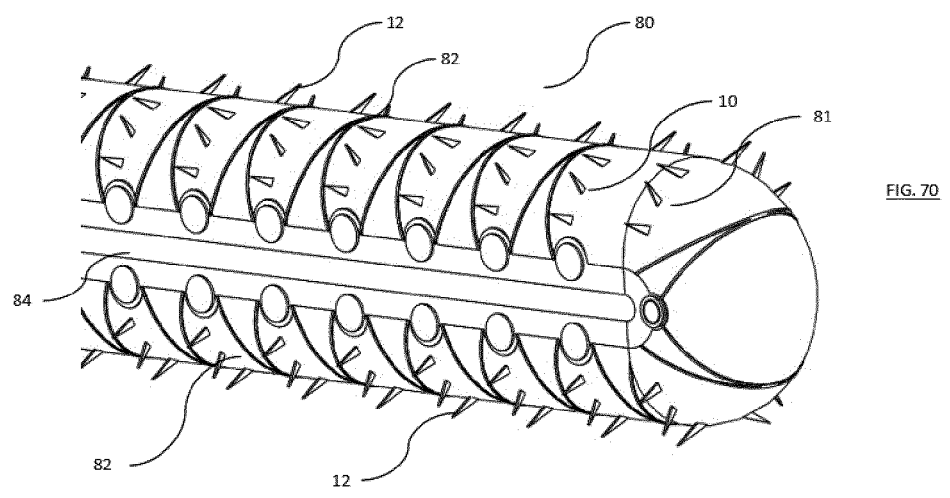
FIG. 70 is a perspective view of an end of the compression ring device of FIG. 69.
Figure 71:
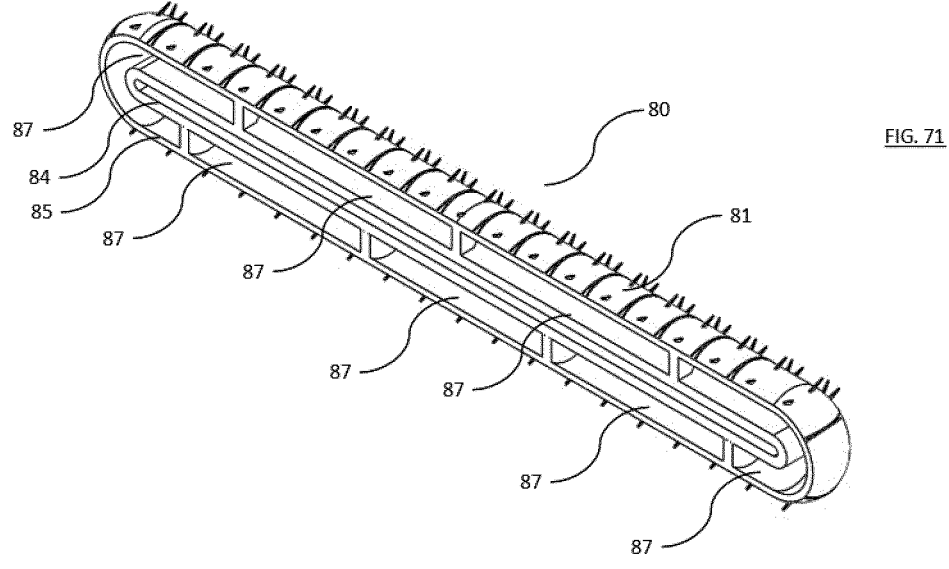
FIG. 71 is a longitudinal sectional view of the compression ring device of FIG. 69.

The coupling elements provided on ring 50 comprises magnates, particularly a series of magnets of a first polarity 56 on a side of one ring and corresponding magnets of opposite polarity 57 on the second ring. In the embodiment shown, the magnets 56 on one ring include concave magnets 56A and convex magnets 56B and corresponding convex magnates 57A and concave magnets 57B are provided on the other ring, as illustrated in FIGS. 58 and 59. The use of this embodiment is the same as the previous embodiment.

FIGS. 60 to 64 illustrate an alternative embodiment of the compression ring, indicated generally by the reference numeral 60, is described in which parts described with reference to the previous embodiment are assigned the same reference numerals. In this embodiment which is similar to the embodiment described with reference to FIGS. 48 to 57, the coupling elements comprise latching arms 20 as described previously, which are attached to one of the arms of the first link arm and configured to latch behind an axially inner wall 61 of a first link arm of an adjacent ring. This is illustrated in FIGS. 63 and 64. The use of this embodiment is the same as the previous embodiment.

Referring to FIGS. 65 to 68, an alternative embodiment of the compression ring, indicated generally by the reference numeral 70, is described in which parts described with reference to the previous embodiment are assigned the same reference numerals. In this embodiment which is similar to the embodiment described with reference to FIGS. 1 to 9, the ring device 70 includes a cover member 71 which is attached to a periphery of the ring and functions to cover a face of the ring when it is in the delivery and deployed configurations and occlude the body lumen when the ring device is deployed to prevent passage of matter out of the body lumen when it is cut. The cover may comprise a film, for example a biodegradable polymer film, and may include a gripping tab 72 to facilitate the removal of the film by a gripping device. The use of this embodiment is the same as the previous embodiment with the exception that the rings are linked together in a compression anastomosis configuration by the magnets.

Referring to FIGS. 69 to 77, an alternative embodiment of the compression ring, indicated generally by the reference numeral 80, is described in which parts described with reference to the previous embodiment are assigned the same reference numerals. In this embodiment the ring 80 comprises an inflatable ring 81 and a strengthening element in the form of wire 82 which is wrapped around part of the ring to allow the ring upon inflation radially expand from the elongated delivery configuration (shown in FIGS. 69 to 71) to the deployed configuration showed in FIGS. 72 and 73 without cross sectional area of the ring changing unduly. In the embodiment shown the wire is embedded in the wall of the ring in a coiled formation. The inflatable ring has a base wall 84 of a thickness greater that a sidewall 85. The inflatable ring 81 includes partition walls 86 that define ring segments 87, each partition wall 86 having an opening 88 to allow fluidic communication between the ring segments 87.

Figures 77, 78:
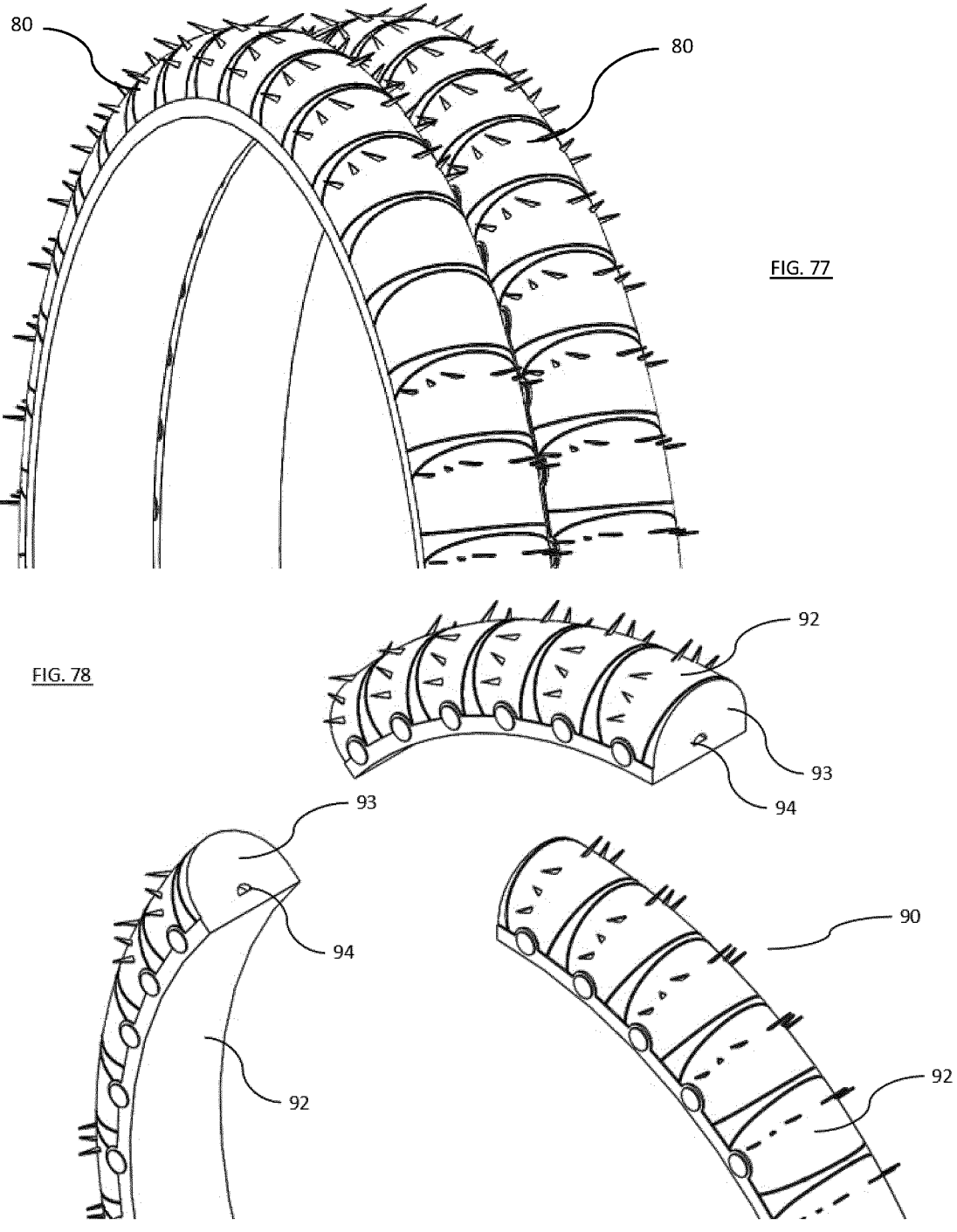
FIG. 77 is a perspective view showing two compression ring devices of FIG. 69 coupling together in a compression anastomosis configuration.
FIG. 78 is a perspective view showing the compression ring device of FIG. 69 breaking into segments due to biodegradation of weakened sections of the ring.
Figures 79, 80, 81, 82:
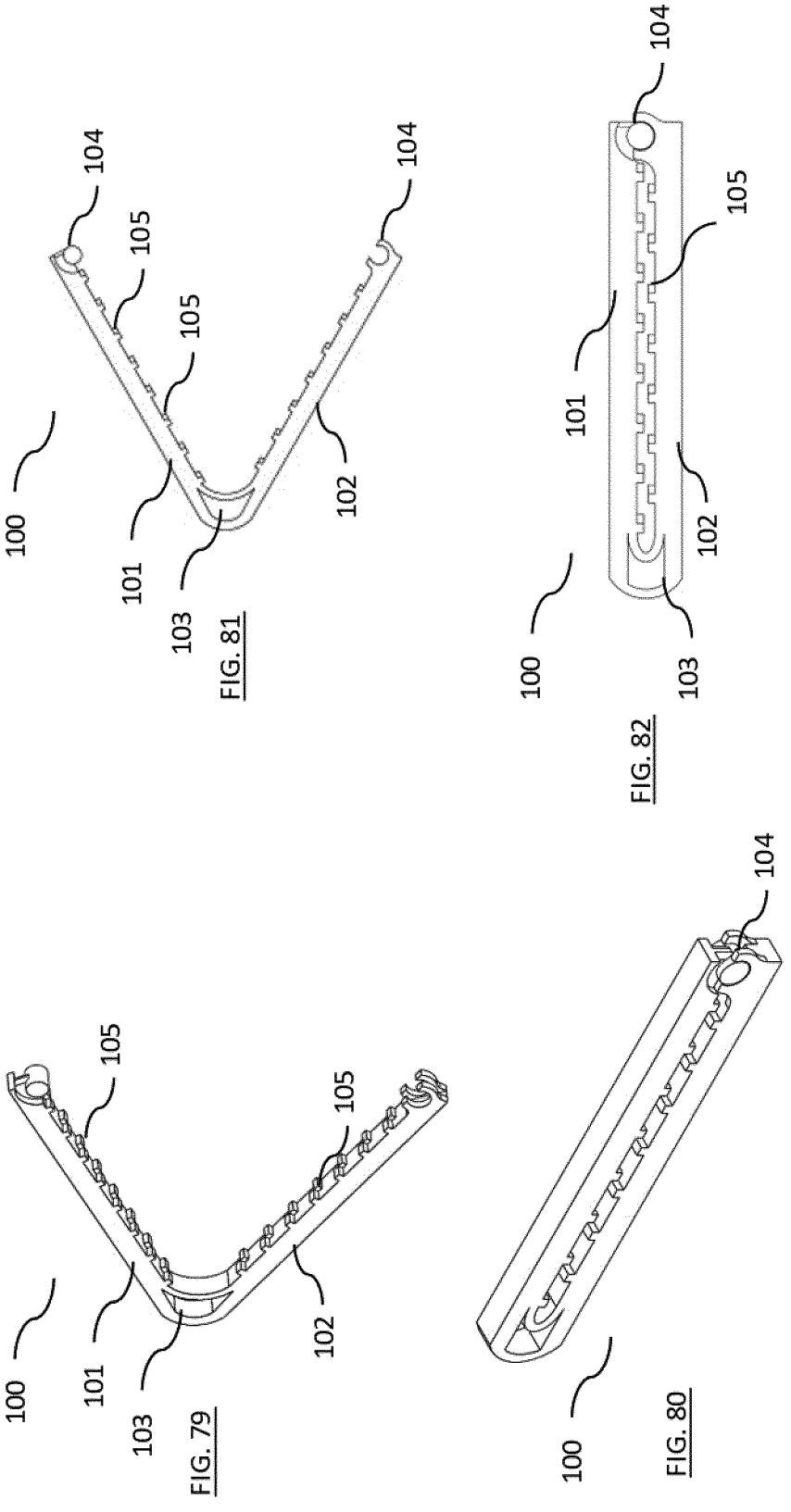
FIGS. 79 to 82 are images of a passive clamp for use with the device and system of the invention.
Figure 85:
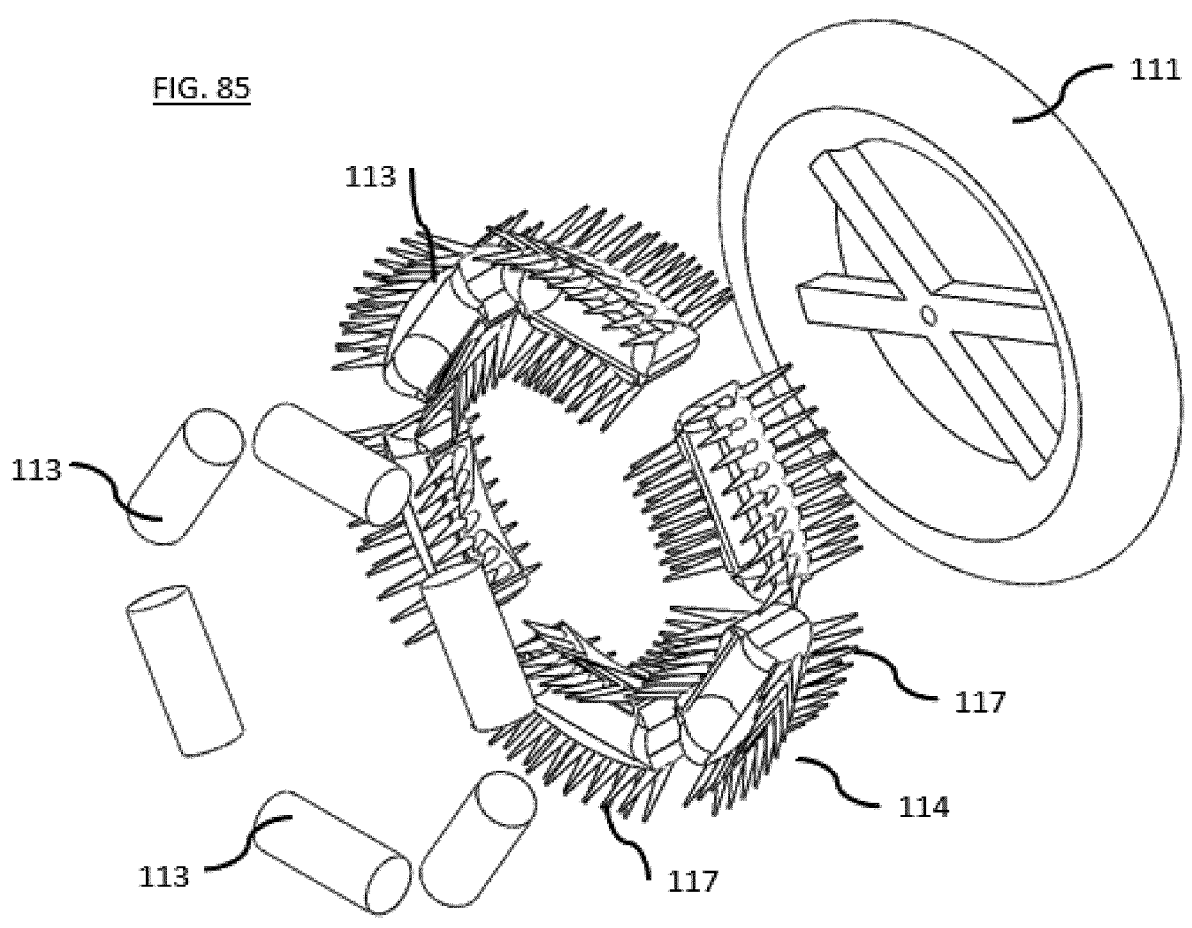
FIG. 85 is an exploded view of the components of the compression anastomosis ring of FIG. 83.

Referring to FIG. 78, an alternative embodiment of the compression ring, indicated generally by the reference numeral 90, is described in which parts described with reference to the previous embodiment are assigned the same reference numerals. In this embodiment, the ring comprises an inflatable ring 91 having chambers 92 defined by dividing walls 93 with small apertures 94 providing fluid communication between the chambers. The dividing walls are formed from a material that is more easily degraded in-vivo, and as such provide weakened sections that biodegrade first resulting in the ring device being broken into segments. The weakened sections can be placed around the ring in positions that ensure that the resultant segments are sufficiently small to pass through the colon and anus.

Referring to FIGS. 79 to 82, a passive clamp suitable for clamping a body lumen such as the colon is illustrated and indicated generally by the reference numeral 100. The clamp 100 has a first arm 101 and second arm 102 connected by a hinge 103 and locking formations 104 on a distal end of each arm for locking the clamp in a clamping position. Each arm has a clamping surface comprising a series of tissue gripping formations (in this embodiment, rectangular teeth 105). The teeth on respective clamping surfaces are staggered so that they do not engage. The clamp is configured such that the teeth on opposed clamping arms are sufficiently separated so that they do not mesh together when the clamp is in a clamping configuration. The tissue gripping elements may also take the form of wedges, pins or hydrogel like material. It is a passive clamp as it will not damage the tissue, it is placed onto the intestine and is situated in an area where it will not allow faecal matter to expel into the surgical cavity. It is also envisioned the clamp will aid in reducing bleeding.

Figure 86:
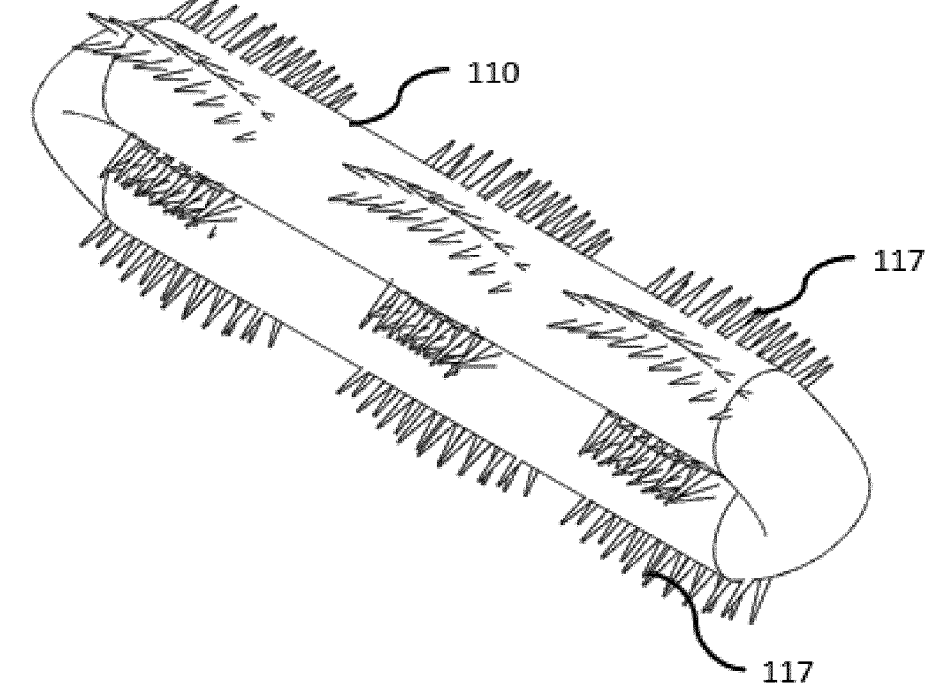
FIG. 86 illustrates the compression anastomosis ring of FIG. 83 in a flat delivery configuration.

Referring to FIGS. 83 to 96, an alternative embodiment of the compression ring, indicated generally by the reference numeral 110, is described in which parts described with reference to the previous embodiment are assigned the same reference numerals. In this embodiment, the compression ring 110 comprises an annular hollow tube 111 and a plurality of ring segments 112 disposed within the ring. In this embodiment, the ring segments are not connected together. The annular hollow tube is formed from a polymeric biodegradable material and is resiliently deformable to allow the ring to be radially compressed into a flat elongated configuration (FIGS. 86 and 88) during delivery in a minimally invasive surgical instrument and to self-deploy into the ring shape (FIG. 83) upon release from the surgical instrument and deployment at a target location. The tube in this embodiment is formed from a biodegradable material which breaks down over time in-vivo. It will be appreciated that only parts of the tube may be biodegradable, to allow the tube break into smaller parts, or indeed allow the tube to change from a closed ring shape to an open ring shape (where the tube can release the ring segments and elongate to a form that can be passed through the colon and anus.

The annular hollow tube 111 comprises an X-shaped spoke element 118 formed of a resiliently deformable material that is biased into the X-shape shown in FIG. 83 but that can be compressed in a scissor's manner during compression of the ring into the delivery configuration shown in FIG. 88.

Figure 89:
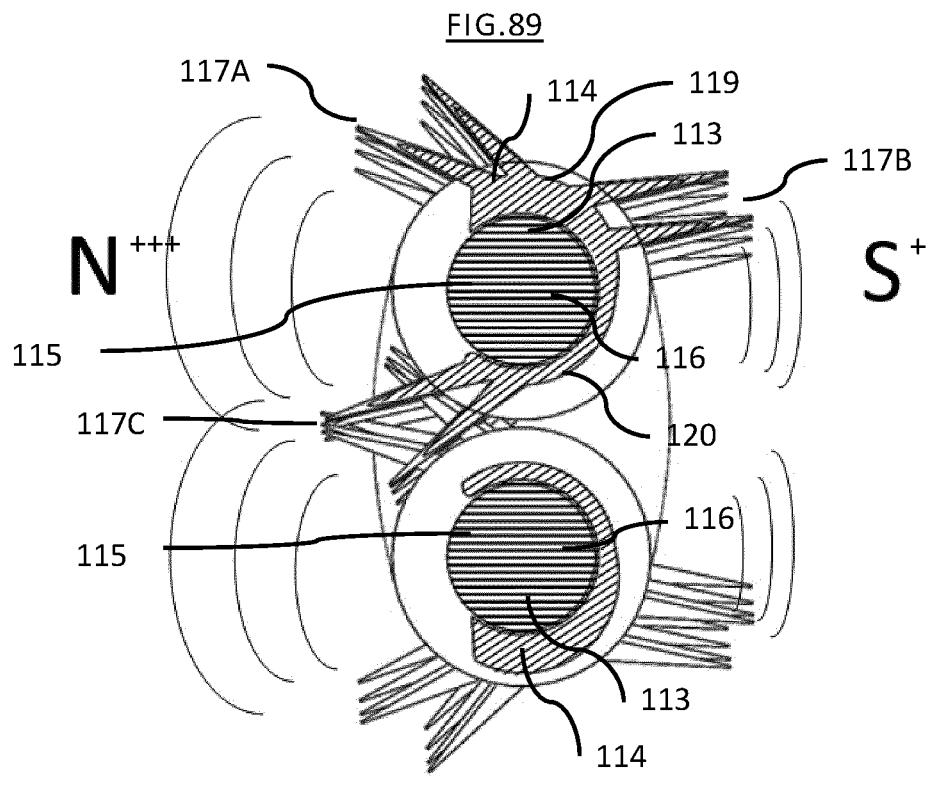
FIG. 89 is a sectional view through the compression anastomosis ring of FIG. 83 showing the outer sheath partially embracing the magnetic inner core and the disposition of anchors extending through the annular hollow tube.
Figure 90:
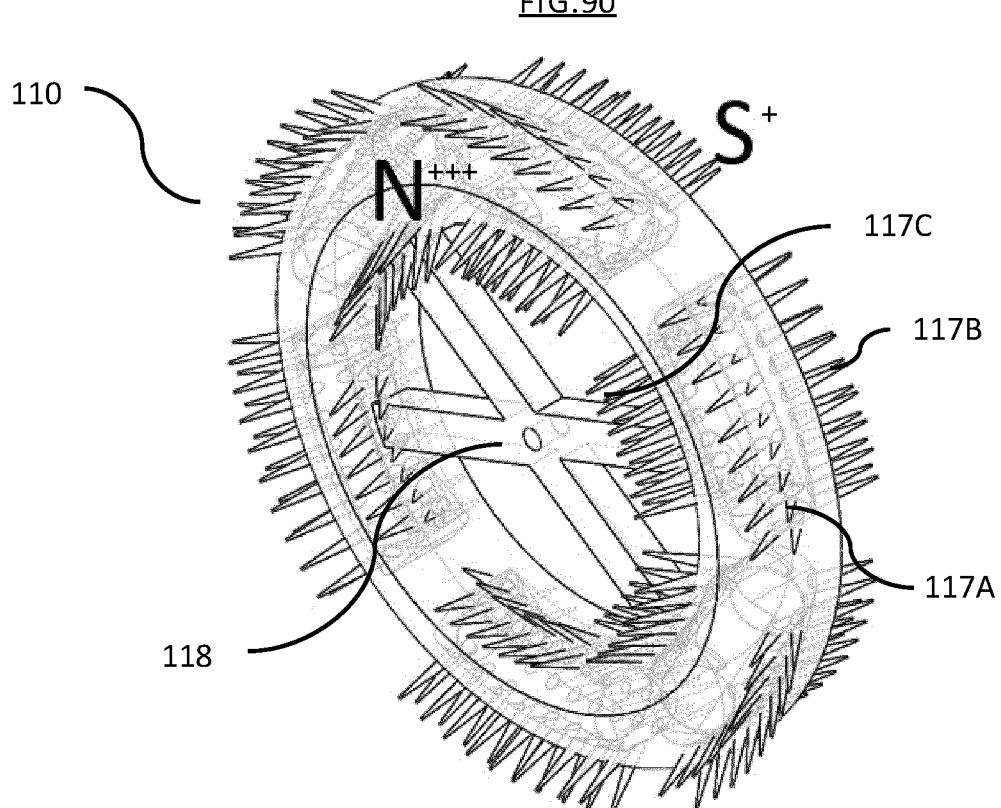
FIG. 90 shows the anastomosis compression ring with one side exhibiting a strong north pole force (N+++) and the other side exhibit a weak south pole force (S+).
Figure 91A:
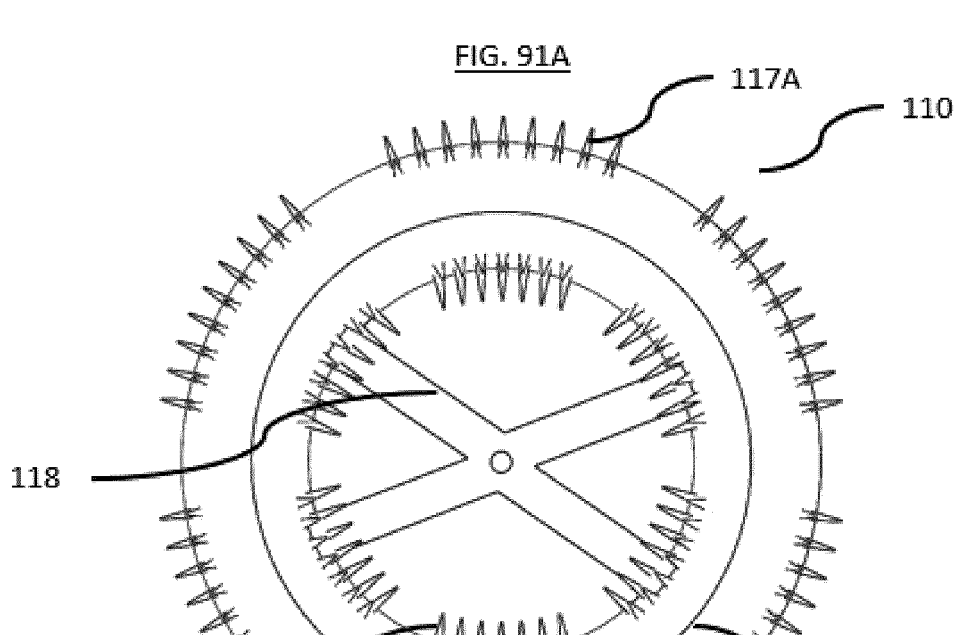
FIG. 91A is a side elevational view of the compression anastomosis ring of FIG. 83.
Figure 91B:
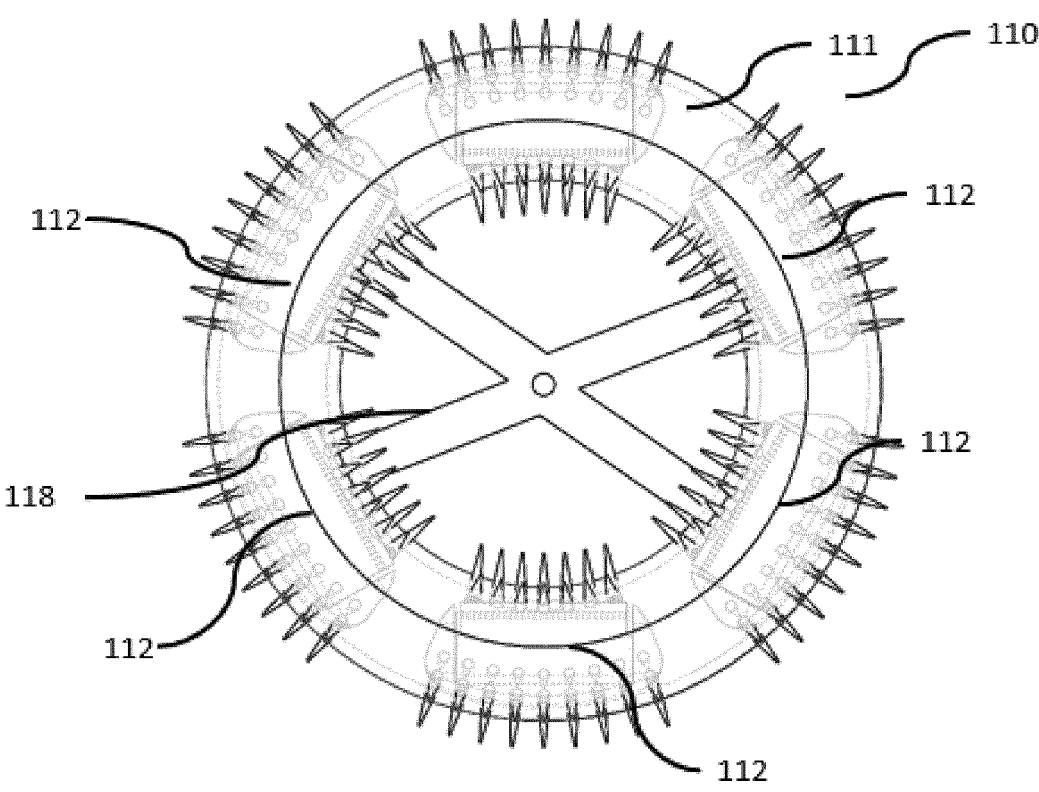
FIG. 91B is a side elevational view of two compression anastomosis rings of FIG. 83 coupled together in a compression anastomosis forming configuration.
Figures 92, 93:
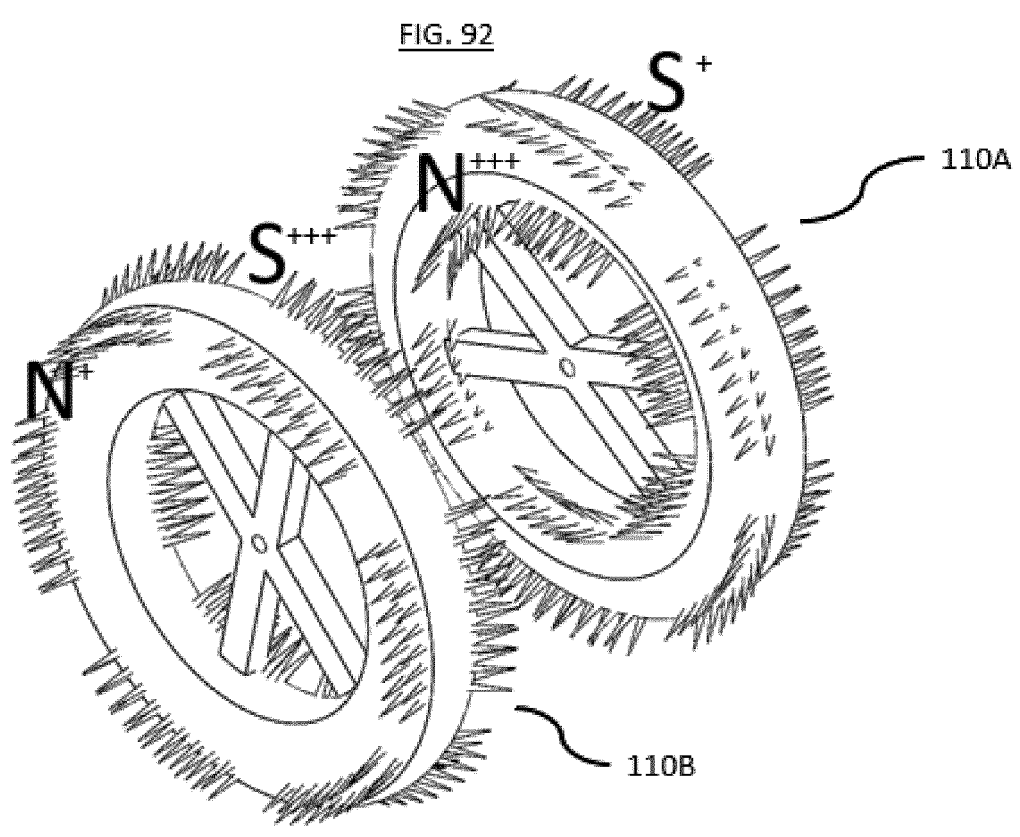
FIG. 92 shows two anastomosis compression rings with a ring-facing side of a first ring exhibiting a strong north pole force (N+++) and a ring-facing side of the second ring exhibiting a strong south pole force (S+++).
FIG. 93 is a perspective view of the two rings of FIG. 92 after being magnetically coupled together.
Figures 94A, 94B:
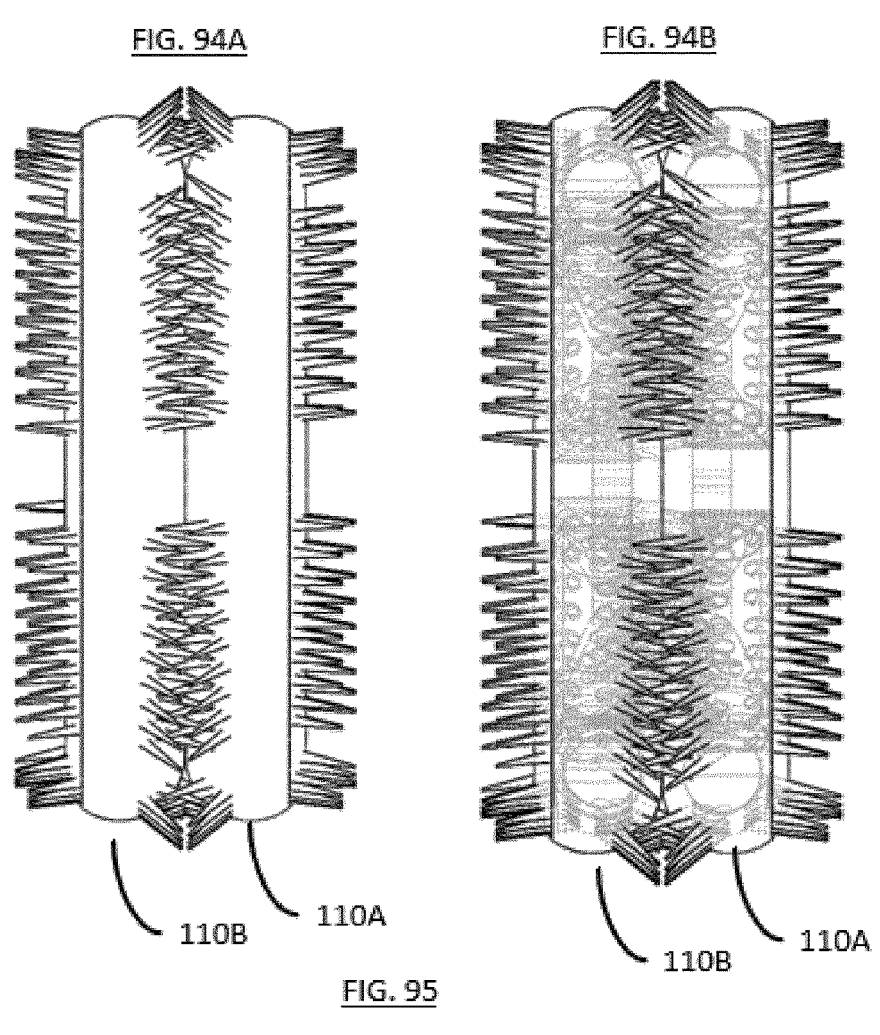
FIGS. 94A and B are end elevational views of the two rings of FIG. 92 after being magnetically coupled together.
Figure 95:
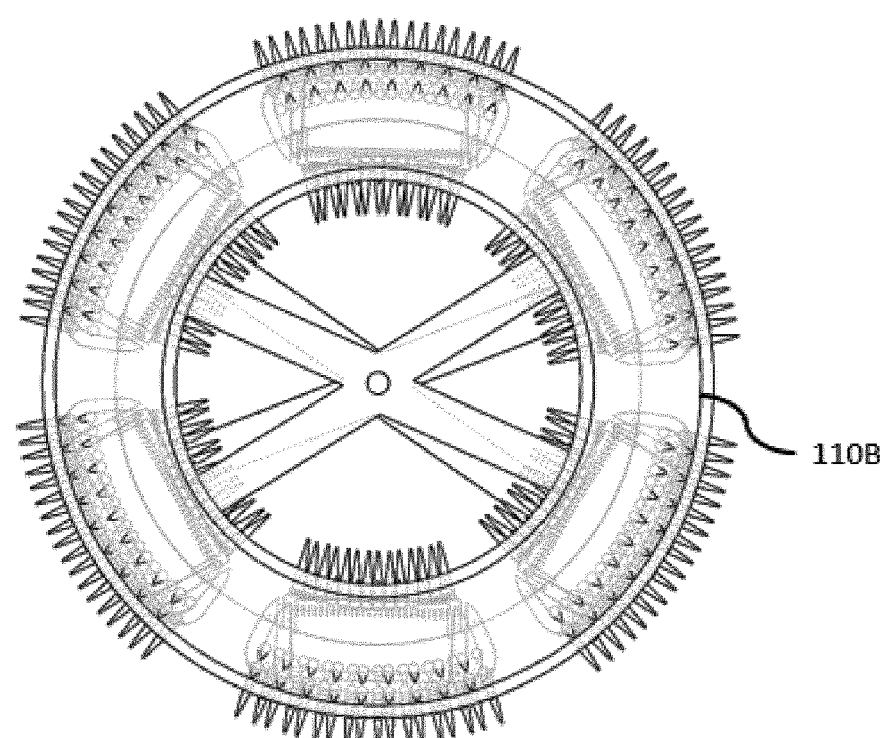
FIG. 95 is a side elevational view of the two rings of FIG. 92 after being magnetically coupled together.
Figure 96A:
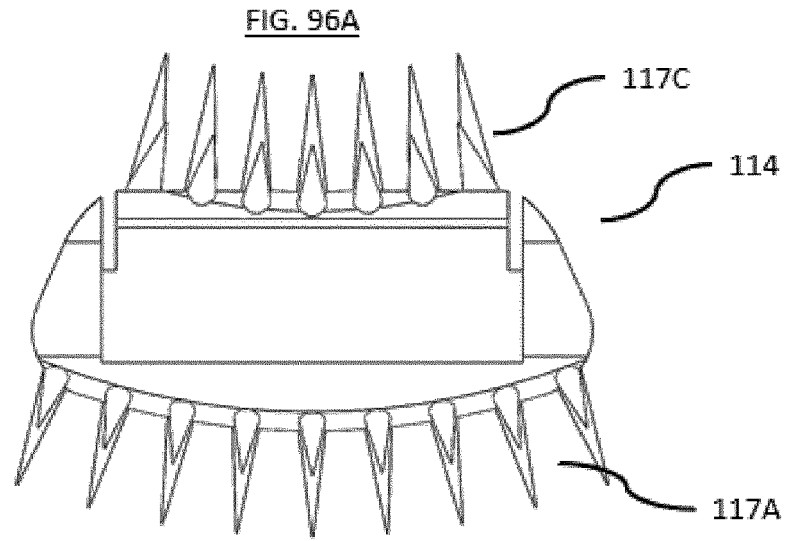
FIGS. 96A to C are side, end and perspective views of a ring segment forming part of the compression anastomosis ring of the invention.
Figure 96B:
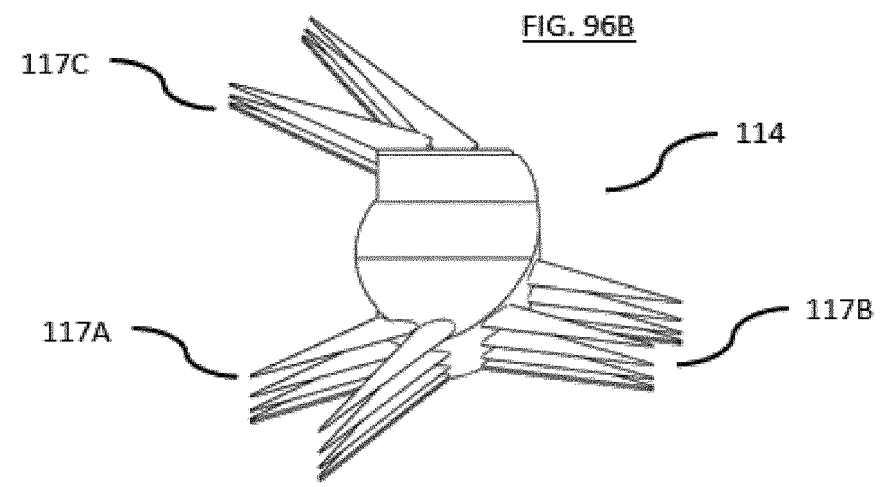
Figure 96C:
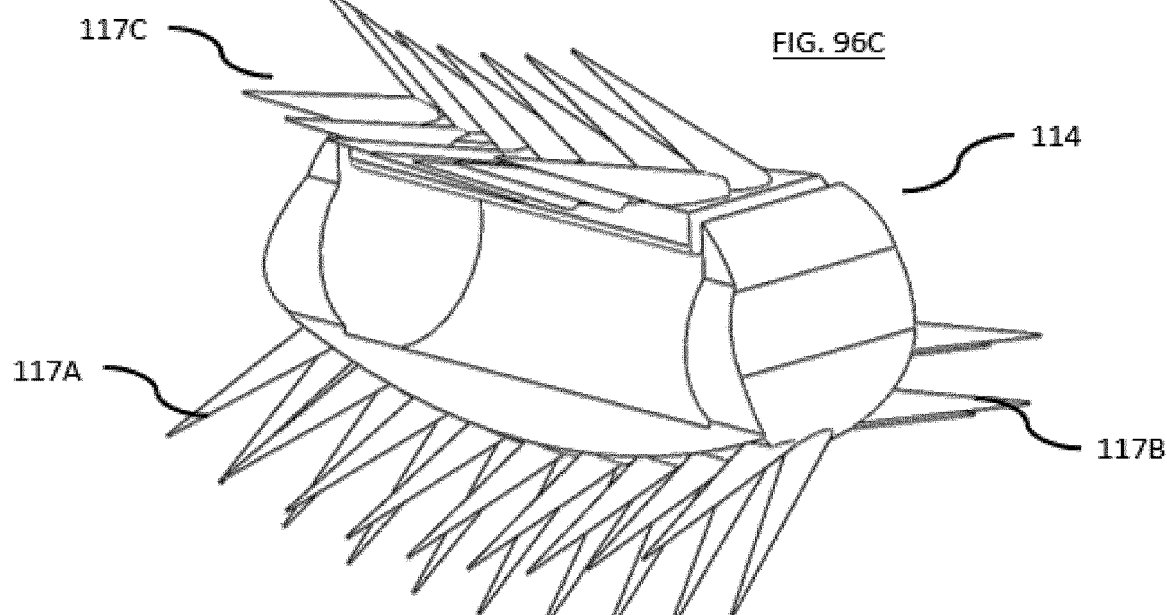

The ring segments 112 each have a cylindrical inner core 113 and an outer sheath 114. The inner core comprises a magnetic material which functions during use as a coupling element configured to couple one compression anastomosis ring to an adjacent matching ring. In this embodiment, the inner core is diametrically magnetised such that one side exhibits a north pole (north pole side 115) and an opposite side exhibits a south pole (south pole side 116). The inner cores 113 are disposed in the ring such that one face of the ring exhibits a plurality of north poles and an opposite face of the ring exhibits a plurality of south poles. This allows the rings couple together. Referring to FIGS. 89 and 96, the outer sheath 114 comprises a polymeric jacket that covers each end of the inner core and extends about 75% around the tubular inner core leaving the north pole side 115 of the inner core 113 exposed and the south pole side 116 covered. This serves to weaken the magnetic force on the south pole side 116 compared to the north pole side 115. In use and referring to FIG. 92, the rings segments of a pair of are configured such that one face of a first ring will exhibit a strong north pole (N+++) and the rings segments of a second ring will be configured such that one face of the second ring will exhibit a strong north pole (S+++).

The tissue anchors of the compression ring 110 are provided by anchors 117 that are integrally formed with the outer sheath 114. When the ring 110 is assembled the anchors 117 pierce and project through the annular hollow tube 111 providing anchors on the surface of the tube. Referring to FIGS. 87 and 89, the anchors comprise an array for first anchors 117A and second anchors 1176 disposed on a top surface 119 of the inner sheath, and an array of third anchors 117C extending from a bottom surface 120 of the inner sheath. Each array of anchors comprises two rows of anchors that extend longitudinally along the outer sheath. The first array of anchors 117A extends upwardly and laterally away from the sheath and the second array of anchors 1176 extend laterally in a direction almost opposite to the direction of the first array of anchors. The third array of anchors 117C extend downwardly and away from the sheath. When assembled into the annular tube 111, the first and third arrays of anchors 117A and 117C extends laterally from one side of the assembled ring (the side that faces a matching ring) and the third array of anchors 1176 extend laterally inwardly (away from the matching ring).

The second array of anchors 1176 aid with inserting the ring into the lumen—they prevent the ring from falling backwards into the lumen. The first array of anchors 117A aid with preventing the ring from falling forwards in the lumen. They also add anchorage when connected to the other ring to grip the tissue and hold the rings in place. The third array of anchors 117C grip the inverted tissue, when connected with the other ring they are designed to grip the inverted tissue and stop it from escaping the grip of the ring when the device is under pressure.

FIGS. 92 to 95 illustrate two compression rings 110A and 1108 coupled together in a compression anastomosis configuration in which one row of each of the first and third array of anchors project into the annular tube of the opposite ring. The tings are coupled together by means of magnetic forces of the inner cores of the respective rings.

Figure 97A:
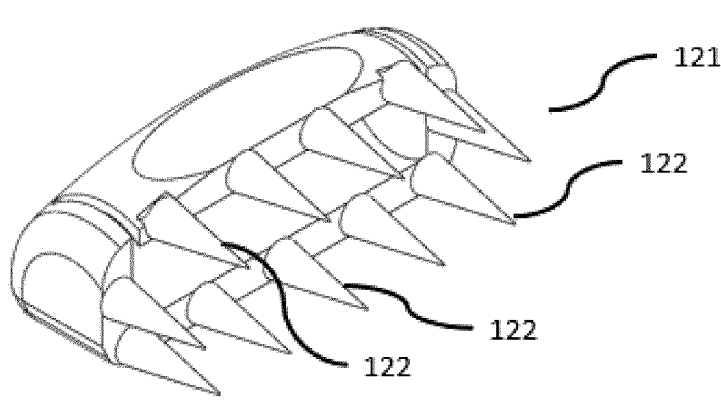
FIGS. 97A to C are perspective, end and side views of an alternative ring segment forming part of the compression anastomosis ring of the invention.
Figure 97B:
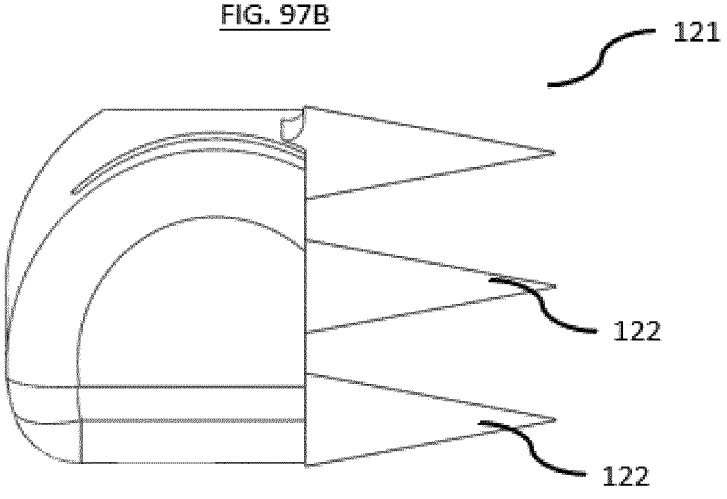
Figure 97C:
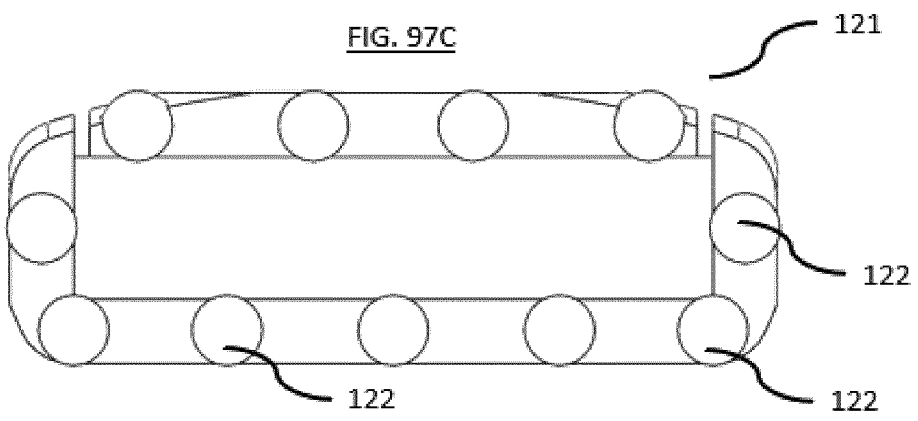

Referring to FIGS. 97 to 99, an alternative embodiment of the compression ring, indicated generally by the reference numeral 120, is described in which parts described with reference to the previous embodiment are assigned the same reference numerals. In this embodiment, the outer sheath 121 comprises anchors 122 that project from one side face 123 of the outer sheath. When the anastomosis ring 120 is assembled, the anchors 122 project laterally from a side face of the ring and are orientated to go directly into the opposing ring. This tissue gripping feature creates an interlocking grip of the tissue. The spikes are orientated to cross over each other.

Figure 100:
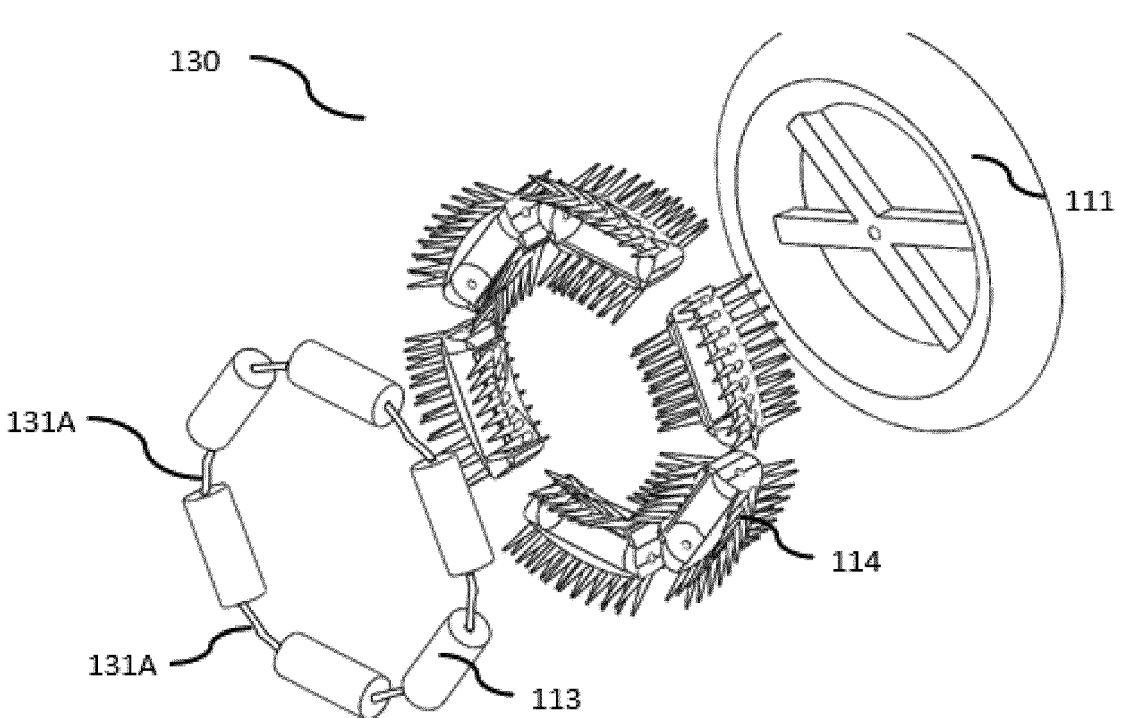
FIG. 100 is an exploded view of a compression anastomosis ring according to an alternative embodiment of the invention.
Figure 101:
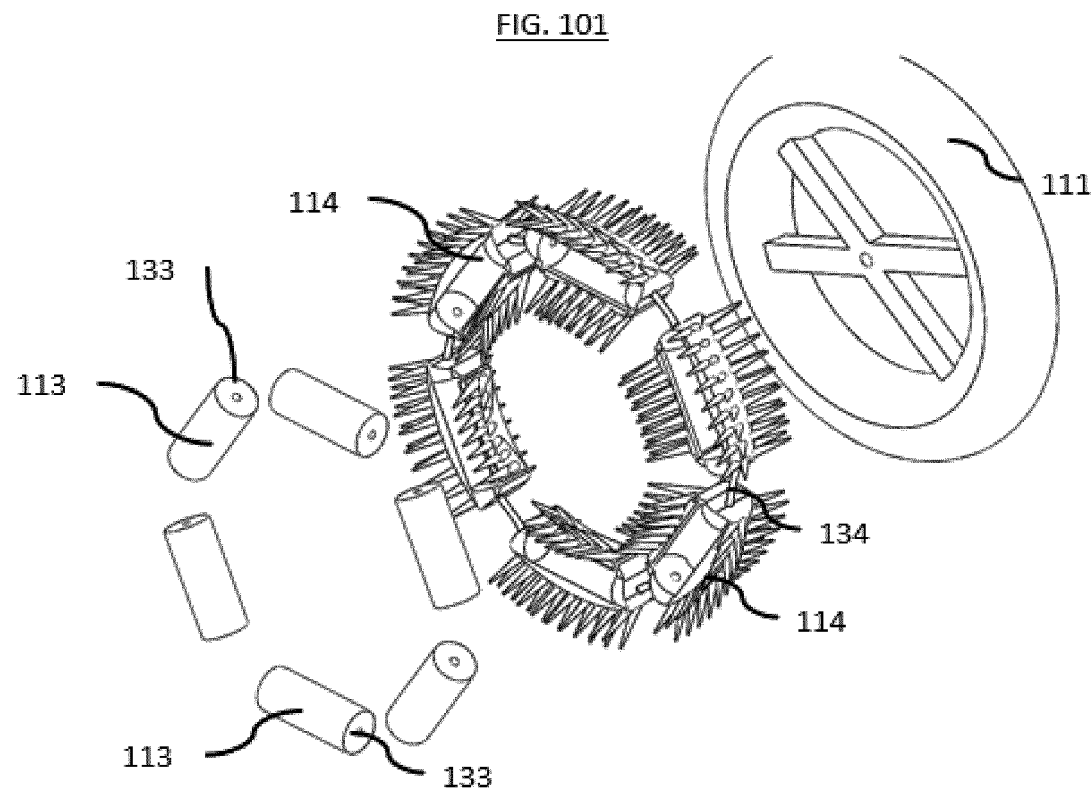
FIG. 101 is an exploded view of a compression anastomosis ring according to an alternative embodiment of the invention.

Referring to FIGS. 100 to 102, an alternative embodiment of the compression ring, indicated generally by the reference numeral 130, is described in which parts described with reference to the previous embodiment are assigned the same reference numerals. In this embodiment, the cylindrical inner cores 113 are connected together in series by a thread 131 that is usually flexible. The thread 131 may be provided by a plurality of connecting threads 131A each of which connects one end of one inner core to an end of a second inner core. Alternatively, the inner cores may comprise through holes 133 and may be mounted on a single thread loop 134 as illustrated in FIG. 101. In FIG. 102, the inner cores are not connected but the outer sheaths are connected together in series by a thread 135.

Referring to FIG. 103, an alternative embodiment of the compression ring, indicated generally by the reference numeral 140, is described in which parts described with reference to the previous embodiment are assigned the same reference numerals. In this embodiment, the ring comprises a helical coil 141 that is wound around the annular hollow tube 111. The coil 141 comprises anchors in the form of barbs 142 configured to anchor to tissue of the body lumen. The barbs are positioned on a diametrically outer and side parts of the coil.

Figure 104:
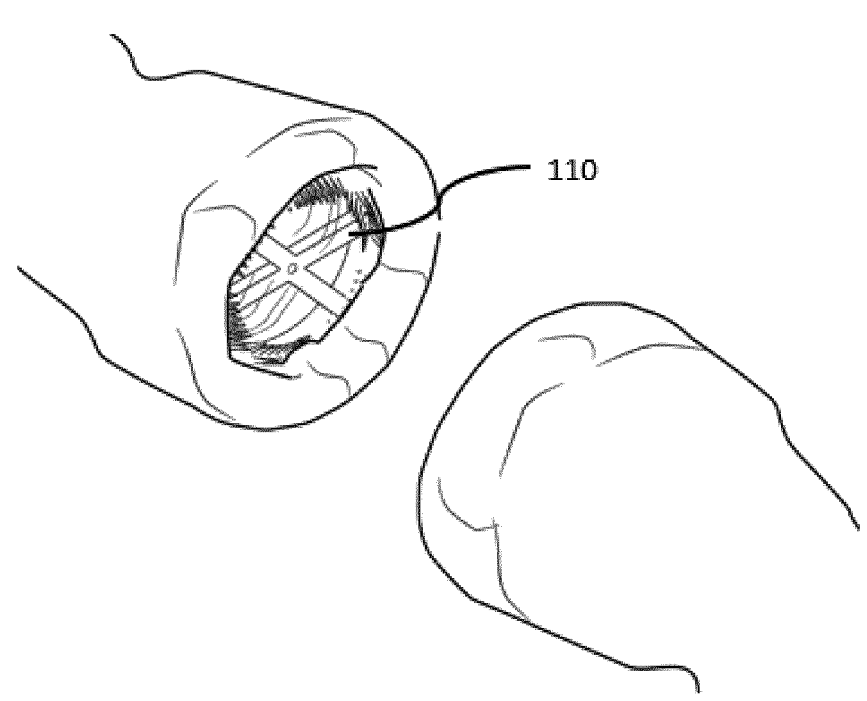
FIG. 104 is an illustration of the use of a compression anastomosis system comprising two compression anastomosis rings of FIG. 83 forming a compression anastomosis of a cut colon.
Figure 105:
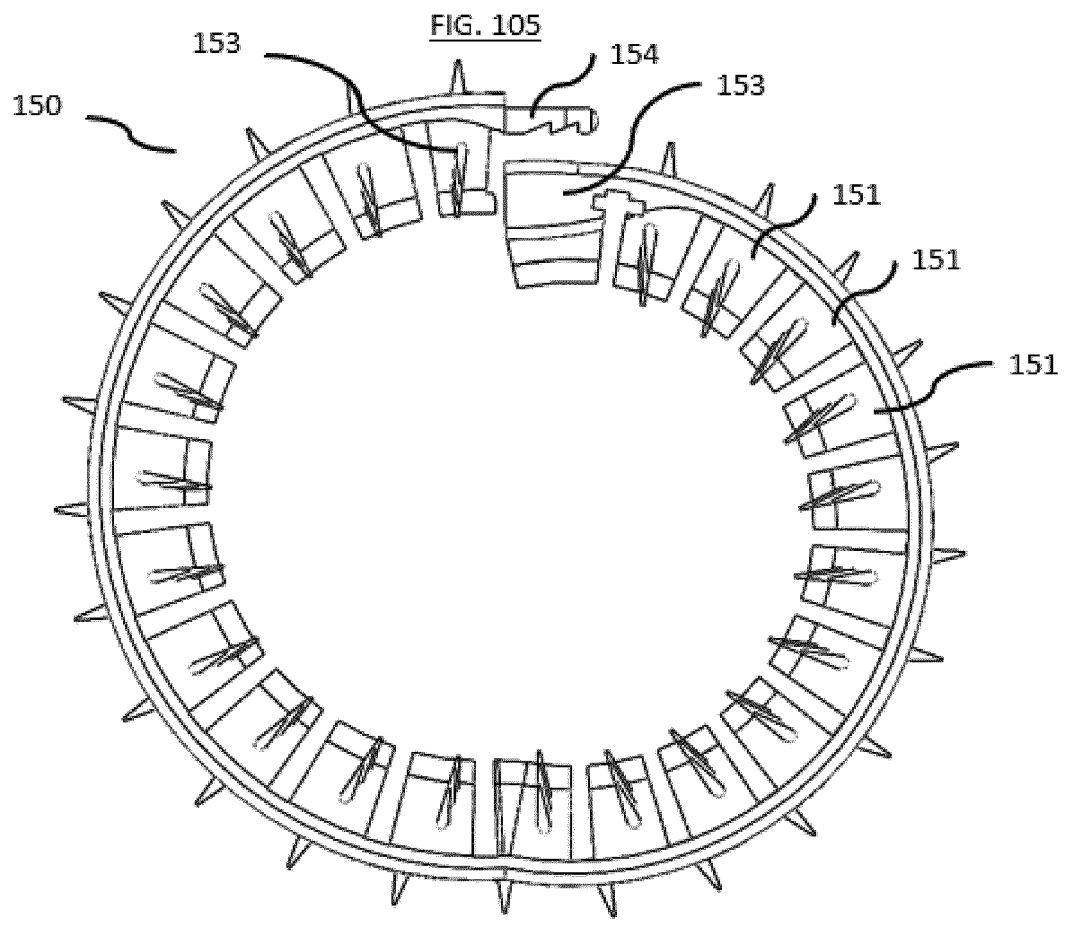
FIG. 105 is a side elevational view of a compression anastomosis ring according to an alternative embodiment of the invention in which the ring is configured for adjustment from an open-ring configuration for delivery and a closed-ring deployed configuration and shown in an open-ring configuration.
Figure 106:
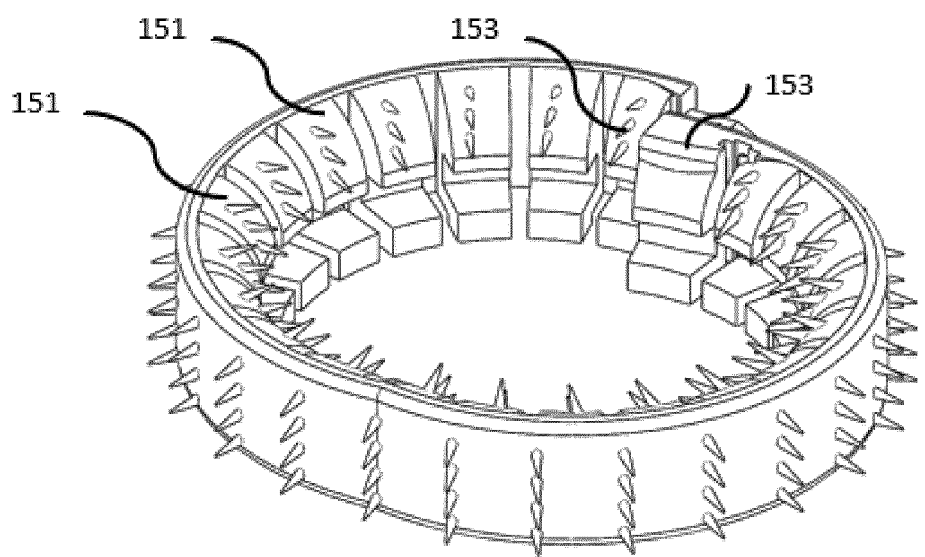
FIG. 106 is a perspective view of a compression anastomosis ring of FIG. 105.

FIG. 104 illustrates the use of the compression rings of the invention to form a compression anastomosis. A first compression ring 110 is deployed inside a first open of a colon and a second compression ring (not shown) is deployed inside a second open end of the colon. In this position, the free end of the colon drapes around the exposed face of each ring where it is gripped by the anchors. The two rings are then brought together and magnetically coupled together to form a compression anastomosis. This is left in-situ for a period of weeks allowing the cut ends of the colon heal and knit together, whereupon the annular hollow tube of each ring will biodegrade to release the rings segments that will pass through the colon and anus naturally.

Figure 107:
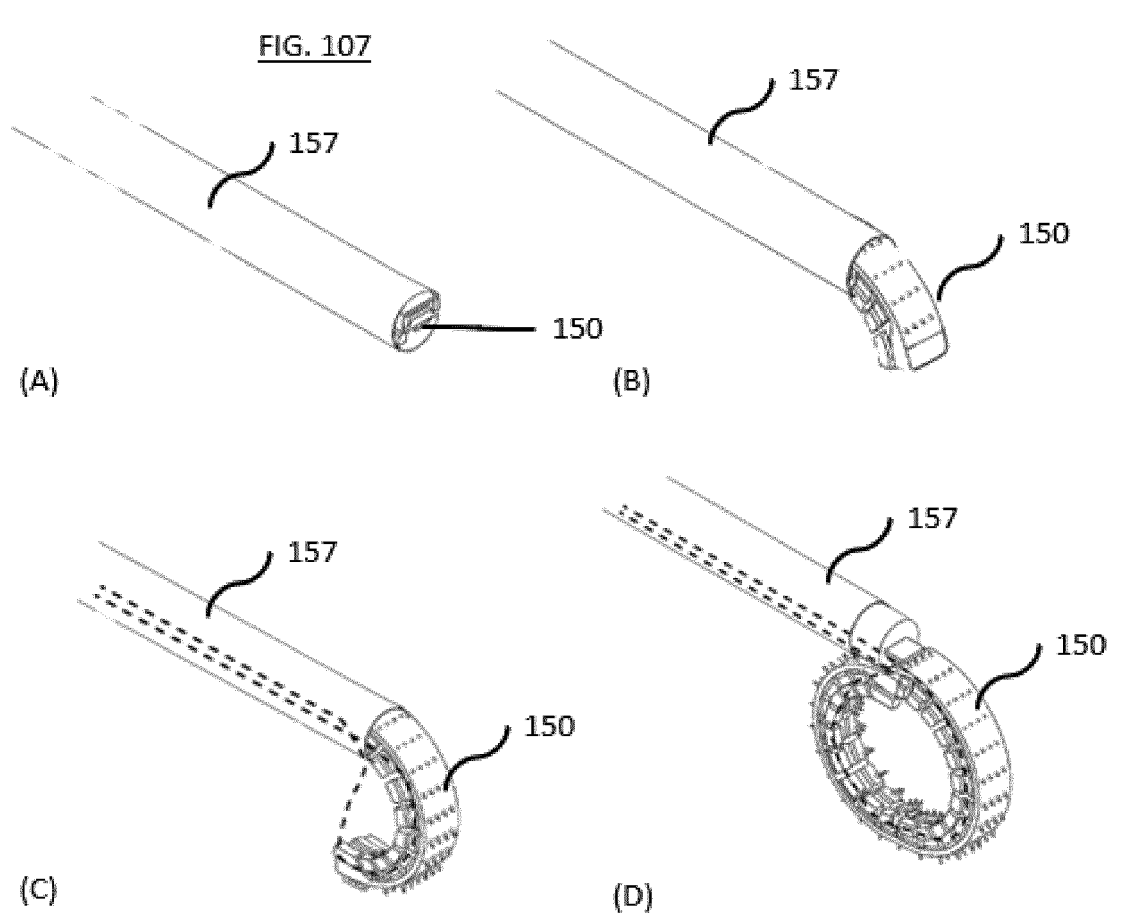
FIG. 107 illustrates (A) an elongated laparoscopic surgical device containing the compression anastomosis ring of FIG. 105 in an open-ring configuration disposed in a central lumen of the device, (B) and (C) the ring partially advanced out of the device along an activation filament, and (D) the ring fully advanced out of the device.
Figure 108:
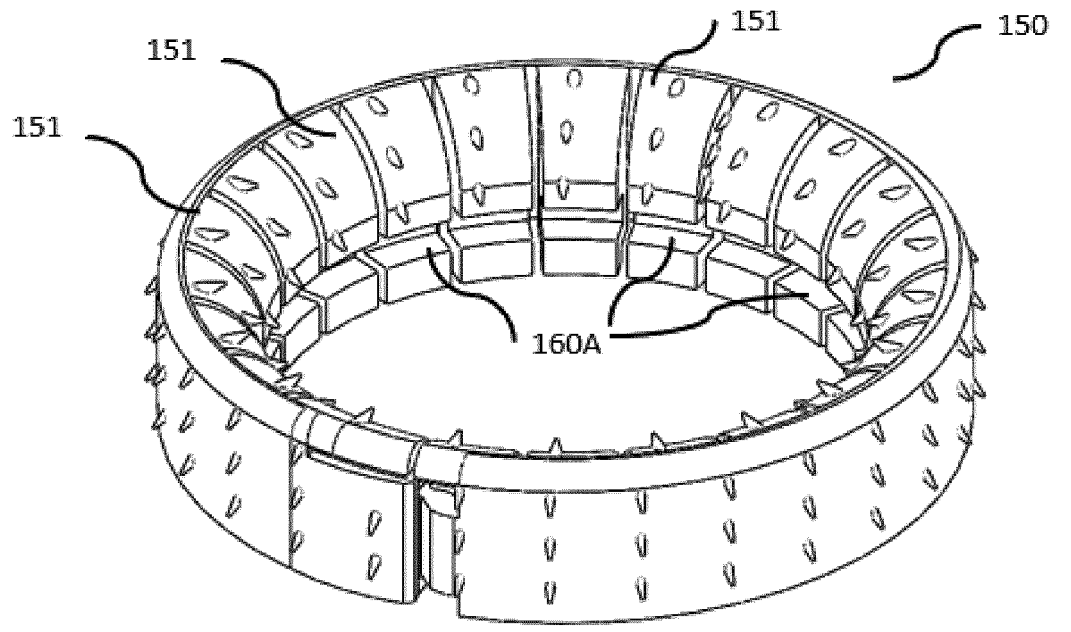
FIG. 108 shows the compression anastomosis ring of FIG. 105 deployed in a closed ring configuration.
Figure 109:
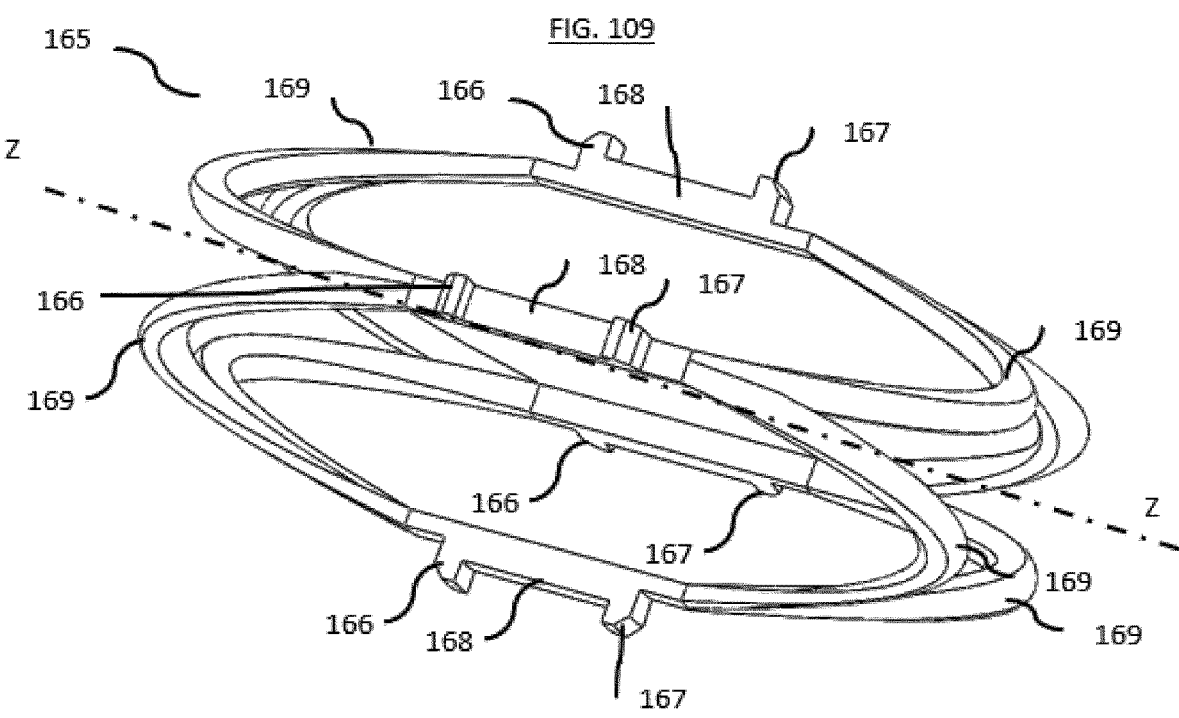
FIG. 109 is a perspective view of a coupling insert forming part of the compression anastomosis system according to one embodiment of the invention.
Figure 110:
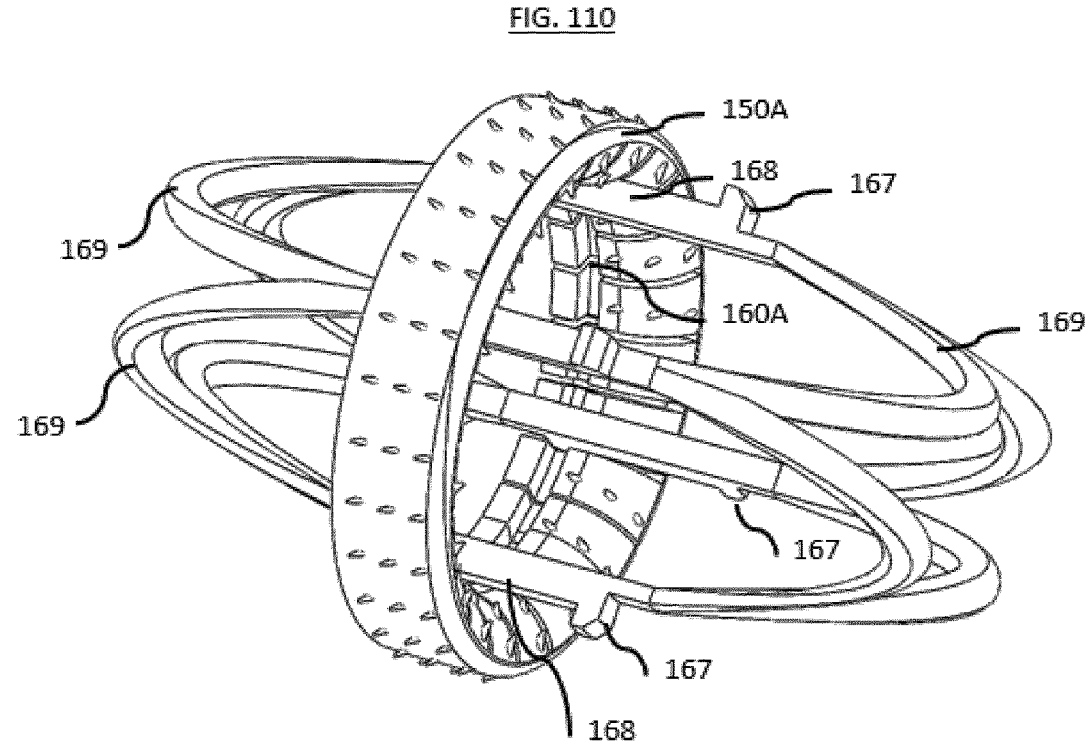
FIG. 110 shows a compression anastomosis ring of FIG. 105 mounted to one side of the coupling insert of FIG. 109.

Referring to FIGS. 105 to 112, an alternative embodiment of the compression ring, indicated generally by the reference numeral 150, is described in which parts described with reference to the previous embodiment are assigned the same reference numerals. In this embodiment, the ring 150 is configured for adjustment from an open ring (FIGS. 105 to 107) to a closed ring (FIGS. 108 and 110). The ring 150 is formed from ring segments 151 hingedly connected together in series and is adjustable from an open ring elongated configuration suitable for delivery through a laparoscopic surgical instrument to a deployed closed ring configuration. The ring 150 comprises end segments 153 configured for coupling together—in the embodiment shown, one end segment 153A comprises a latching arm 154 and the other end segment 1538 comprises a latching formation (not shown) configured to couple with the latching arm 154. It will be appreciated that the ring can be closed using other coupling arrangements, including magnetic coupling elements. In this embodiment, the ring is configured to self-deploy when released from a delivery configuration to the ring-shaped configuration shown in FIG. 105. The delivery of the ring 150 from a laparoscopic surgical instrument 157 along an activation filament is illustrated in FIG. 107.

Referring to FIG. 108, coupling elements are provided on the ring in the form of an annular groove provided on an inner periphery of the ring when deployed. Each ring segment 151 comprises a groove part 160A disposed on an inner face of the segment, such that when the ring is deployed the groove parts 160A align to form an annular groove.

Referring to FIG. 109, a coupling insert 165 is illustrated and comprises a frame 166 configured for radial expansion about an axis Z, a first series of coupling formations 166 disposed along a first circumference of the frame and a second series of coupling formations 167 disposed along a second circumference of the frame that is parallel to and spaced apart from the first circumference. The frame comprises four supports 168 spaced around the circumference of the frame, and the supports are connected in series around the axis Z by resiliently deformable curved supporting stuts 169 in which each support 168 is connected to an adjacent support 168 by two supporting struts 169.

Figure 111A:
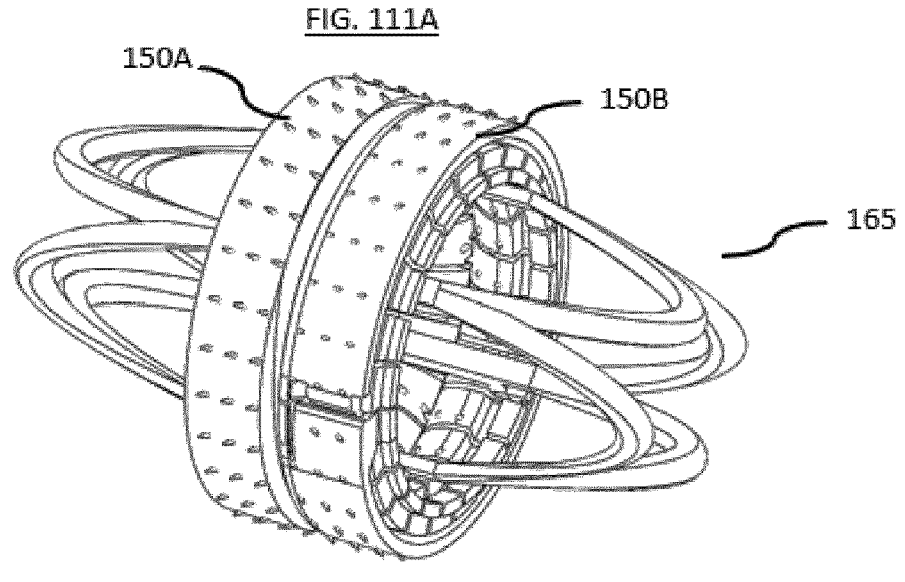
FIG. 111 (A, B and C) show two compression anastomosis rings of FIG. 105 mounted to the coupling insert of FIG. 109.
Figure 111B:
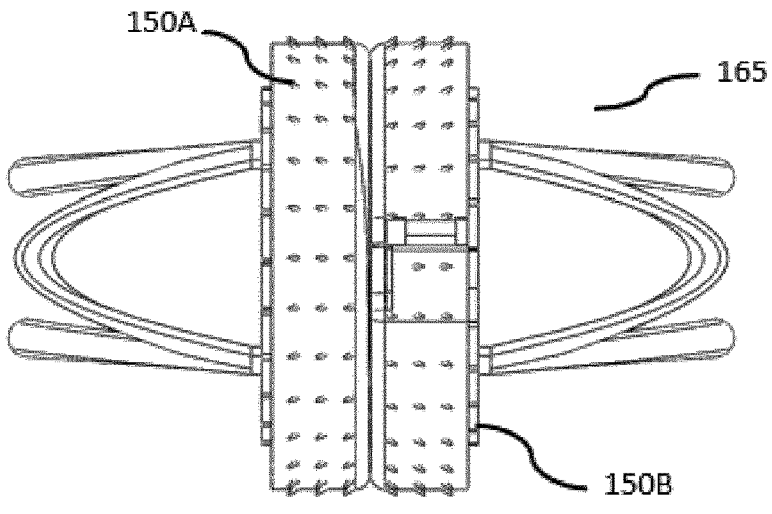
Figure 111C:
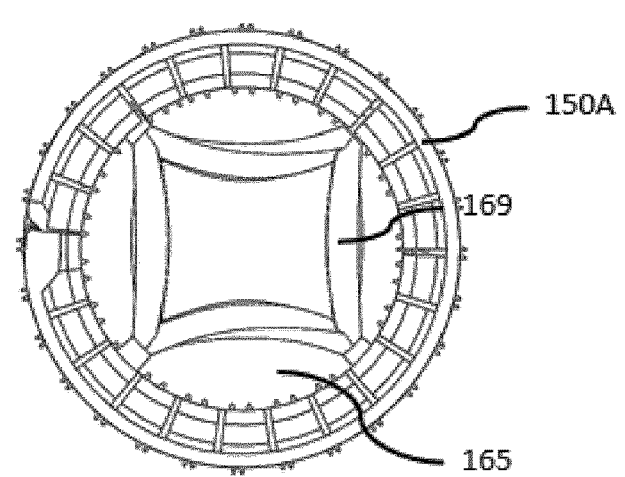
Figure 112A:
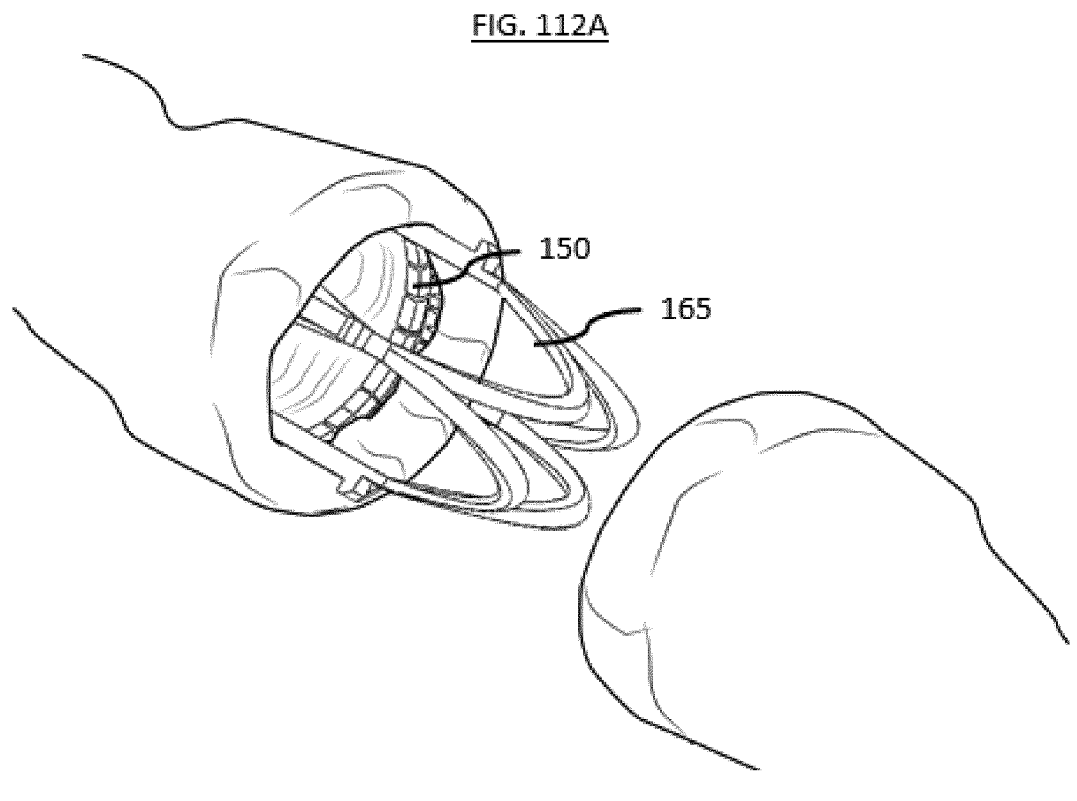
FIG. 112A shows a first compression anastomosis ring of FIG. 105 mounted to one side of the coupling insert of FIG. 109 and deployed in a first open cut end of a colon, and a second compression anastomosis ring of FIG. 105 (not shown) deployed in a second open cut end of a colon.
Figure 112B:
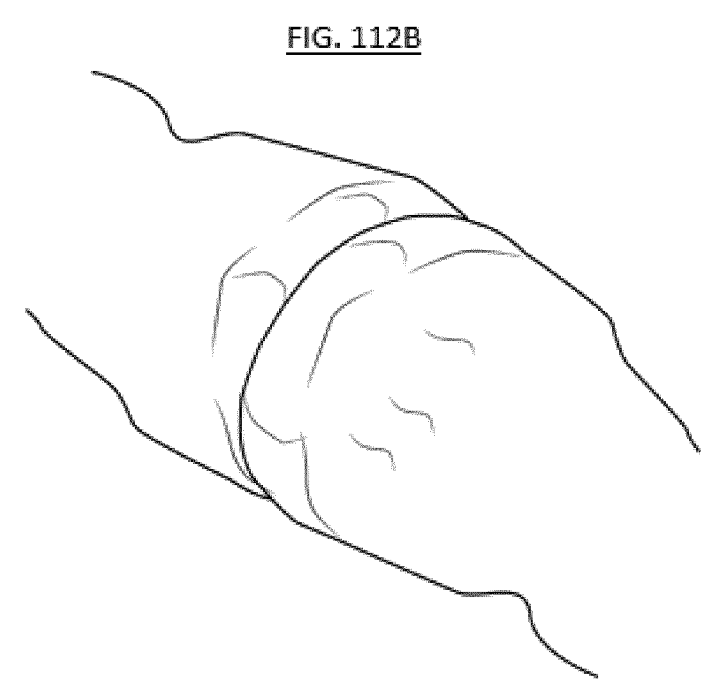
FIG. 112B shows a compression anastomosis formed when the second compression anastomosis ring of FIG. 112A is mounted to the second side of the coupling element.

The coupling insert 165 is shown in its deployed configuration in FIG. 109. FIG. 110 illustrates how a first ring 150A is coupled to one side of the coupling insert 165, with the circumferentially arranged coupling formations 166 engaging the annular groove 160 of the ring 150A. FIG. 111 shows how a second ring 1506 couples to an opposite side of the coupling insert 165 with the circumferentially arranged coupling formations 167 engaging the annular groove 160 of the ring 1506, to bring the two rings together in a compression anastomosis forming configuration. FIG. 112 illustrates the use of this embodiment to form a compression anastomosis of the colon.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A compression anastomosis system comprising matching first and second compression ring devices (1, 40, 50, 60, 70, 80, 90), each compression ring device configured for adjustment from an elongated delivery closed ring configuration suitable for passing through a lumen of a minimally invasive surgical instrument to a deployed radially expanded closed ring configuration, wherein the first and second compression ring devices comprise magnetic coupling elements (20, 41, 56, 57) configured to couple the rings together in a face-to-face compression anastomosis configuration in which configuration a first side face of the first compression ring device faces and is coupled to a second side face of the second compression ring device to compress tissue between the first side face and second side face, and wherein the first side face of the first compression ring device and the second side face of the second compression ring device each comprise a plurality of tissue anchors configured to anchor the first and second the compression ring devices to a wall of a body lumen when each ring is deployed in the body lumen.

2. The compression anastomosis system according to claim 1, in which all or part of each compression ring device is configured to biodegrade in-vivo.

3. The compression anastomosis system according to claim 1, in which one or more parts of the or each compression ring device is configured to biodegrade in-vivo to break the or each compression ring device into a plurality of smaller parts.

4. The compression anastomosis system according to claim 1, in which the compression ring is dimensioned in the elongated delivery closed ring configuration to pass through a lumen having a diameter of no greater than 15 mm and dimensioned in the deployed closed ring configuration to circumferentially abut an inner wall of a body lumen.

5. The compression anastomosis system according to claim 1, in which each compression ring device comprises a central spoke element configured to assist in the deployment of the compression ring device, and fold when the compression ring device is compressed into a delivery configuration.

6. The compression anastomosis system according to claim 1, in which the first and second compression ring devices each comprise an inflatable ring (2) whereby inflation of the inflatable annular ring deploys the compression ring device into the radially expanded deployed configuration to circumferentially abut an inner wall of a body lumen.

7. The compression anastomosis system according to claim 1, in which the coupling elements comprise a series of latching arms (20) mounted to and extending axially from the first compression ring device, and a formation (22, 60)

on the second compression ring device configured to receive an end (21) of the latching arm to lock the first and second compression ring devices together in a compression anastomosis configuration.

8. The compression anastomosis system according to claim 1, in which the coupling elements comprise magnets of one polarity (56) disposed on a side of the first compression ring device and corresponding magnets of a second polarity (57) disposed on a side of the second compression ring device.

9. The compression anastomosis system according to claim 1, in which the or each anastomosis ring comprises:

an annular hollow tube that is biased into a ring shape and resiliently deformable; and a plurality of ring segments disposed within the annular hollow tube, wherein the anastomosis ring is configured to be resiliently deformed into an elongated delivery configuration suitable for delivery in a minimally invasive surgical instrument and to self-deploy into a radially expanded configuration suitable to fully or at least partially circumferentially abut an inner wall of a body lumen upon release from the surgical instrument.

10. The compression anastomosis system according to claim 9, in which one or more of the ring segments comprise a magnetic or magnetisable material to provide the coupling element for coupling two rings together.

11. The compression anastomosis system according to claim 9, in which one side of the or each ring segment comprises a magnetic or magnetisable material of a first polarity and an opposite side of the ring segments comprises a magnetic or magnetisable material of a second polarity.

12. The compression anastomosis system according to claim 9, in which the annular hollow tube comprises a resiliently deformable polymeric material.

13. The compression anastomosis system according to claim 9, in which one or more of the ring segments comprise an inner core and an outer sheath, in which the inner core comprises the magnetic or magnetisable material.

14. The compression anastomosis system according to claim 13, in which the outer sheath comprises the tissue anchors and in which the tissue anchors and annular hollow tube are configured such that upon assembly of the anastomosis ring the tissue anchors project through the annular hollow tube to provide tissue anchors on a side face of the ring.

15. The compression anastomosis system according to claim 1, in which the tissue anchors comprise:

anchors disposed on the first side face of the first compression ring device; and anchors disposed on the second side face of the second compression ring device.

16. The compression anastomosis system according to claim 13, in which the outer sheath is configured to shield a magnetic force on one side of the inner core.

17. The compression anastomosis system according to claim 1, in which the or each anastomosis ring is configured to be adjustable from an open ring formation and a closed ring formation.

18. The compression anastomosis system according to claim 9, comprising a coupling insert configured to couple to the coupling elements of matching first and second compression ring devices to couple the rings together.

19. The compression anastomosis system according to claim 15, in which the outer anchors of one ring are configured to interdigitate with the outer anchors of a matching ring when the two rings couple together to form a compression anastomosis.

20. A compression anastomosis system comprising matching first and second compression ring devices (1, 40, 50, 60, 70, 80, 90), each compression ring device configured for adjustment from an elongated delivery configuration suitable for passing through a lumen of a minimally invasive surgical instrument to a deployed radially expanded configuration, wherein the compression rings comprise coupling elements (20, 41, 56, 57) for coupling the rings together in a face-to-face compression anastomosis configuration, and wherein each compression ring device comprising tissue anchors (12, 58) configured to anchor the ring to a wall of a body lumen when the ring is deployed in the body lumen, in which the or each anastomosis ring in the deployed radially expanded configuration comprises:

an annular tube that is biased into a ring shape and resiliently deformable; and a plurality of ring segments disposed within the annular tube.

21. A compression anastomosis system comprising matching first and second compression ring devices (1, 40, 50, 60, 70, 80, 90), wherein each anastomosis ring is configured to self-deploy from an elongated delivery configuration suitable for delivery in a minimally invasive surgical instrument to a radially expanded configuration, wherein each anastomosis ring in the radially expanded configuration comprises:

an annular tube that is biased into a ring shape and resiliently deformable; and a plurality of unconnected ring segments disposed within the annular tube.

22. A compression anastomosis system comprising matching first and second compression ring devices (1, 40, 50, 60, 70, 80, 90), wherein each anastomosis ring is configured to self-deploy from an elongated delivery configuration suitable for delivery in a minimally invasive surgical instrument to a radially expanded configuration, wherein the or each anastomosis ring in the radially expanded configuration comprises:

an annular tube that is biased into a ring shape and resiliently deformable; and a plurality of unconnected ring segments disposed within the annular tube, wherein each ring segment is magnetic.

23. A compression anastomosis system comprising matching first and second compression ring devices (1, 40, 50, 60, 70, 80, 90), wherein each anastomosis ring is configured to self-deploy from an elongated delivery configuration suitable for delivery in a minimally invasive surgical instrument to a radially expanded configuration, wherein the or each anastomosis ring in the radially expanded configuration comprises:

an annular tube that is biased into a ring shape and resiliently deformable; and a plurality of unconnected ring segments disposed within the annular tube, wherein each segment is mounted in a sheath, wherein the sheath comprises tissue anchors that extend through the annular tube to present the tissue anchors on the surface of the or each anastomosis ring.

* * * * *